United States Patent
Pyo et al.

(10) Patent No.: US 11,545,629 B2
(45) Date of Patent: *Jan. 3, 2023

(54) ORGANIC LIGHT-EMITTING DIODE WITH HIGH EFFICIENCY AND LOW VOLTAGE

(71) Applicant: SFC CO., LTD., Cheongju (KR)

(72) Inventors: Sung-Wan Pyo, Daejeon (KR); So Young Shim, Daejeon (KR); Yun-Ah Lee, Suwon (KR); Se Jin Yu, Gyeongsan (KR)

(73) Assignee: SFC CO., LTD., Cheongju (KR)

( * ) Notice: Subject to any disclaimer, the term of this patent is extended or adjusted under 35 U.S.C. 154(b) by 429 days.

This patent is subject to a terminal disclaimer.

(21) Appl. No.: 15/334,758

(22) Filed: Oct. 26, 2016

(65) Prior Publication Data

US 2017/0133600 A1    May 11, 2017

(30) Foreign Application Priority Data

Nov. 10, 2015 (KR) .................. 10-2015-0157063

(51) Int. Cl.
*H01L 51/00* (2006.01)
*C09K 11/06* (2006.01)
(Continued)

(52) U.S. Cl.
CPC ........ *H01L 51/0061* (2013.01); *C07D 307/77* (2013.01); *C07D 307/94* (2013.01);
(Continued)

(58) Field of Classification Search
CPC ... C07C 211/54; C07C 211/55; C07C 211/60; C07D 307/77; C07D 307/91;
(Continued)

(56) References Cited

U.S. PATENT DOCUMENTS

| 2012/0168734 A1* | 7/2012 | Park ................. | C09K 11/06 257/E51.026 |
| 2015/0325800 A1* | 11/2015 | Ito ................... | H05B 33/20 257/40 |

(Continued)

FOREIGN PATENT DOCUMENTS

| KR | 1020080015865 | 2/2008 |
| KR | 1020120038402 A | 4/2012 |

(Continued)

OTHER PUBLICATIONS

Office Action from Korean Intellectual Property Office of 10-2016-0120584, dated Oct. 4, 2018.

*Primary Examiner* — Sean M DeGuire
(74) *Attorney, Agent, or Firm* — STIP Law Group, LLC

(57) ABSTRACT

Disclosed herein is an organic light-emitting diode capable of operating at a low voltage with high efficiency. It comprises: a first electrode; a second electrode facing the first electrode; and a light-emitting layer interposed between the first electrode and the second electrode, wherein the light-emitting layer comprises at least one of the amine compounds represented by the following Chemical Formula A or B, and the compound represented by the following Chemical Formula C. Chemical Formulas A, B and C are as described in the Specification.

13 Claims, 1 Drawing Sheet

(51) Int. Cl.
| | |
|---|---|
| *C09K 11/02* | (2006.01) |
| *C07D 307/94* | (2006.01) |
| *C07D 493/10* | (2006.01) |
| *C07D 307/77* | (2006.01) |
| *H05B 33/20* | (2006.01) |
| *H05B 33/14* | (2006.01) |
| *H01L 51/50* | (2006.01) |

(52) U.S. Cl.
CPC .......... *C07D 493/10* (2013.01); *C09K 11/025* (2013.01); *C09K 11/06* (2013.01); *H01L 51/0052* (2013.01); *H01L 51/0073* (2013.01); *H05B 33/14* (2013.01); *H05B 33/20* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/1033* (2013.01); *C09K 2211/1088* (2013.01); *C09K 2211/1092* (2013.01); *H01L 51/0067* (2013.01); *H01L 51/0074* (2013.01); *H01L 51/5012* (2013.01); *H01L 2251/308* (2013.01)

(58) Field of Classification Search
CPC .......... C07D 405/14; C09K 2211/1011; H01L 51/0059; H01L 51/0072; H01L 51/0073; H01L 51/0074
See application file for complete search history.

(56) References Cited

U.S. PATENT DOCUMENTS

2016/0351818 A1\* 12/2016 Kim ...................... C09K 11/06
2017/0141322 A1\* 5/2017 Cha .................... H01L 51/0073

FOREIGN PATENT DOCUMENTS

| KR | 1020120047706 | 5/2012 |
| KR | 1020150043020 | 4/2015 |
| KR | 1020160141360 A | 12/2016 |
| KR | 1020160141361 A | 12/2016 |
| WO | WO2015022051 A1 | 2/2015 |

\* cited by examiner

ORGANIC LIGHT-EMITTING DIODE WITH HIGH EFFICIENCY AND LOW VOLTAGE

CROSS REFERENCE TO RELATED APPLICATION(S)

This application claims priority to and incorporates herein by reference all disclosure in Korean Patent Application No. 10-2015-0157063 filed Nov. 10, 2015.

BACKGROUND OF THE INVENTION

Field of the Invention

The present disclosure relates to an organic light-emitting diode with high efficiency and low driving voltage. More particularly, the present disclosure relates to an organic light-emitting diode wherein host and dopant materials of specific structures are used in a light-emitting layer.

Description of the Related Art

Organic light-emitting diodes (OLEDs), based on self-luminescence, are used to create digital displays having the advantage of being able to be made thinner and lighter than liquid crystal displays. In addition, an OLED display exhibits a much faster response time than an LCD. Accordingly, organic light-emitting diodes find applications in the illumination field as well as the full-color display field.

Materials used as the organic layers in organic light emitting diodes may be divided into luminescent materials and charge carrier materials, for example, a hole injection material, a hole transport material, an electron injection material, and an electron transport material. According to the luminescent materials, there are two main families of OLED: those based on small molecules and those employing polymers. The light emitting mechanisms allows the luminescent materials to be classified as fluorescent and phosphorescent materials, which use excitons in singlet and triplet states, respectively.

Meanwhile, when a single material is employed as the luminescent material, intermolecular actions cause the maximum luminescence wavelength to shift toward a longer wavelength, resulting in a reduction in color purity and light emitting efficiency. In this regard, a host-dopant system may be used as a luminescent material so as to increase the color purity and the light emitting efficiency through energy transfer.

This is based on the principle that, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kind of the dopant because the wavelength of the host moves to the wavelength range of the dopant.

With regard to the related arts pertaining to dopant compounds in the light-emitting layer, reference may be made to Korean Unexamined Patent Application Publication No. 10-2008-0015865 (Feb. 20, 2008), which describes an organic light emitting device using an arylamine-coupled indenofluorene derivative, and to Korean Unexamined Patent Application Publication No. 10-2012-0047706 (May 14, 2012), which describes an organic photoelectric device using a compound in which dibenzofuran or dibenzothiophene coexists with fluorene or carbazole.

As a related art for using a host compound in a light-emitting layer, mention may be made of Korean Unexamined Patent Application Publication No. 10-2015-0043020, which describes an organic light-emitting diodes employing anthracene derivatives as fluorescent hosts.

However, there is still a continued need to develop organic light-emitting diodes exhibiting a low driving voltage and higher efficiency.

RELATED ART DOCUMENT

Korean Unexamined Patent Application Publication No. 10-2008-0015865 (Feb. 20, 2008)
Korean Unexamined Patent Application Publication No. 10-2012-0047706 (May 14, 2012)
Korean Unexamined Patent Application Publication No. 10-2015-0043020 (Apr. 22, 2015)

SUMMARY OF THE INVENTION

Therefore, the present disclosure aims to provide a novel organic light-emitting diode (OLED) that can operate at a low voltage with high efficiency, wherein dopant and host materials of specific structures are employed.

In accordance with an aspect thereof, the present disclosure provides an organic light-emitting diode, comprising: a first electrode; a second electrode facing the first electrode; and a light-emitting layer interposed between the first electrode and the second electrode, wherein the light-emitting layer comprises at least one of the amine compounds represented by the following Chemical Formula A or B, and the compound represented by the following Chemical Formula C:

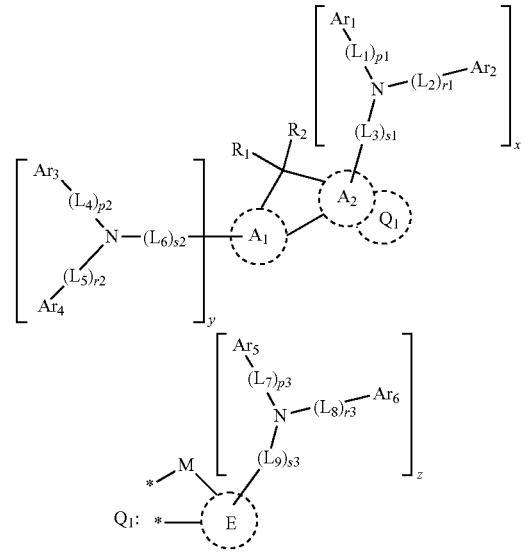

[Chemical Formula A]

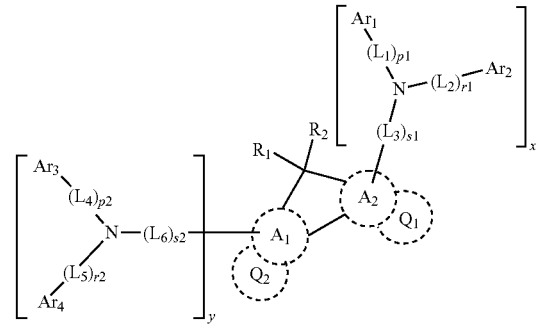

[Chemical Formula B]

-continued

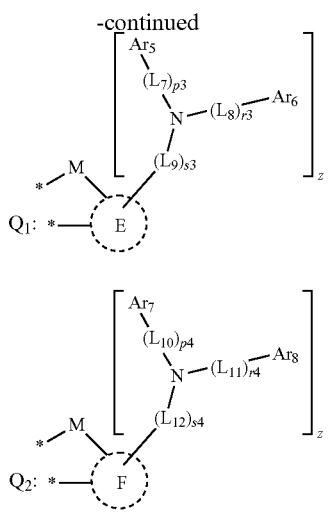

wherein,

A₁, A₂, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which the substituents $R_1$ and $R_2$ are bonded;

linkers $L_1$ to $L_{12}$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_8$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkyl germanium of 1 to 30 carbon atoms, a substituted or unsubstituted aryl germanium of 6 to 30 carbon atoms, a cyano, a nitro, and a halogen, with the proviso that $R_1$ and $R_2$ together may form a mono- or polycyclic aliphatic or aromatic ring, which may be a heterocyclic ring containing a heteroatom selected from among N, O, P, Si, S, Ge, Se, and Te as a ring member;

p1 to p4, $R_1$ to $R_4$, and s1 to s4 are each independently an integer of 1 to 3, with the proviso that when any of them is 2 or greater, the corresponding linkers may be the same or different, x is an integer of 1 or 2, and y and z may be the same or different, and are each independently an integer of 0 to 3; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$, two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring,

[Chemical Formula C]

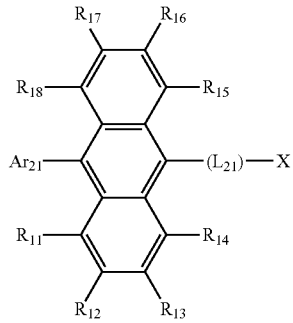

wherein, $Ar_{21}$ is selected from among a substituted or unsubstituted aryl of 6 to 50 carbon atoms, and a substituted or unsubstituted heteroaryl of 3 to 50 carbon atoms containing O, N or S as a heteroatom:

$L_{21}$ is selected from among a substituted or unsubstituted arylene of 6 to 50 carbon atoms, and a substituted or unsubstituted heteroarylene of 3 to 50 carbon atoms containing O, N or S as a heteroatom;

$R_{11}$ and $R_{18}$ may be the same or different, and are each independently selected from the group consisting of hydrogen, deuterium, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 3 to 50 carbon atoms containing O, N or S as a heteroatom, a substituted or unsubstituted silicone, a substituted or unsubstituted boron, a substituted or unsubstituted silane, a carbonyl, a phosphoryl, an amino, a nitrile, a hydroxyl, a nitro, a halogen, an amide, and an ester;

$R_{12}$ and $R_{16}$ may form a saturated or unsaturated ring with $R_{13}$ and $R_{17}$, respectively X is a substituent represented by the following Structural Formula A,

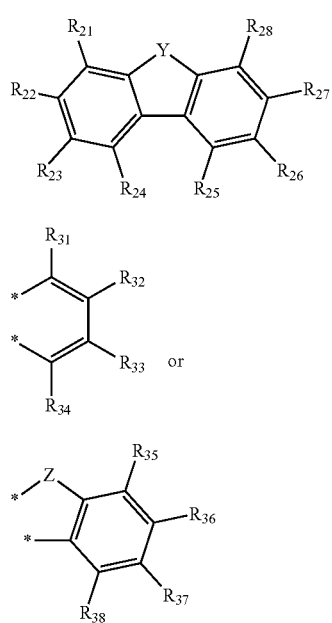

[Structural Formula A]

P1

P2 wherein,

Y and Z may be the same or different, and are each independently an oxygen atom or a sulfur atom, $R_{21}$ to $R_{38}$ may be the same or different, and are each independently selected from among a hydrogen atom, a deuterium atom, a substituted or unsubstituted alkyl of 1 to 30 carbon atoms, a substituted or unsubstituted cycloalkyl of 1 to 30 carbon atoms, a substituted or unsubstituted alkoxy of 1 to 30 carbon atoms, a substituted or unsubstituted aryl of 6 to 50 carbon atoms, a cyano, a halogen, and a silyl, two adjacent substituents of $R_{21}$ to $R_{24}$ occupy respective positions '*' of P1 or P2, and any one substituent of $R_{25}$ to $R_{28}$ represents a single bond connected to the linker $L_{21}$, wherein the term 'substituted' in the expression 'substituted or unsubstituted' for Chemical Formulas A, B and C means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 1 to 24 carbon atoms, an alkylsilyl of 1 to 24 carbon atoms, an arylsilyl of 6 to 24 carbon atoms, and an aryloxy of 6 to 24 carbon atoms.

BRIEF DESCRIPTION OF THE DRAWINGS

The above and other objects, features and advantages of the present disclosure will be more clearly understood from the following detailed description taken in conjunction with the accompanying drawing, in which:

FIGURE is a schematic cross-sectional view of the structure of an organic light-emitting diode according to some embodiments of the present disclosure.

DESCRIPTION OF THE PREFERRED EMBODIMENTS

Hereinafter, some embodiments which can be easily embodied by those skilled in the art will be described with reference to the accompanying drawings. In the drawings of the invention, the sizes and dimensions of structures are illustrated by enlarging or reducing them relative to the actual sizes and dimensions to clarify the invention, the known configurations are not illustrated in order to emphasize characteristic configurations, and the invention is not limited to the drawings. In describing the phenomena of the preferred embodiments of the invention in detail, when it is determined that a detailed description of related known functions or configurations may unnecessarily obscure the gist of the invention, such a detailed description is omitted.

In addition, the size and thickness of each configuration illustrated in the drawings are arbitrarily illustrated for the sake of convenience of explanation, and thus the present disclosure may not be necessarily limited to what is shown in the illustration. Further, in the drawings, the thicknesses of layers and regions may be exaggerated for clarity. It will be understood that when an element such as a layer, film, region or substrate is referred to as being "on" another element, it may be directly on the other element or intervening elements may also be present.

Throughout the specification, when a portion may "include" a certain constituent element, unless specified otherwise, it may not be construed to exclude another constituent element but may be construed to further include other constituent elements.

In addition, unless explicitly described to the contrary, the word "comprise" and variations such as "comprises" or "comprising" will be understood to imply the inclusion of stated elements but not the exclusion of any other elements. Further, throughout the specification, the word "on" means positioning on or below the object portion, but does not essentially mean positioning on the lower side of the object portion based on a direction of gravity.

The present disclosure addresses an organic light-emitting diode, comprising: a first electrode; a second electrode facing the first electrode; and a light-emitting layer interposed between the first electrode and the second electrode, wherein the light-emitting layer comprises at least one of the amine compounds represented by the following Chemical Formula A or B, and the compound represented by the following Chemical Formula C:

[Chemical Formula A]

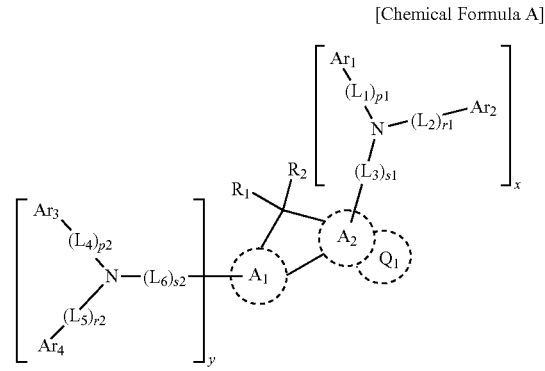

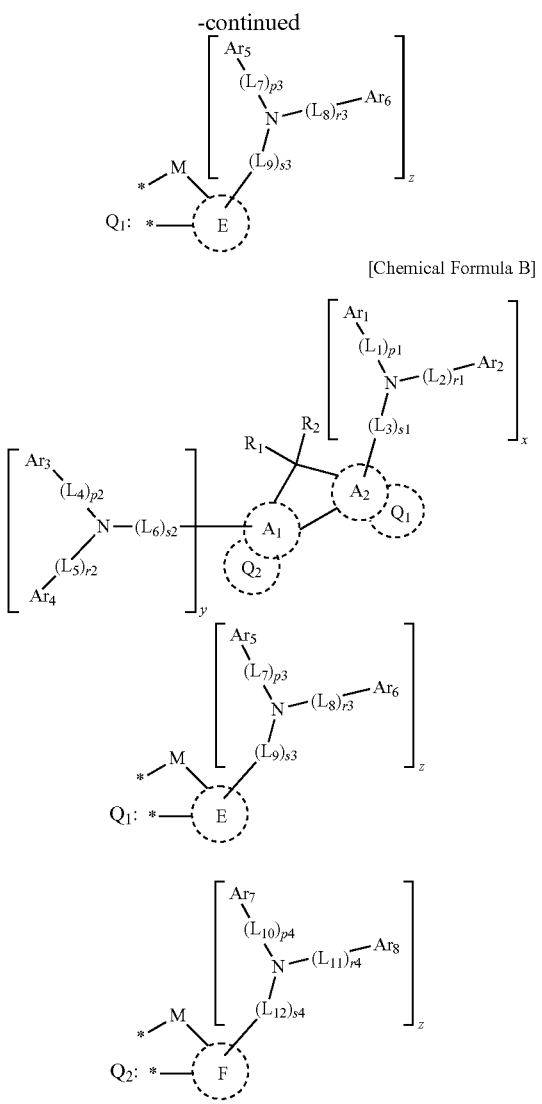

[Chemical Formula B]

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which the substituents $R_1$ and $R_2$ are bonded;

linkers $L_1$ to $L_{12}$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_8$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkyl germanium of 1 to 30 carbon atoms, a substituted or unsubstituted aryl germanium of 6 to 30 carbon atoms, a cyano, a nitro, and a halogen, with the proviso that $R_1$ and $R_2$ together may form a mono- or polycyclic aliphatic or aromatic ring, which may be a heterocyclic ring containing a heteroatom selected from among N, O, P, Si, S, Ge, Se, and Te as a ring member;

p1 to p4, $R_1$ to $R_4$, and s1 to s4 are each independently an integer of 1 to 3, with the proviso that when any of them is 2 or greater, the corresponding linkers may be the same or different, x is an integer of 1 or 2, and y and z may be the same or different, and are each independently an integer of 0 to 3; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$, two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring,

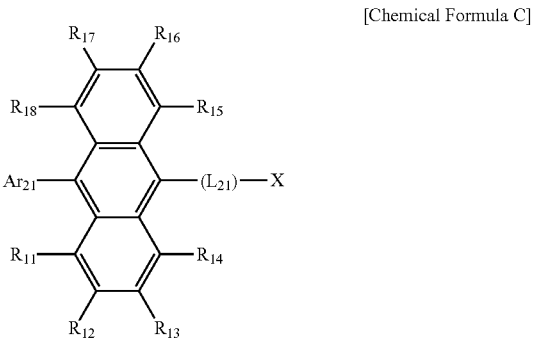

[Chemical Formula C]

wherein, $Ar_{21}$ is selected from among a substituted or unsubstituted aryl of 6 to 50 carbon atoms, and a substituted or unsubstituted heteroaryl of 3 to 50 carbon atoms containing O, N or S as a heteroatom:

$L_{21}$ is selected from among a substituted or unsubstituted arylene of 6 to 50 carbon atoms, and a substituted or unsubstituted heteroarylene of 3 to 50 carbon atoms containing O, N or S as a heteroatom;

R$_{11}$ and R$_{18}$ may be the same or different, and are each independently selected from the group consisting of hydrogen, deuterium, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 3 to 50 carbon atoms containing O, N or S as a heteroatom, a substituted or unsubstituted silicone, a substituted or unsubstituted boron, a substituted or unsubstituted silane, a carbonyl, a phosphoryl, an amino, a nitrile, a hydroxyl, a nitro, a halogen, an amide, and an ester;

R$_{12}$ and R$_{16}$ may form a saturated or unsaturated ring with R$_{13}$ and R$_{17}$, respectively X is a substituent represented by the following Structural Formula A,

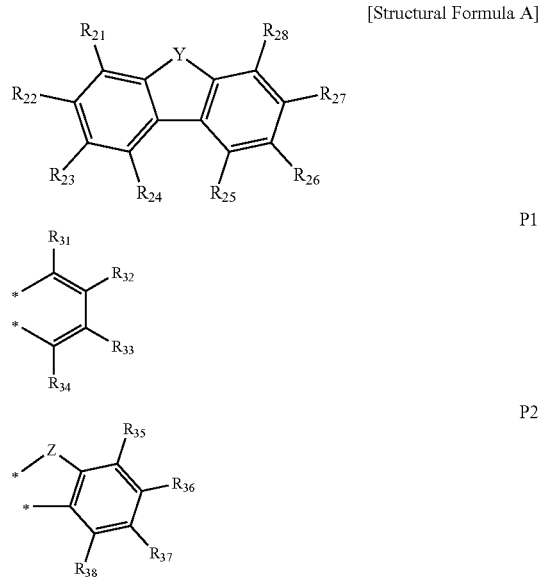

[Structural Formula A]

wherein,

Y and Z may be the same or different, and are each independently an oxygen atom or a sulfur atom, R$_{21}$ to R$_{38}$ may be the same or different, and are each independently selected from among a hydrogen atom, a deuterium atom, a substituted or unsubstituted alkyl of 1 to 30 carbon atoms, a substituted or unsubstituted cycloalkyl of 1 to 30 carbon atoms, a substituted or unsubstituted alkoxy of 1 to 30 carbon atoms, a substituted or unsubstituted aryl of 6 to 50 carbon atoms, a cyano, a halogen, and a silyl, two adjacent substituents of R$_{21}$ to R$_{24}$ occupy respective positions '*' of P1 or P2, and any one substituent of R$_{25}$ to R$_{28}$ represents a single bond connected to the linker L$_{21}$, wherein the term 'substituted' in the expression 'substituted or unsubstituted' for Chemical Formulas A, B and C means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 1 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms such as in "a substituted or unsubstituted alkyl of 1 to 30 carbon atoms", "a substituted or unsubstituted aryl of 6 to 50 carbon atoms", etc. means the total number of carbon atoms of, for example, the alkyl or aryl radical or moiety alone, exclusive of the number of carbon atoms of the substituent. For instance, a phenyl group with a butyl at the para position falls within the scope of an aryl of 6 carbon atoms although it is substituted with a butyl radical of 4 carbon atoms.

As used herein, the term "aryl" means an organic radical, derived from an aromatic hydrocarbon by removing one hydrogen atom. Further, the aromatic system may include a fused ring that is formed by adjacent substituents on the aryl radical.

Examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom of which may be substituted by a deuterium atom, a halogen atom, a hydroxy, a nitro, a cyano, a silyl, an amino (—NH$_2$, —NH(R), —N(R')(R'') wherein R' and R'' are each independently an alkyl of 1 to 10 alkyl, in this case called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms containing one to three heteroatoms selected from among N, O, P, Si, S, Ge, Se, and Te. In the aromatic system, two or more rings may be fused. One or more hydrogen atoms on the heteroaryl may be substituted by the same substituents as on the aryl.

As used herein, the term "heteroaromatic ring" refers to an aromatic hydrocarbon ring containing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atom of the silyl may be substituted by the same substituent as in the aryl.

As used herein, the expression "(the organic layer) . . . comprising at least one organic compound" is construed to mean that the organic layer may include one or two or more different compounds that fall within the scope of the present disclosure.

The amine compound represented by Chemical Formula A or B used in the organic light-emitting diode of the present disclosure is characterized by a structure in which the moiety of Chemical Formula $Q_1$ in Chemical Formula A is connected to the ring $A_1$ while an amine moiety containing both $Ar_1$ and $Ar_2$ is bonded to the ring $A_2$, or in which the moieties of Chemical Formulas $Q_2$ and $Q_1$ are respectively connected to the rings $A_1$ and $A_2$ while an amine moiety containing both $Ar_1$ and $Ar_2$ is bonded to the ring $A_2$.

In Chemical Formula A or B, A1, A2, E and F may be the same or different and are each independently a substituted or unsubstituted aromatic hydrocarbon ring of 6 to 50 carbon atoms.

When $A_1$, $A_2$, E, and F in Chemical Formula A or B may be the same or different and are each independently a substituted or unsubstituted aromatic hydrocarbon ring of 6 to 50 carbon atoms, the aromatic hydrocarbon ring moieties may each be independently any one selected from among [Structural Formula 10] to [Structural Formula 21].

wherein,

"—*" denotes a bonding site for forming a 5-membered ring containing the carbon atom connected to both the substituents $R_1$ and $R_2$, or a bonding site for forming a 5-membered ring containing M of the structural Formula $Q_1$ and $Q_2$ with moiety $A_1$ or $A_2$, when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring; and R's are the same as defined above for $R_1$ and $R_2$, m is an integer of 1 to 8, with the proviso that when m is 2 or greater or two or more R's exist, the corresponding R's may be the same or different.

In a particular embodiment, linkers $L_1$ to $L_{12}$ of Chemical Formulas A and B may each be a single bond, or any one selected from the following [Structural Formula 22] to [Structural Formula 30], p1 to p4, r1 to r4, and s1 to s4 may each be 1 or 2, and x may be 1:

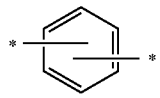

[Structural Formula 22]

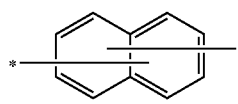

[Structural Formula 23]

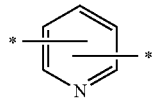

[Structural Formula 24]

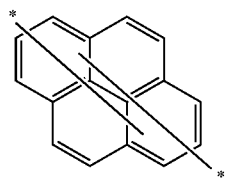

[Structural Formula 25]

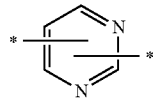

[Structural Formula 26]

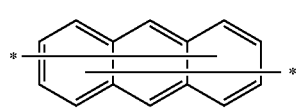

[Structural Formula 27]

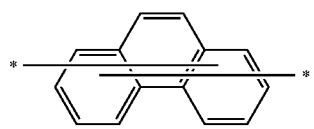

[Structural Formula 28]

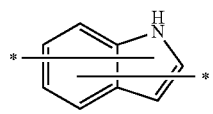

[Structural Formula 29]

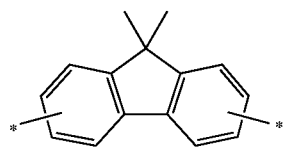

[Structural Formula 30]

In the linker, each of the unsubstituted carbon atoms of the aromatic ring moiety is bound with a hydrogen atom or a deuterium atom.

In this case, x and y may each be 1, and z may be 0 or 1.

The amine compound represented by Chemical Formula A or B, useful in the organic light-emitting diode of the present disclosure, may be selected from compounds represented by the following [Chemical Formula 1] to [Chemical Formula 239], but is not limited thereto.

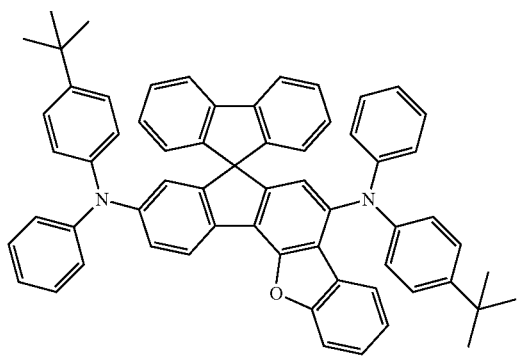

<Chemical Formula 1>

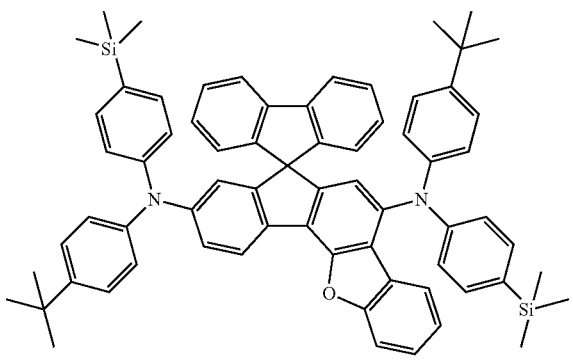

<Chemical Formula 2>

-continued
<Chemical Formula 3>
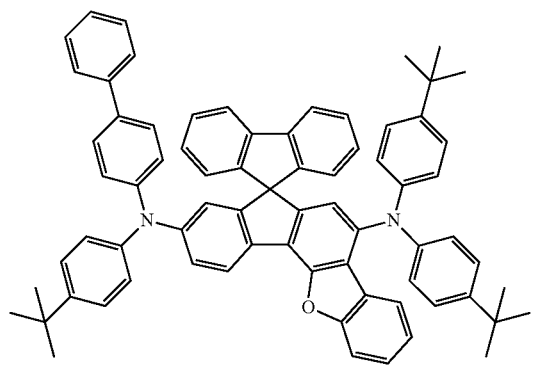
<Chemical Formula 4>
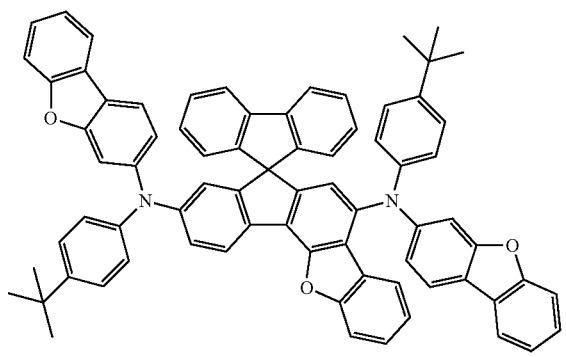
<Chemical Formula 5>
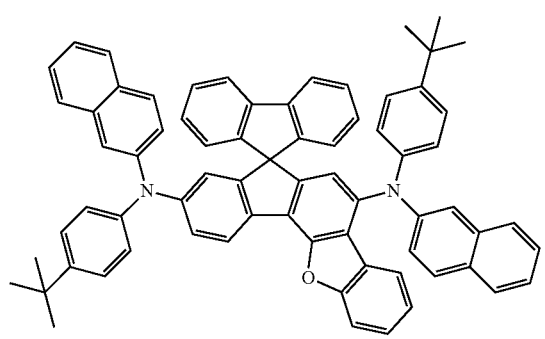
<Chemical Formula 6>
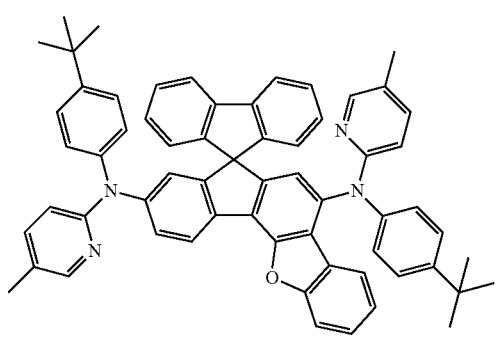
<Chemical Formula 7>
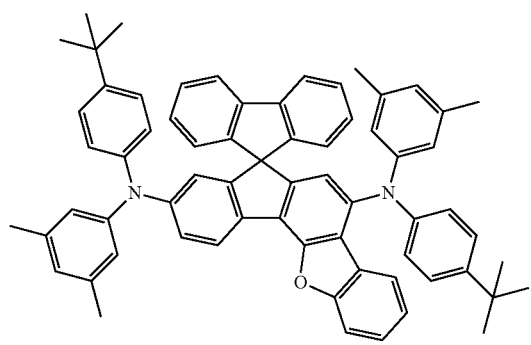
<Chemical Formula 8>
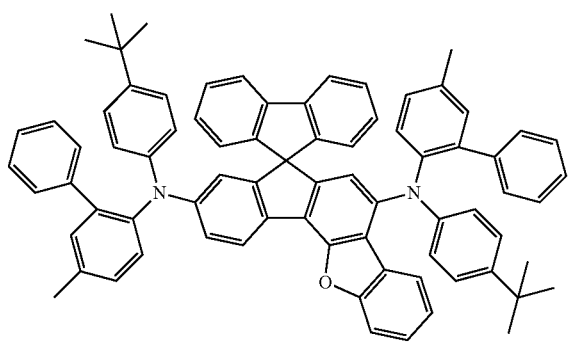
<Chemical Formula 9>
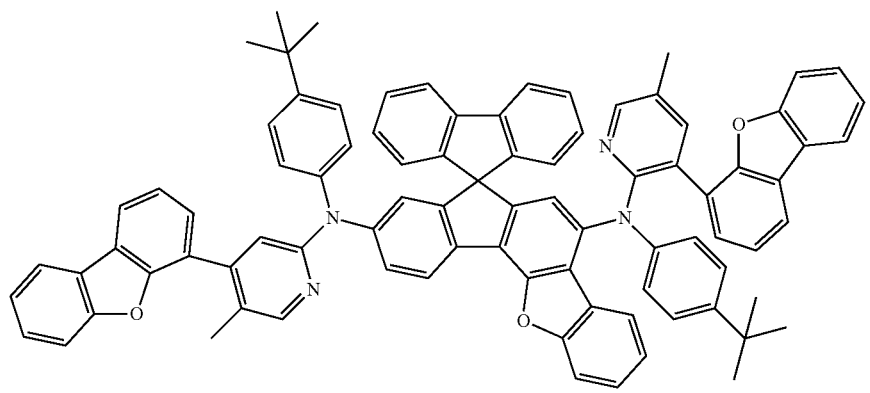

<Chemical Formula 10>
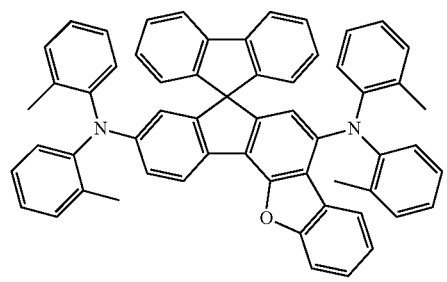
<Chemical Formula 11>
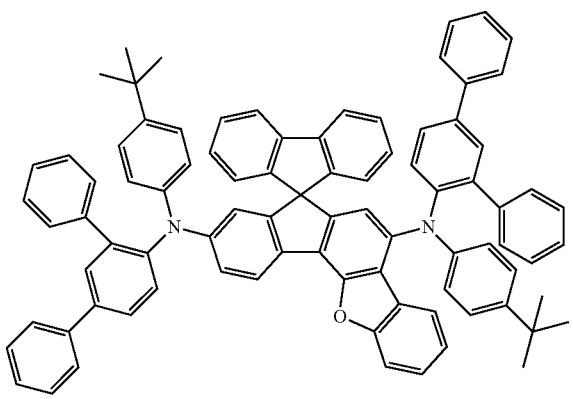
<Chemical Formula 12>
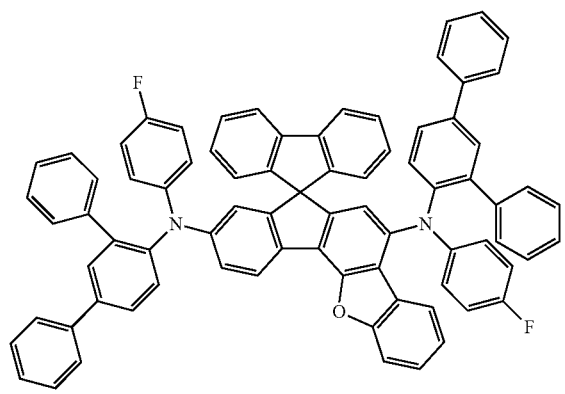
<Chemical Formula 13>
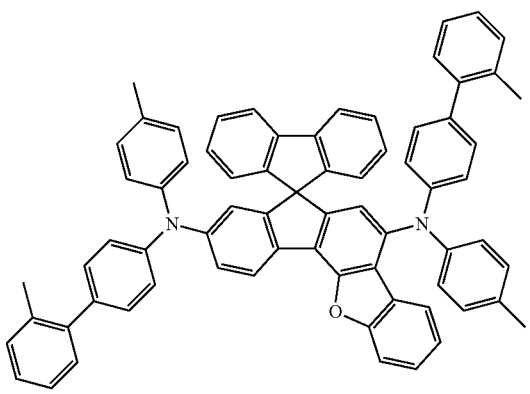
<Chemical Formula 14>
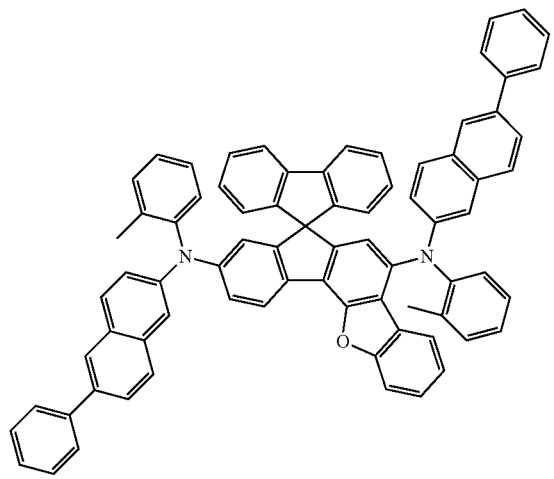
<Chemical Formula 15>
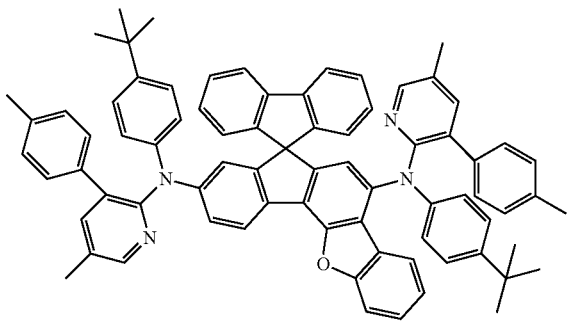

-continued
<Chemical Formula 16>
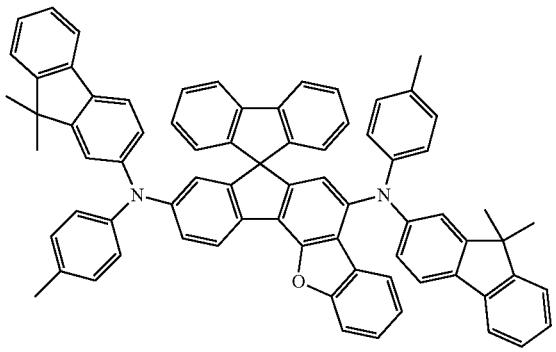
<Chemical Formula 17>
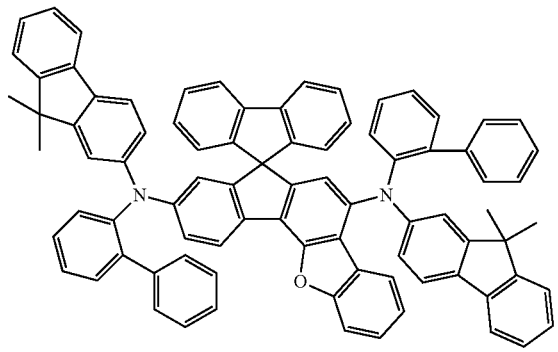
<Chemical Formula 18>
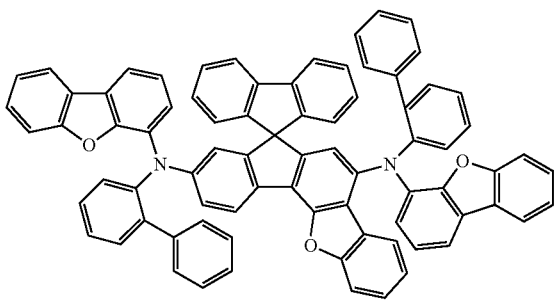
<Chemical Formula 19>
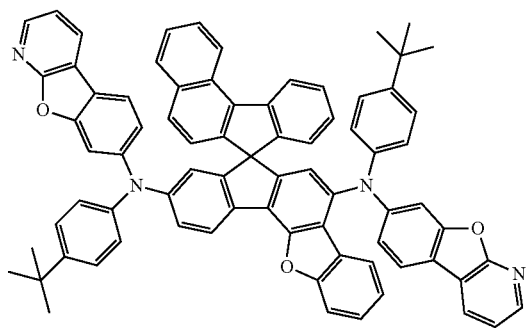
<Chemical Formula 20>
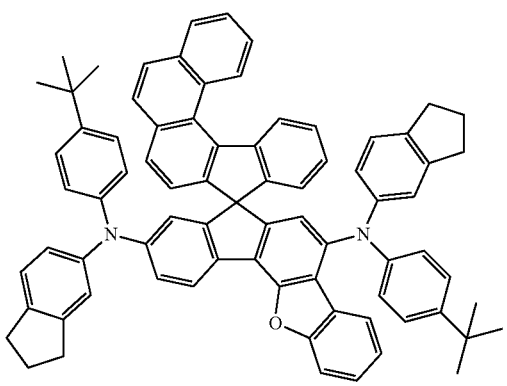
<Chemical Formula 21>
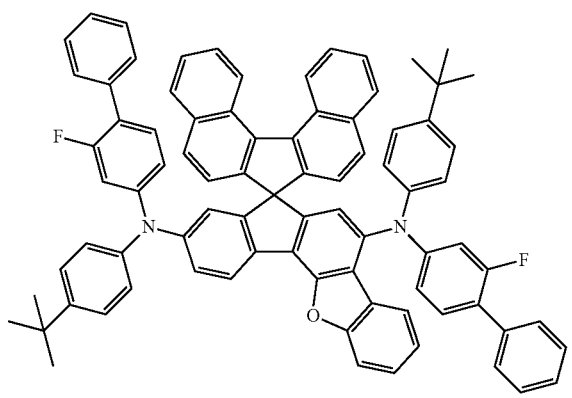
<Chemical Formula 22>
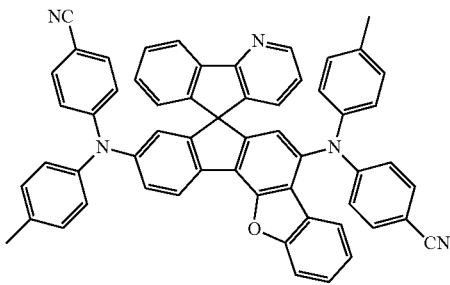
<Chemical Formula 23>
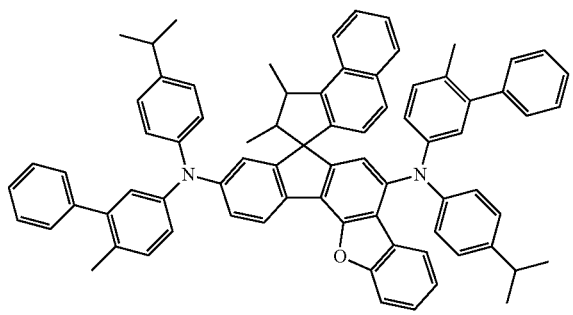

-continued
<Chemical Formula 24>
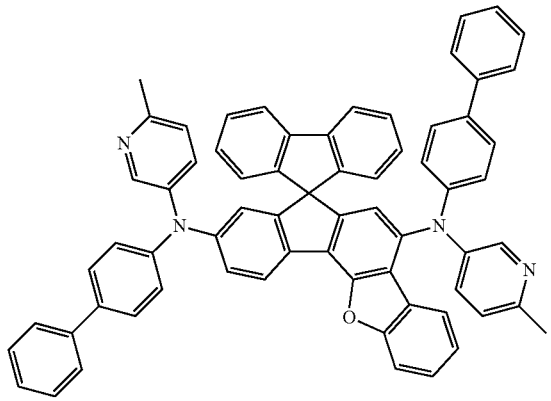
<Chemical Formula 25>
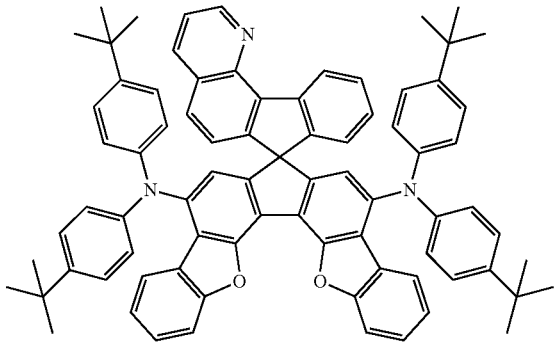
<Chemical Formula 26>
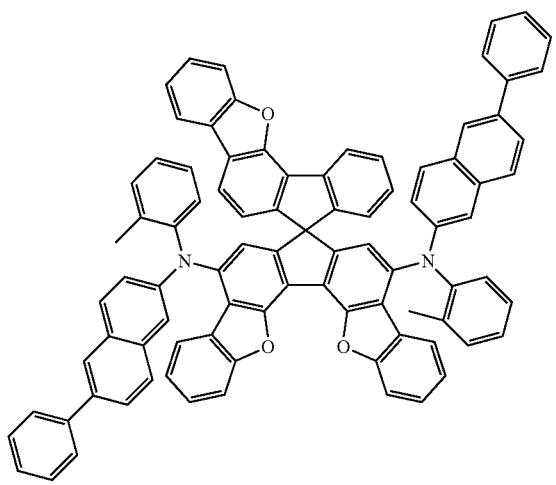
<Chemical Formula 27>
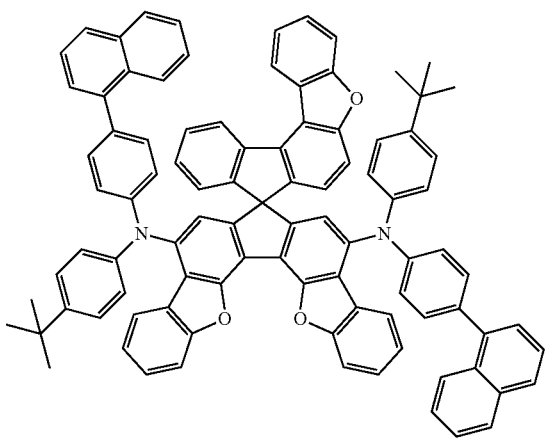
<Chemical Formula 28>
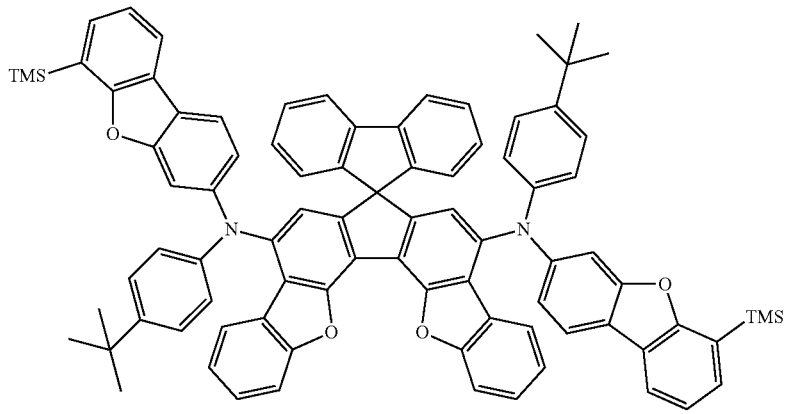
<Chemical Formula 29>
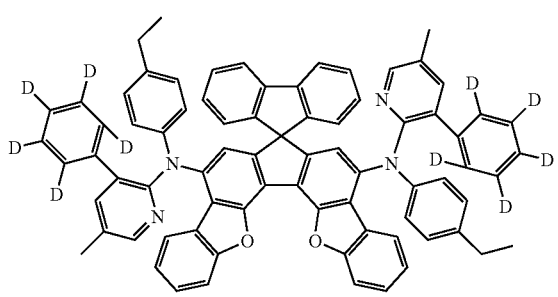
<Chemical Formula 30>
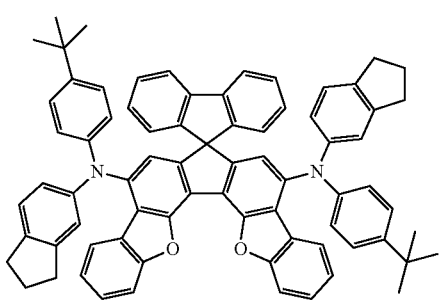

<Chemical Formula 31>
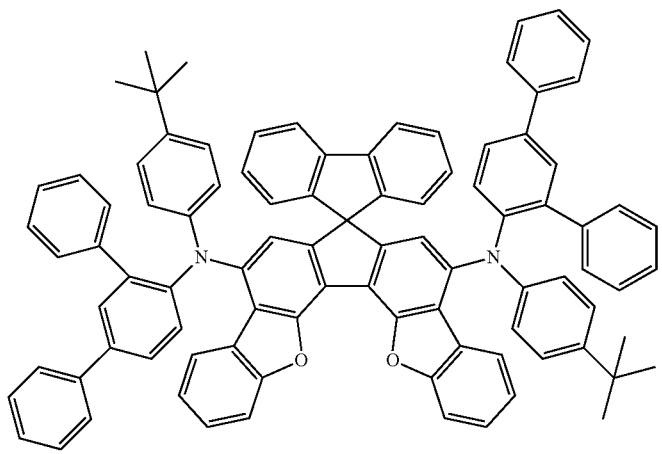
<Chemical Formula 32>
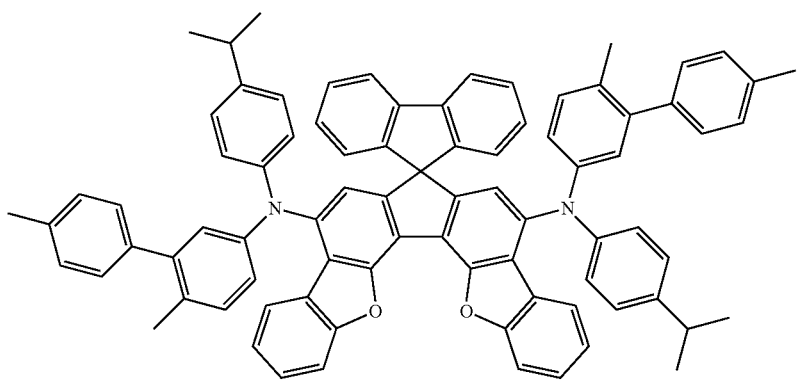
<Chemical Formula 33>
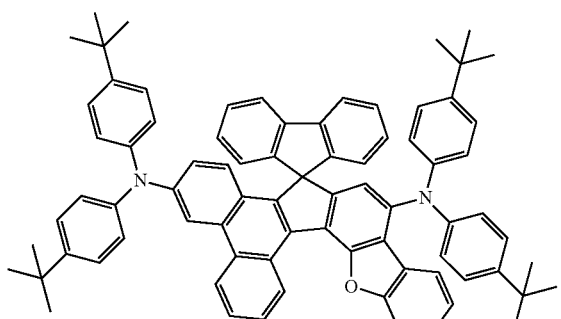
<Chemical Formula 34>
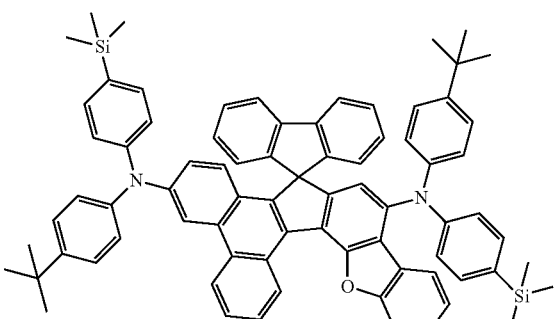
<Chemical Formula 35>
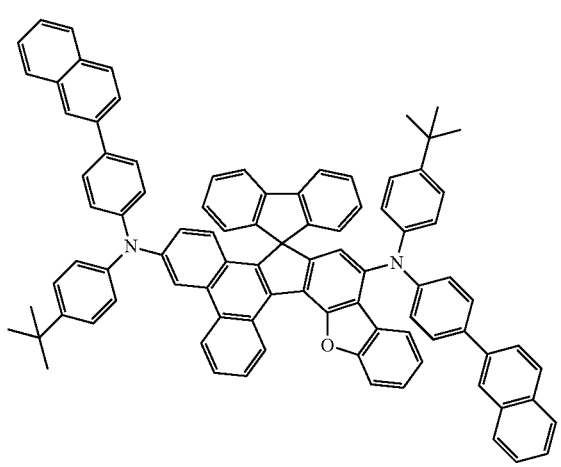
<Chemical Formula 36>
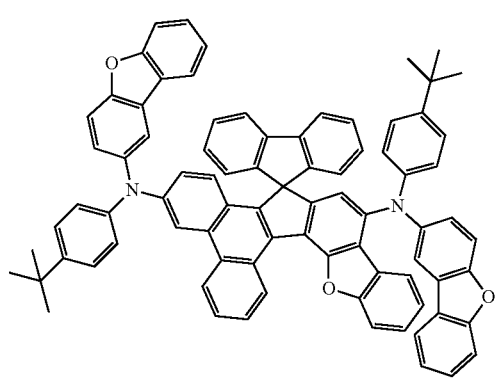

-continued
<Chemical Formula 37>
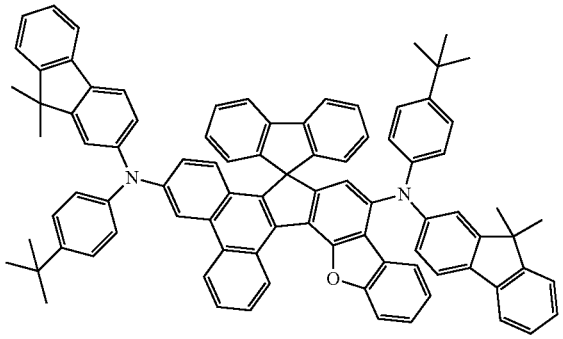
<Chemical Formula 38>
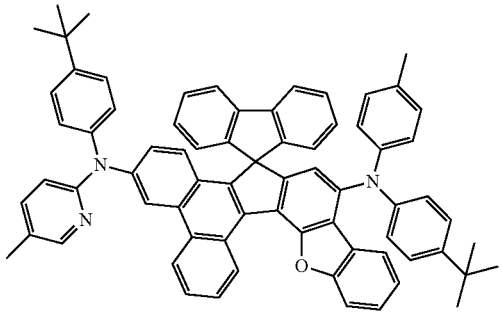
<Chemical Formula 39>
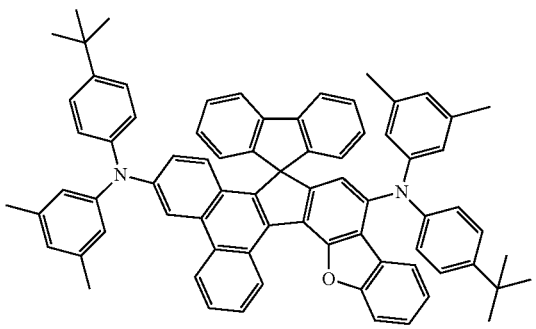
<Chemical Formula 40>
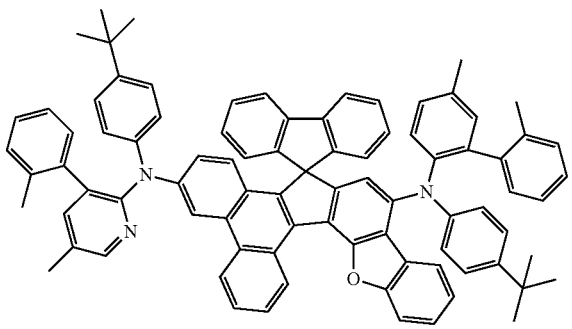
<Chemical Formula 41>
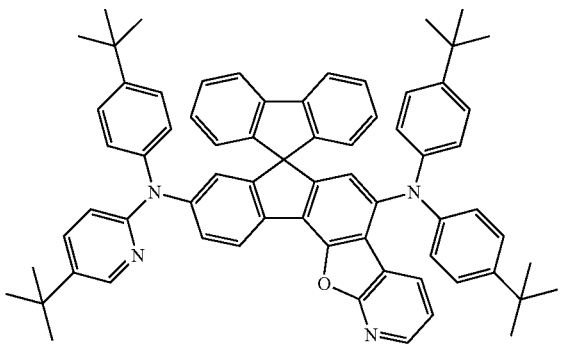
<Chemical Formula 42>
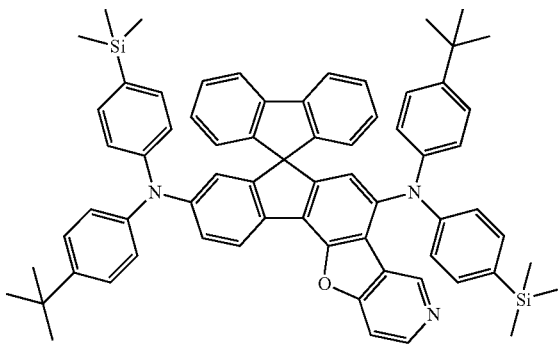
<Chemical Formula 43>
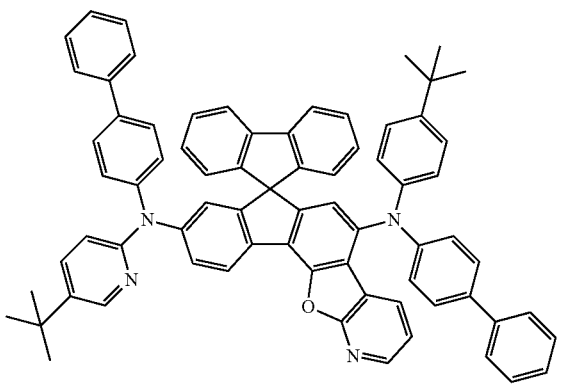
<Chemical Formula 44>
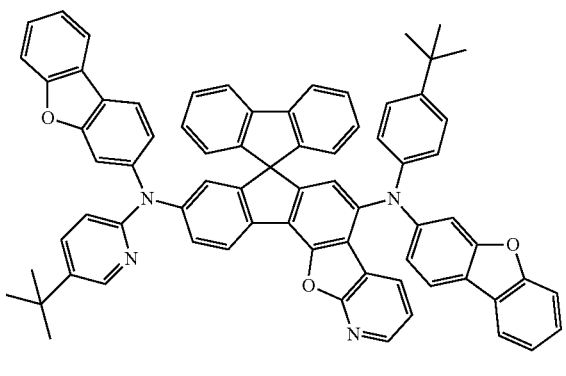

<Chemical Formula 45>
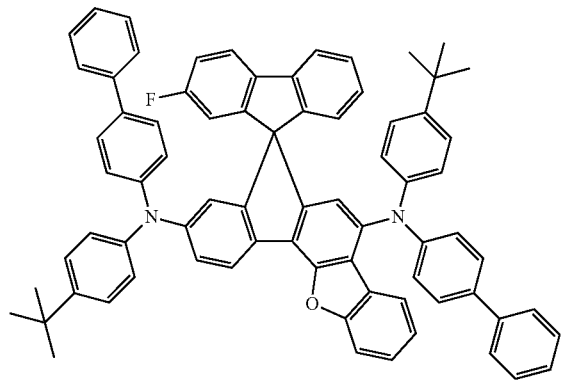
<Chemical Formula 46>
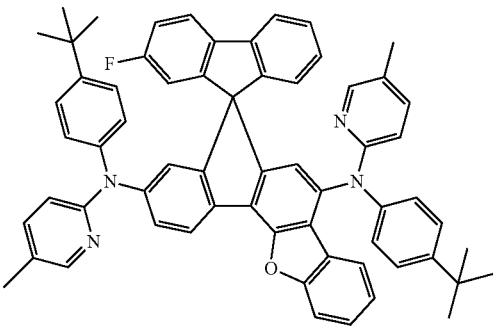
<Chemical Formula 47>
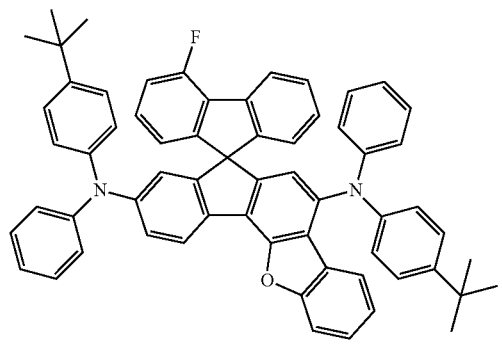
<Chemical Formula 48>
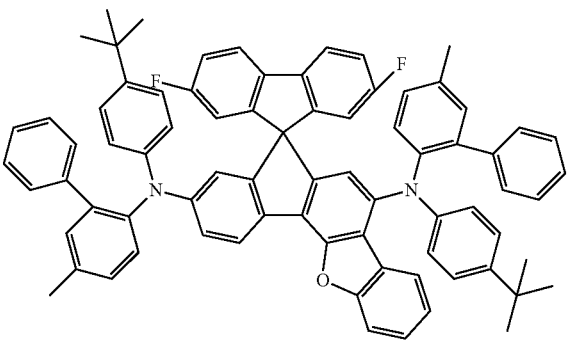
<Chemical Formula 49>
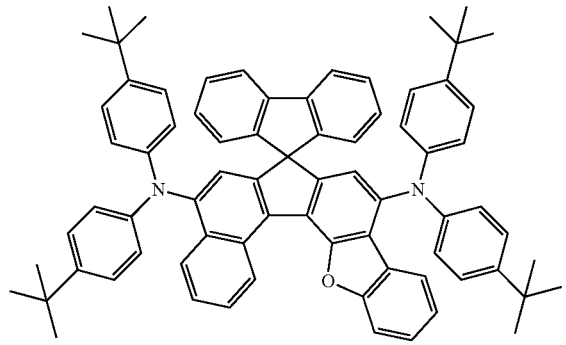
<Chemical Formula 50>
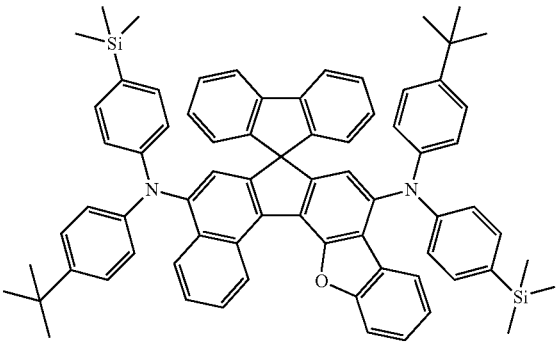
<Chemical Formula 51>
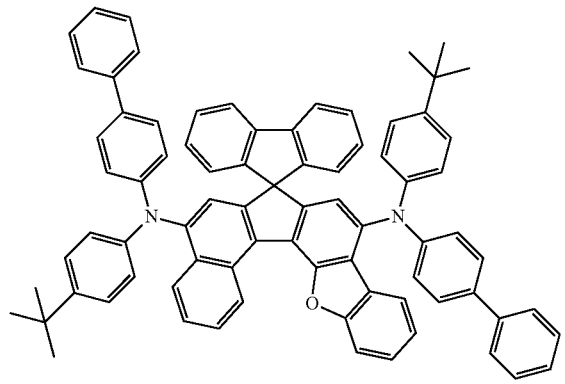
<Chemical Formula 52>
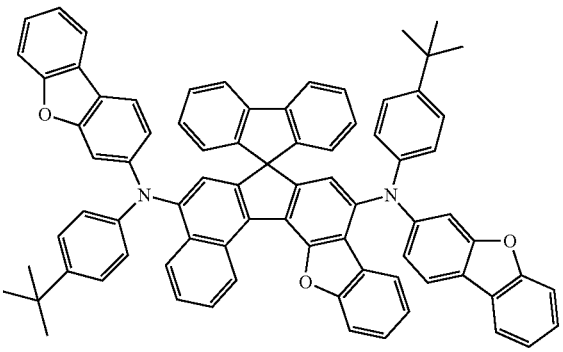

-continued
<Chemical Formula 53>
<Chemical Formula 54>
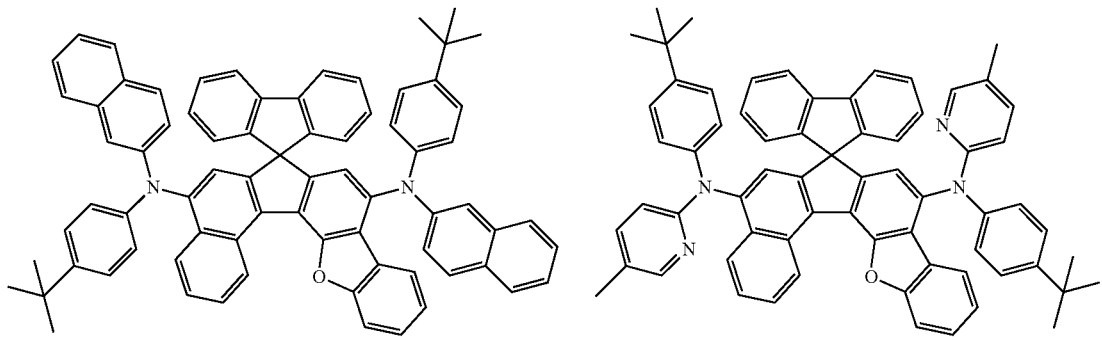
<Chemical Formula 55>
<Chemical Formula 56>
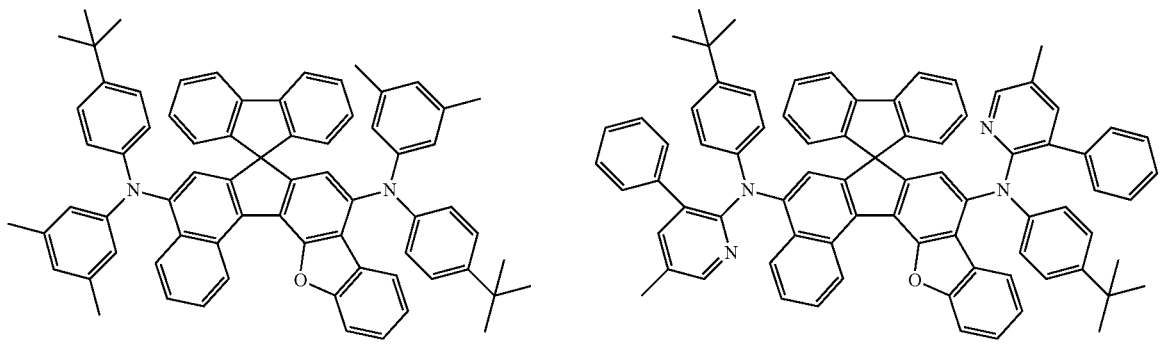
<Chemical Formula 57>
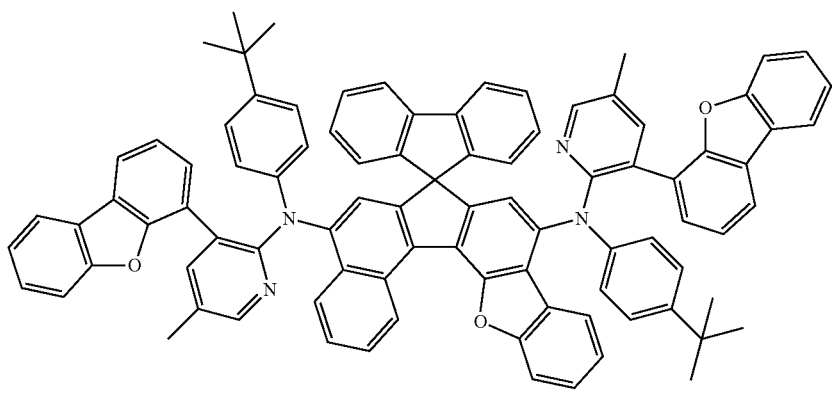
<Chemical Formula 58>
<Chemical Formula 59>
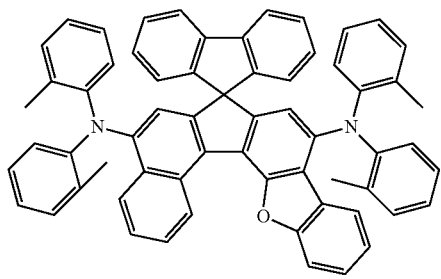
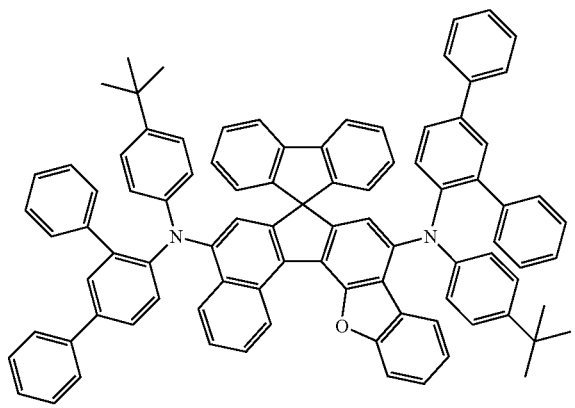

-continued
<Chemical Formula 60>
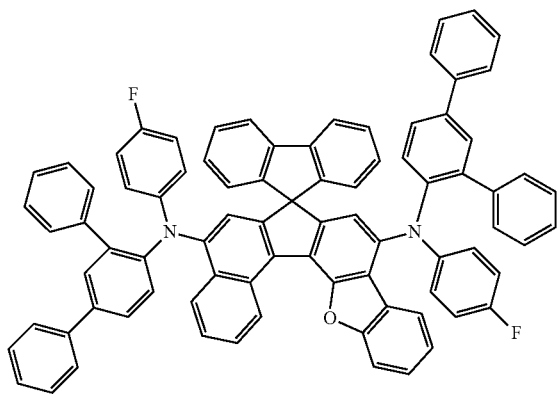
<Chemical Formula 61>
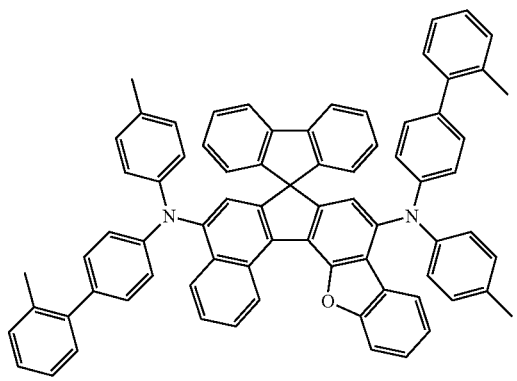
<Chemical Formula 62>
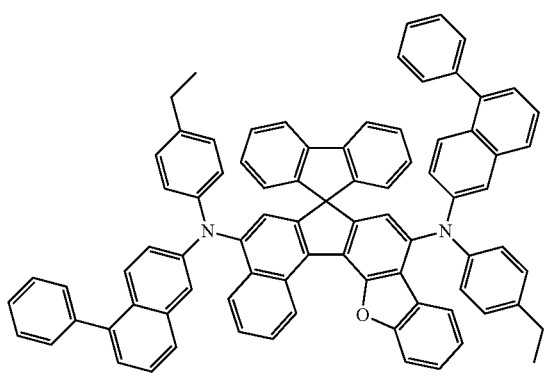
<Chemical Formula 63>
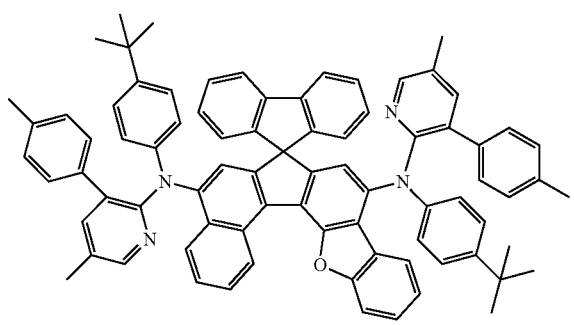
<Chemical Formula 64>
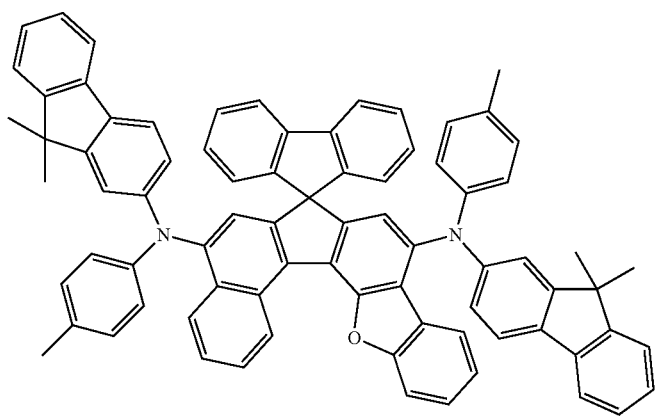

<Chemical Formula 65>
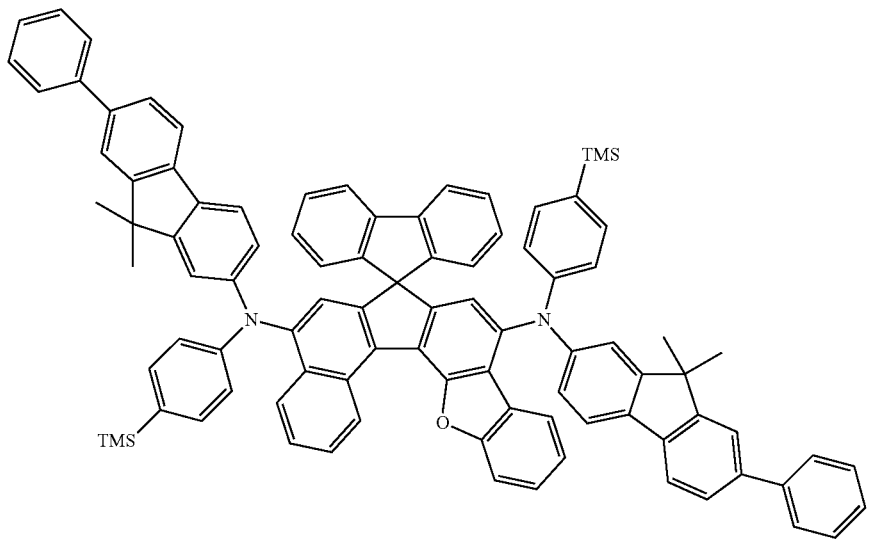
<Chemical Formula 66>                <Chemical Formula 67>
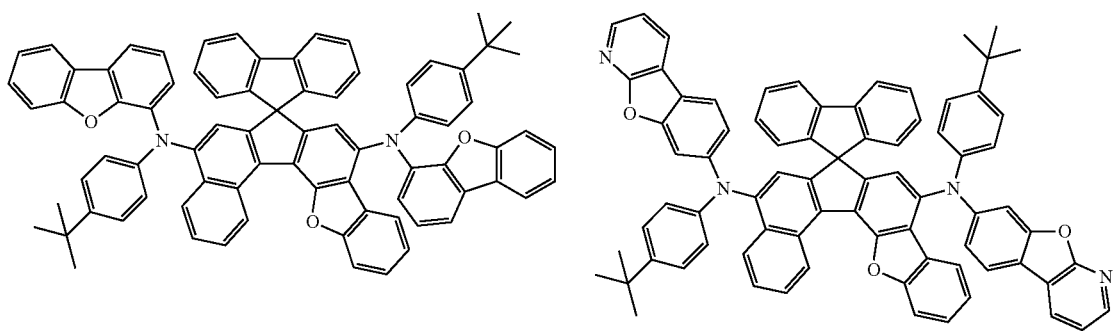
<Chemical Formula 68>                <Chemical Formula 69>
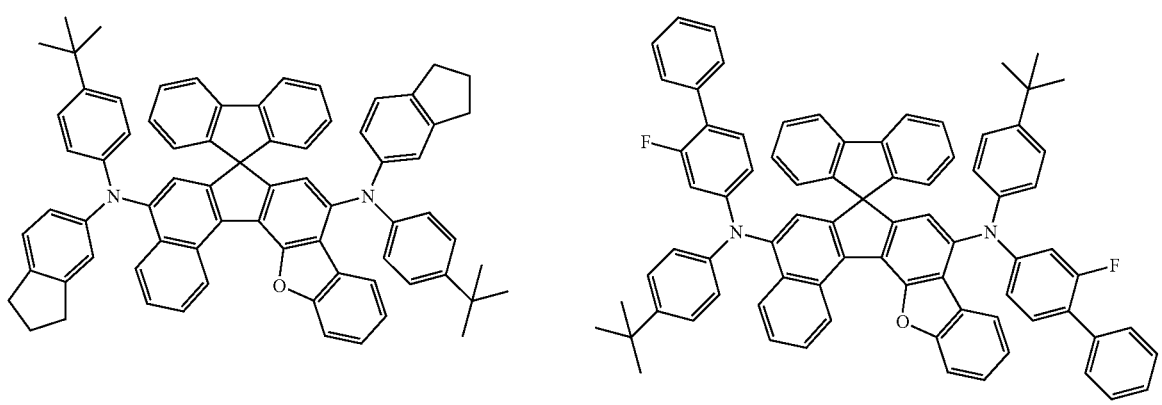
<Chemical Formula 70>                <Chemical Formula 71>
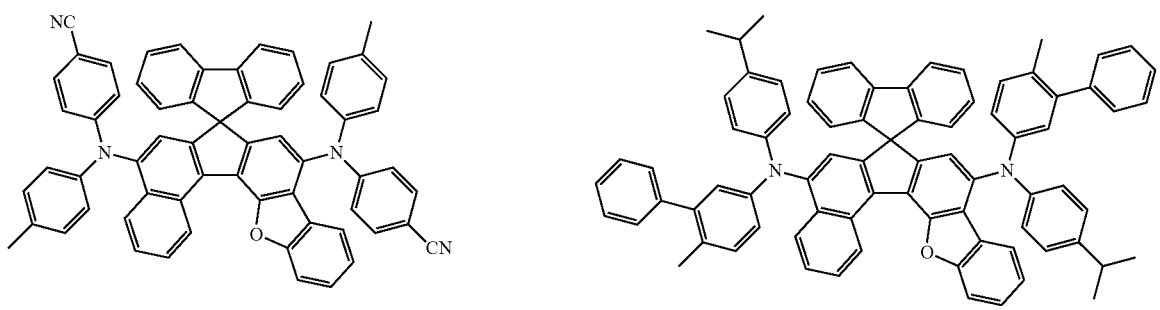

-continued
<Chemical Formula 72>
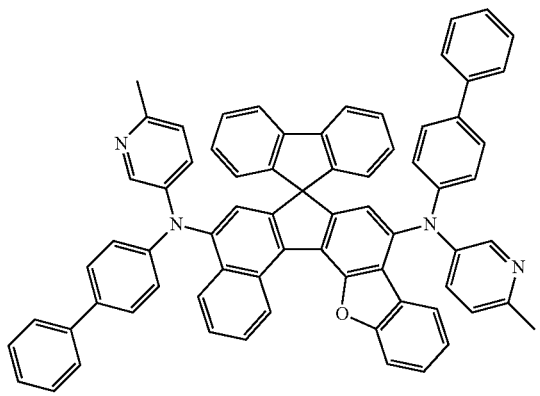
<Chemical Formula 73>
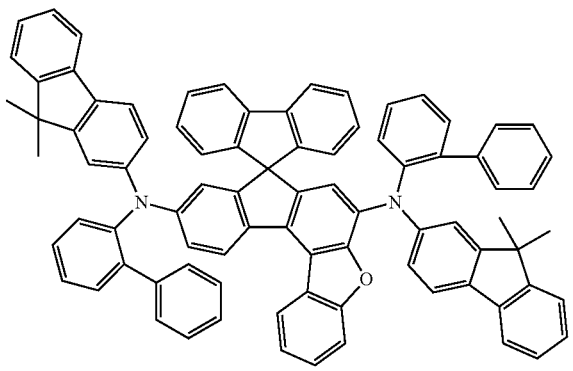
<Chemical Formula 74>
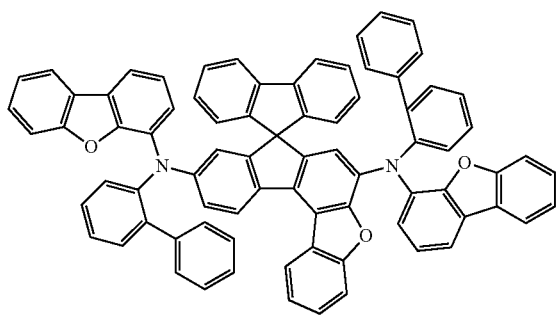
<Chemical Formula 75>
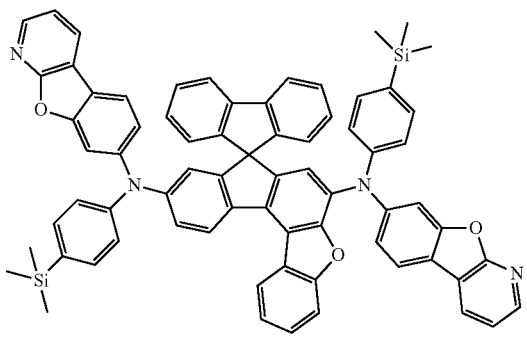
<Chemical Formula 76>
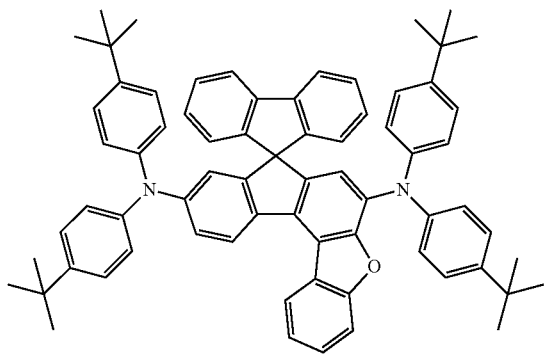
<Chemical Formula 77>
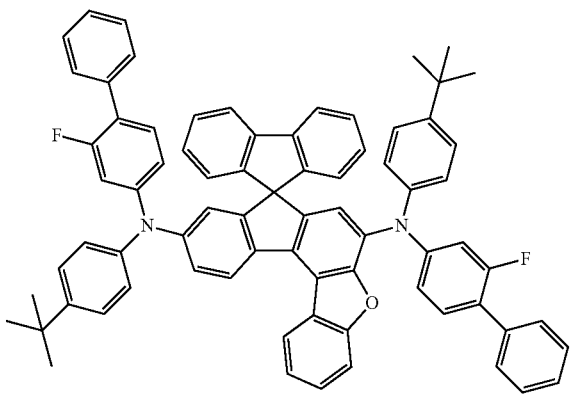
<Chemical Formula 78>
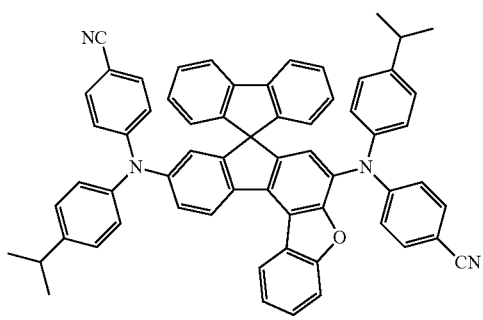
<Chemical Formula 79>
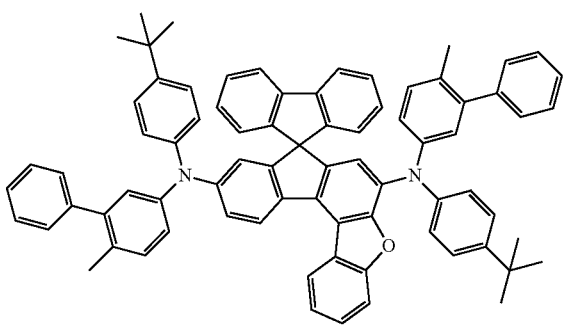

-continued
<Chemical Formula 80>
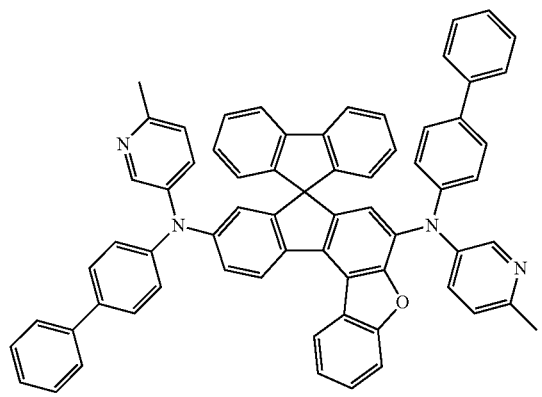
<Chemical Formula 81>
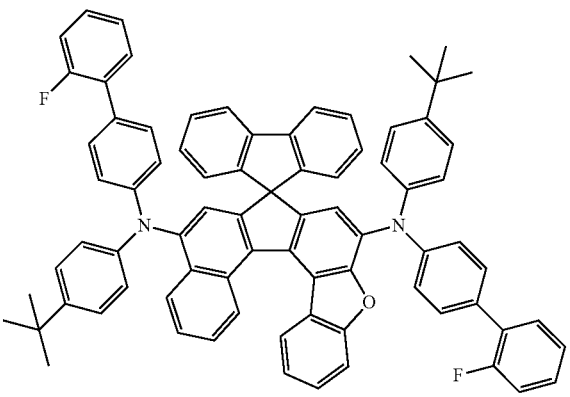
<Chemical Formula 82>
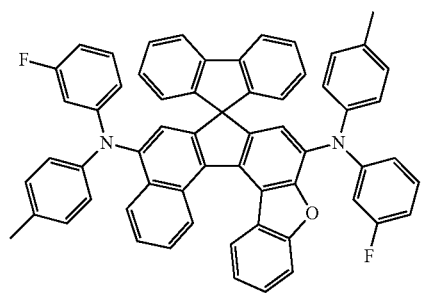
<Chemical Formula 83>
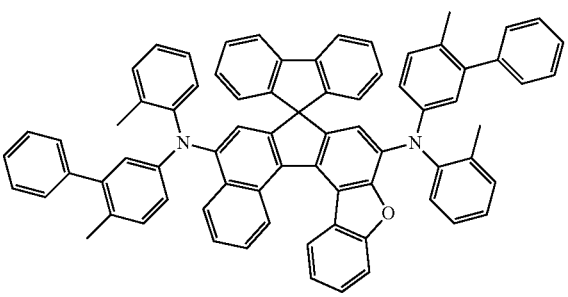
<Chemical Formula 84>
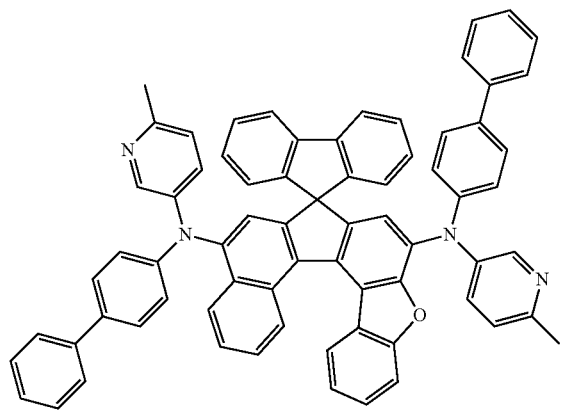
<Chemical Formula 85>
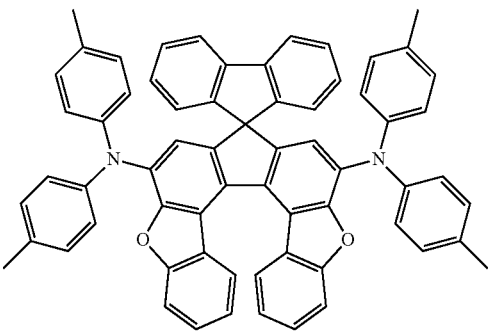
<Chemical Formula 86>
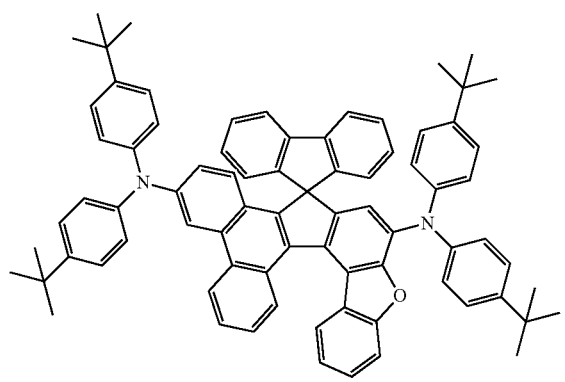
<Chemical Formula 87>
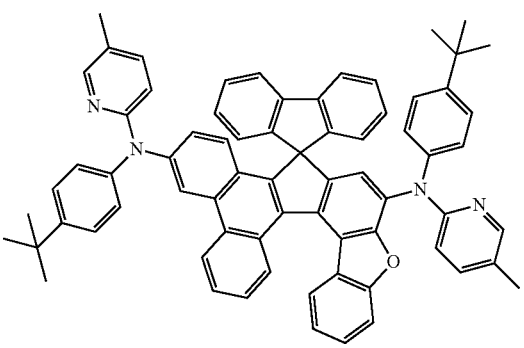

-continued
<Chemical Formula 88>
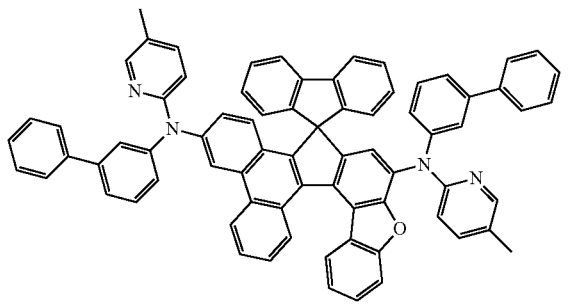
<Chemical Formula 89>
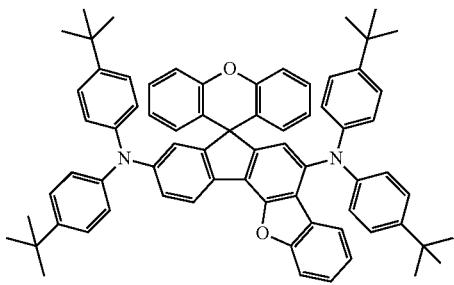
<Chemical Formula 90>
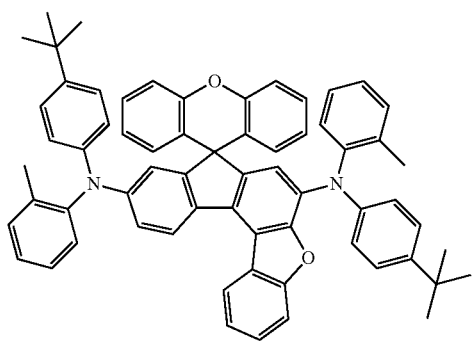
<Chemical Formula 91>
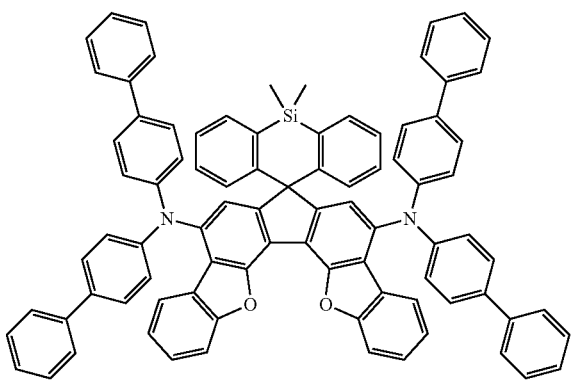
<Chemical Formula 92>
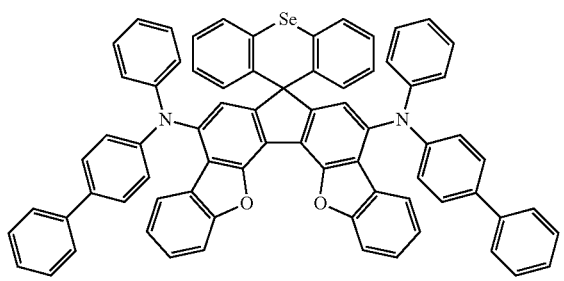
<Chemical Formula 93>
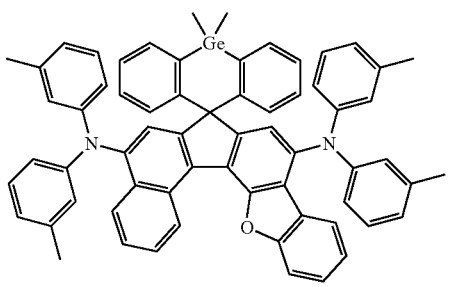
<Chemical Formula 94>
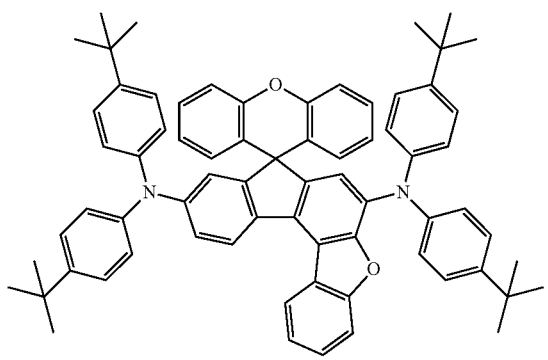
<Chemical Formula 95>
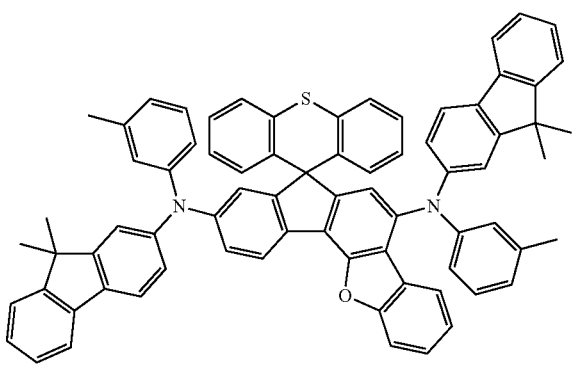

-continued
<Chemical Formula 96>
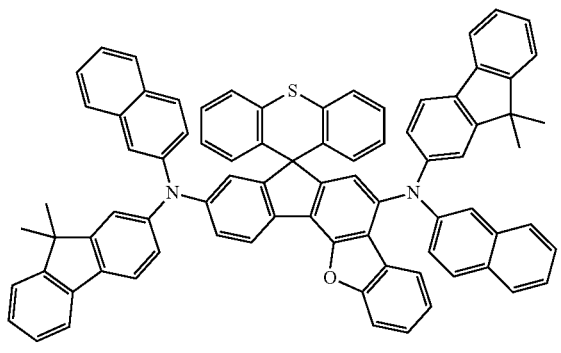
<Chemical Formula 97>
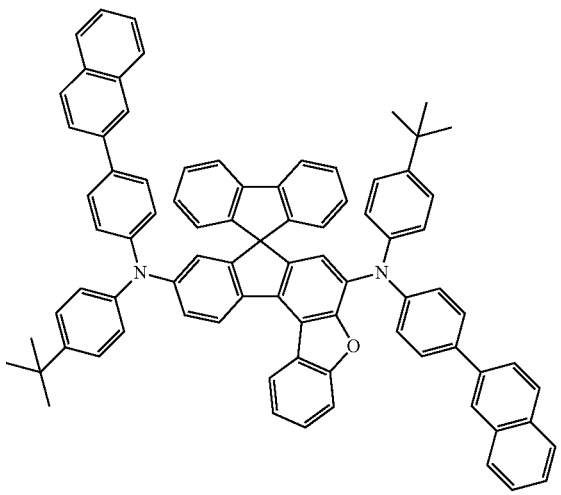
<Chemical Formula 98>
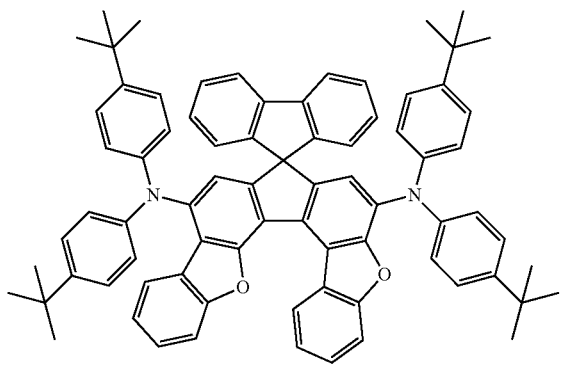
<Chemical Formula 99>
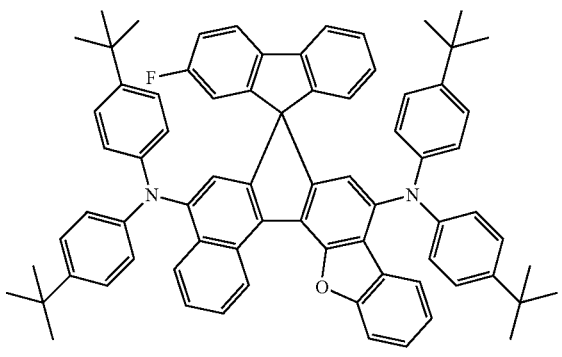
<Chemical Formula 100>
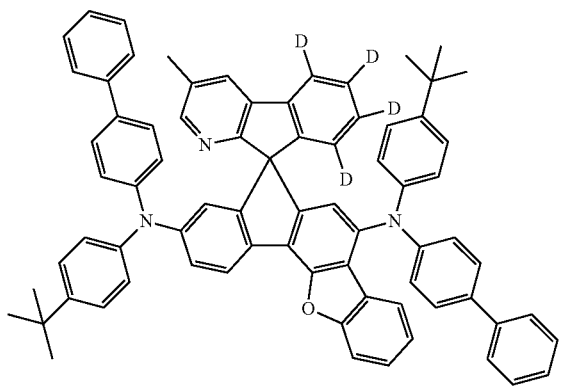
<Chemical Formula 101>
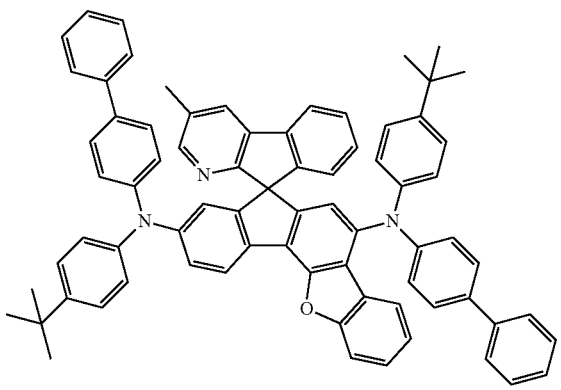

-continued
<Chemical Formula 102>
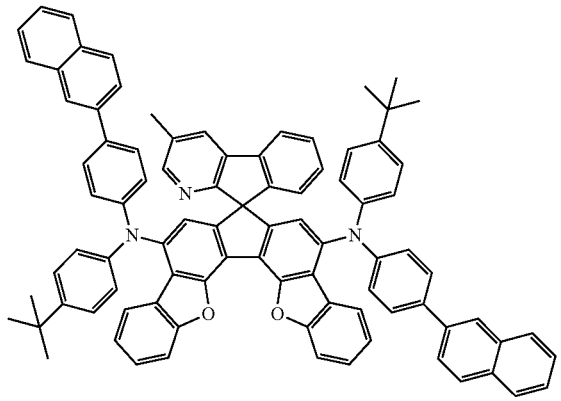
<Chemical Formula 103>
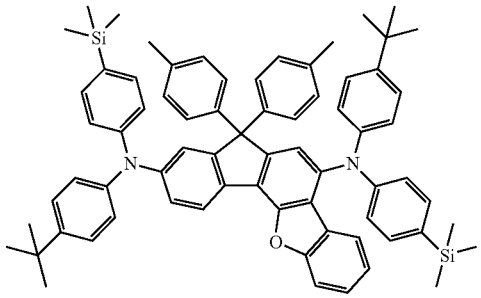
<Chemical Formula 104>
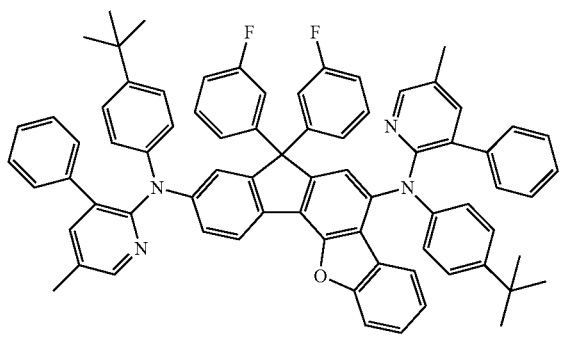
<Chemical Formula 105>
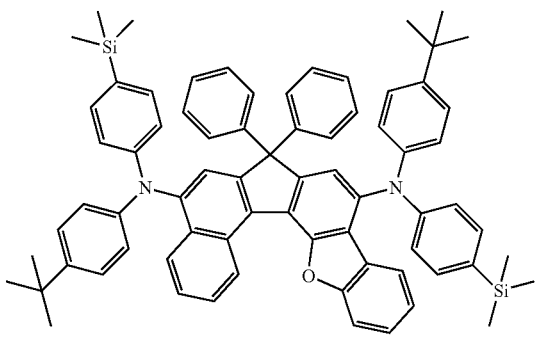
<Chemical Formula 106>
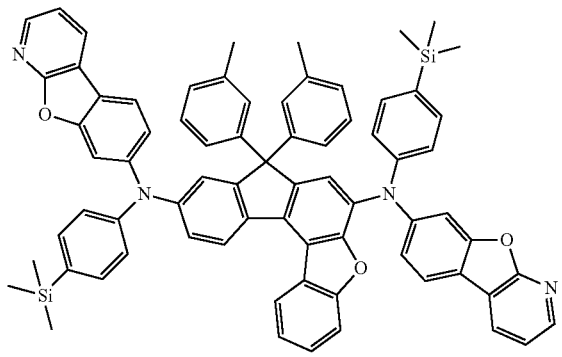
<Chemical Formula 107>
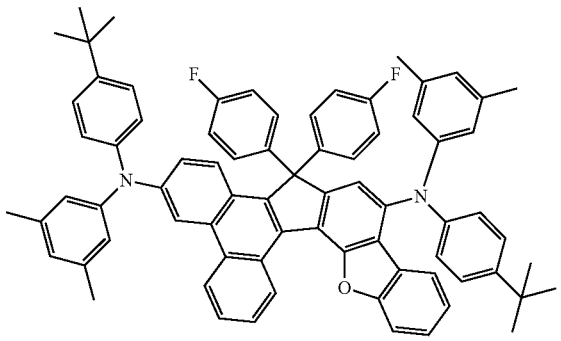
<Chemical Formula 108>
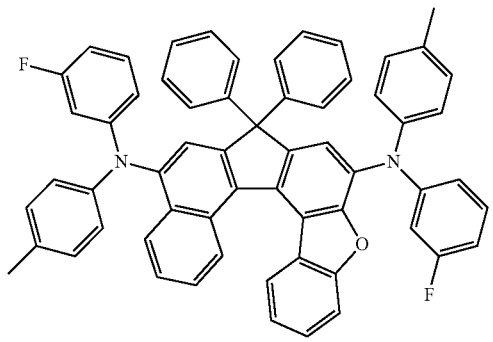
<Chemical Formula 109>
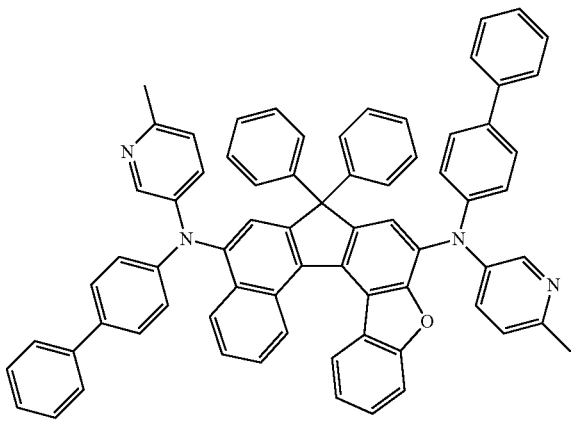

<Chemical Formula 110>
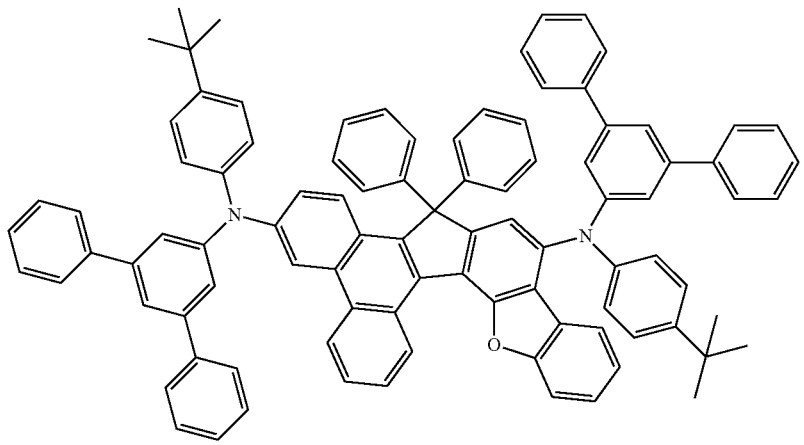
<Chemical Formula 111>
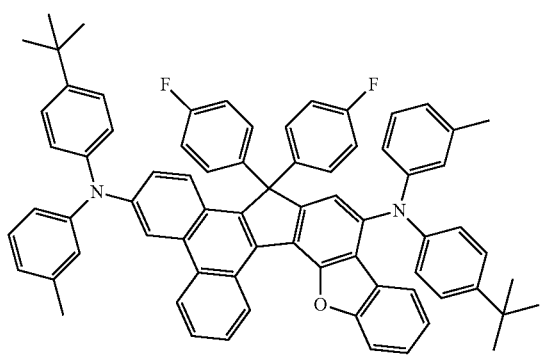
<Chemical Formula 112>
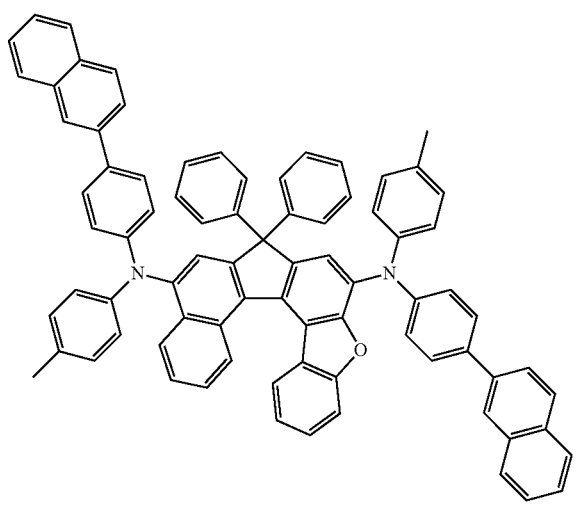
<Chemical Formula 113>
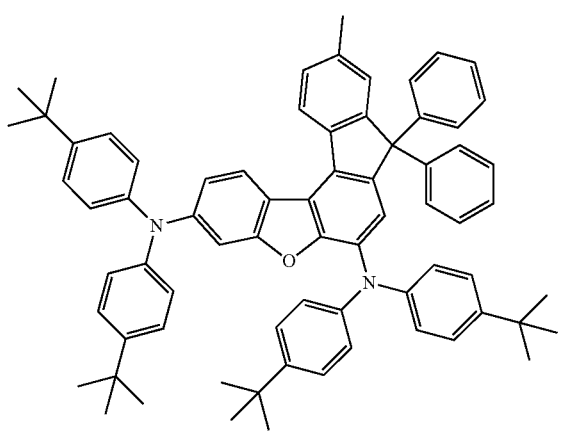
<Chemical Formula 114>
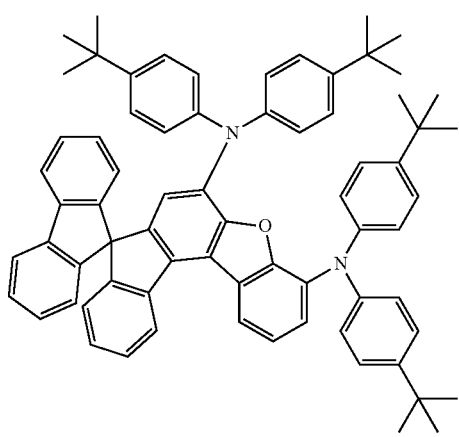

<Chemical Formula 115>
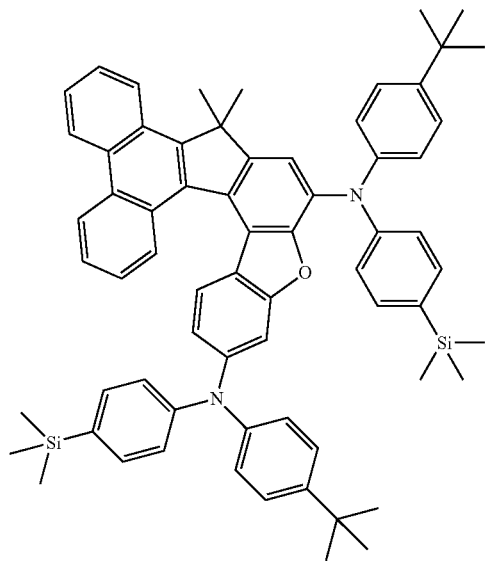
<Chemical Formula 116>
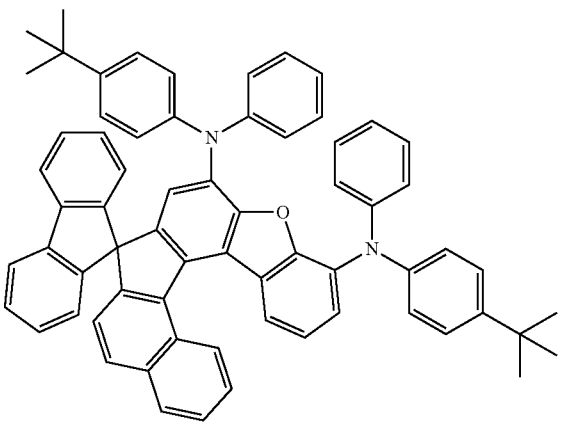
<Chemical Formula 117>
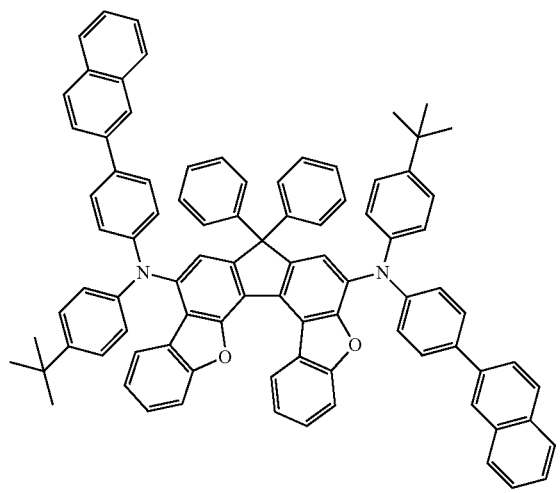
<Chemical Formula 118>
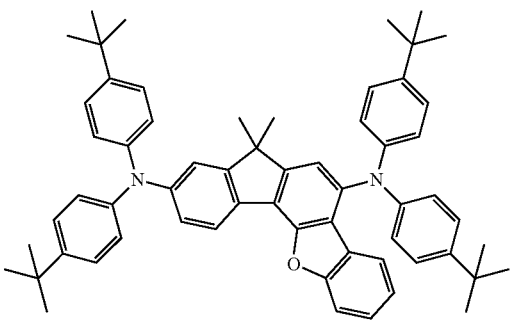
<Chemical Formula 119>
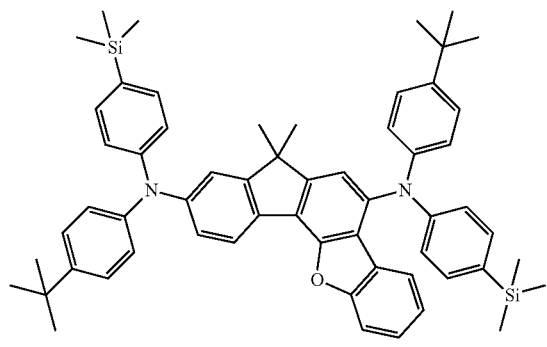
<Chemical Formula 120>
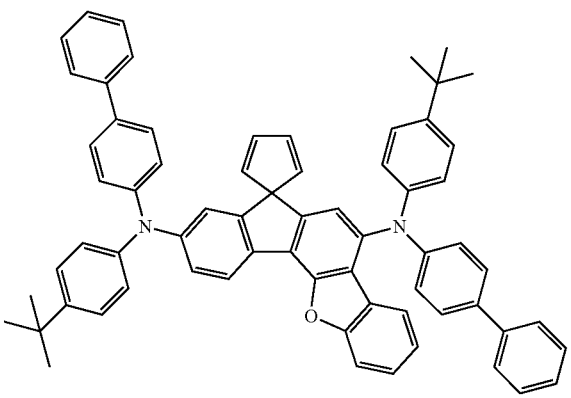

-continued
<Chemical Formula 121>
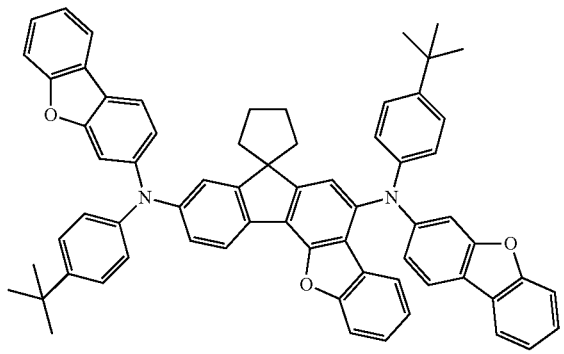
<Chemical Formula 122>
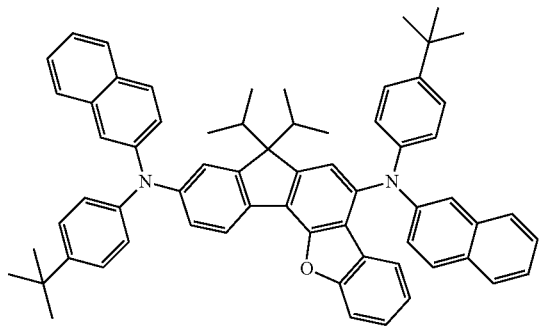
<Chemical Formula 123>
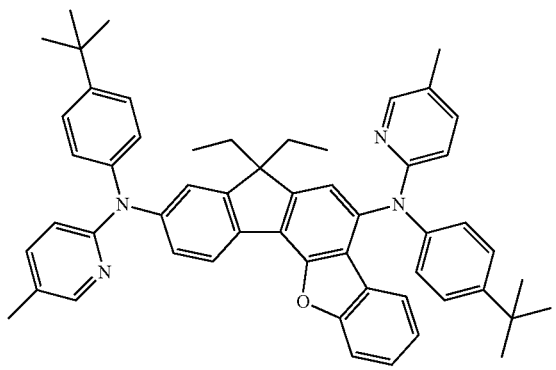
<Chemical Formula 124>
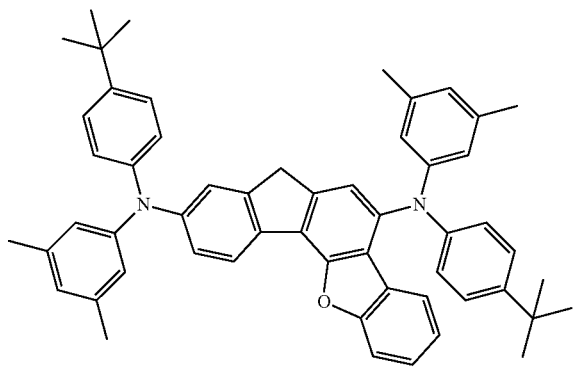
<Chemical Formula 125>
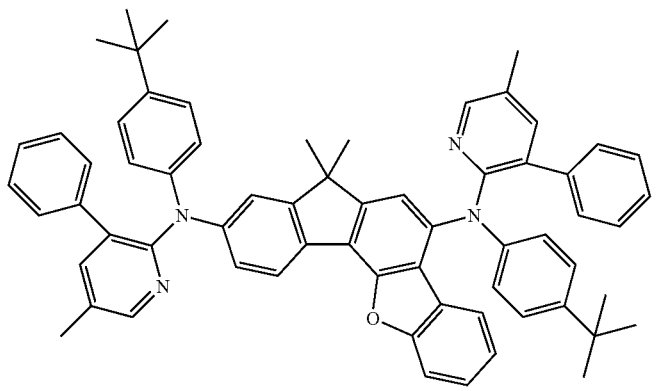
<Chemical Formula 126>
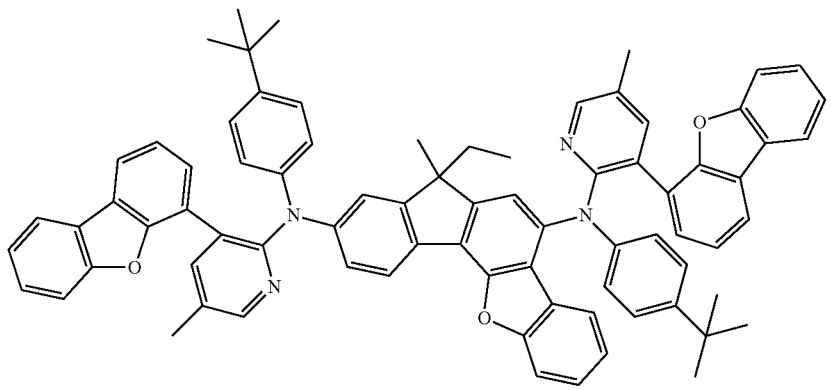

-continued
<Chemical Formula 127>
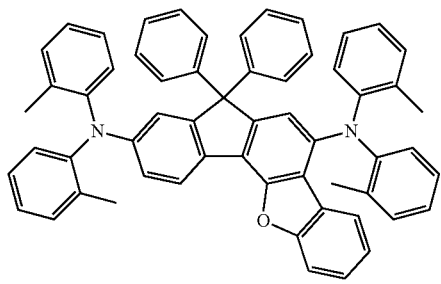
<Chemical Formula 128>
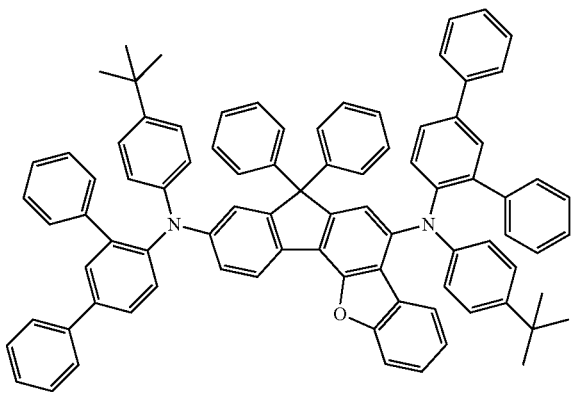
<Chemical Formula 129>
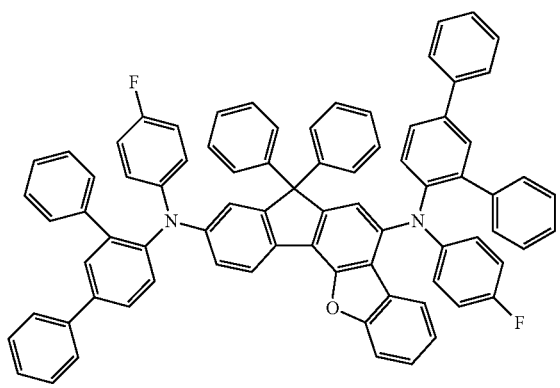
<Chemical Formula 130>
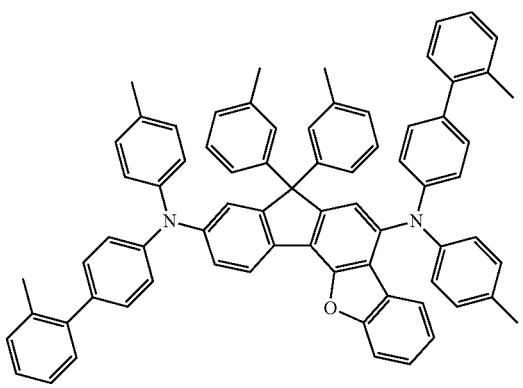
<Chemical Formula 131>
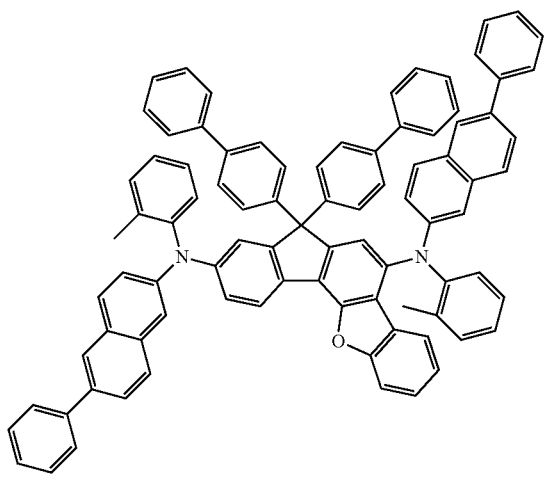
<Chemical Formula 132>
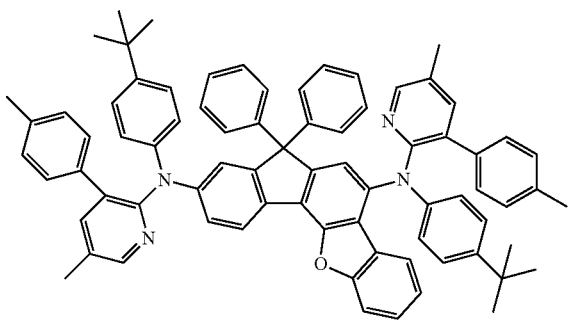

<Chemical Formula 133>
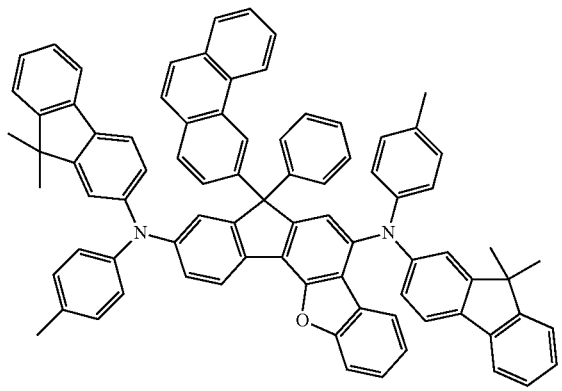
<Chemical Formula 134>
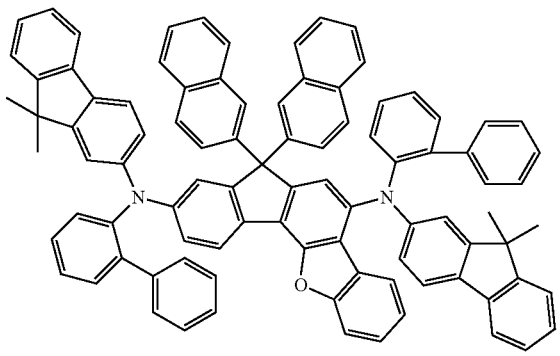
<Chemical Formula 135>
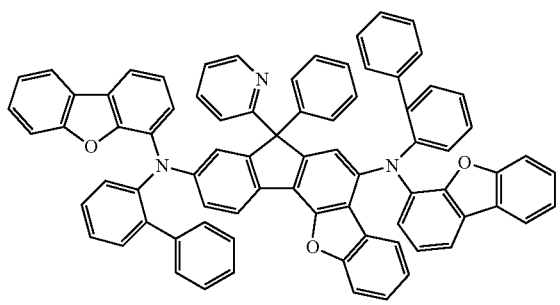
<Chemical Formula 136>
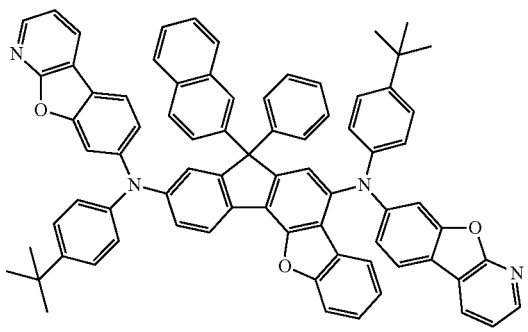
<Chemical Formula 137>
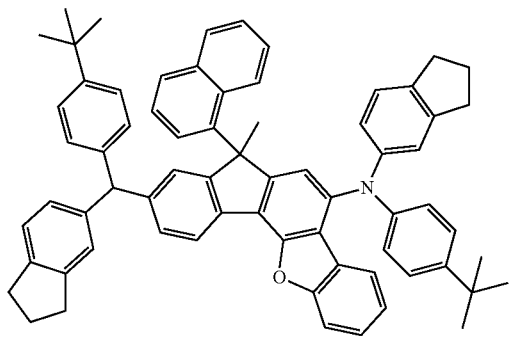
<Chemical Formula 138>
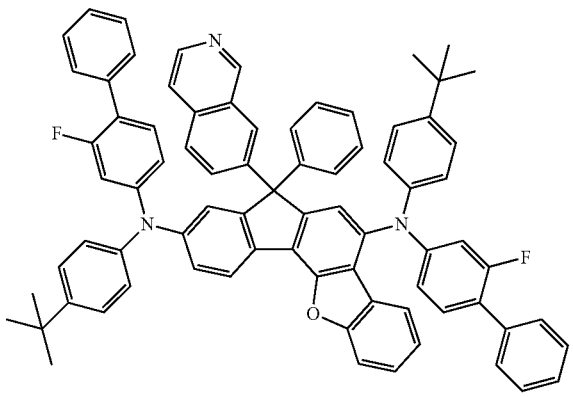
<Chemical Formula 139>
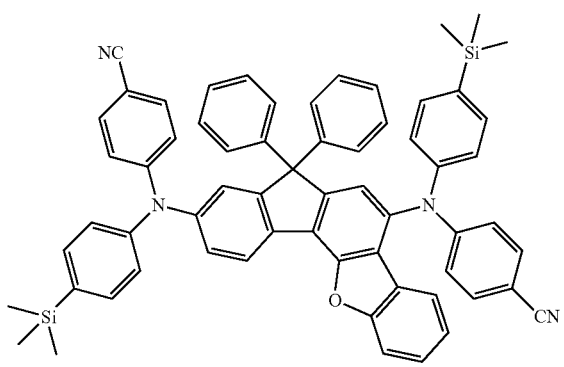
<Chemical Formula 140>
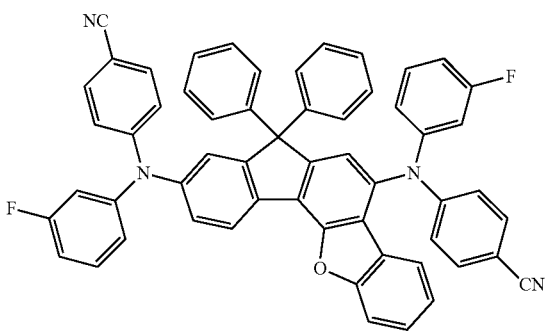

-continued
<Chemical Formula 141>
<Chemical Formula 142>
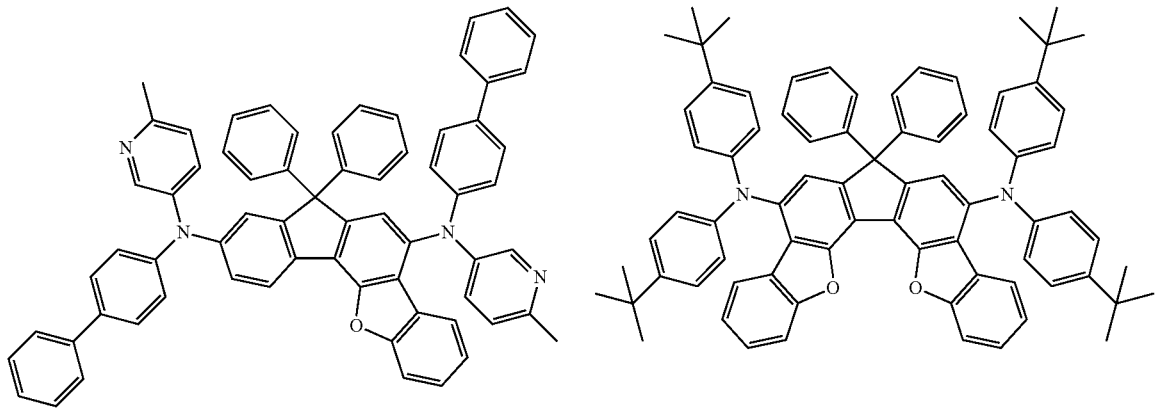
<Chemical Formula 143>
<Chemical Formula 144>
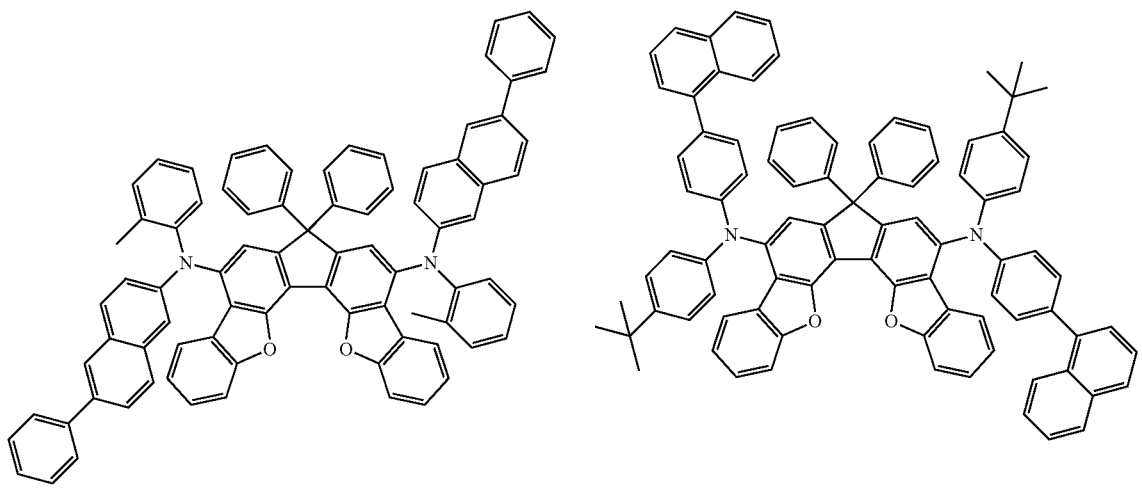
<Chemical Formula 145>
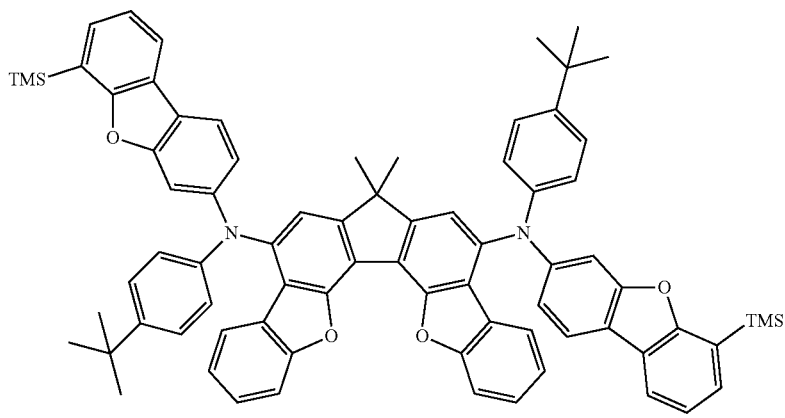

-continued
<Chemical Formula 146>
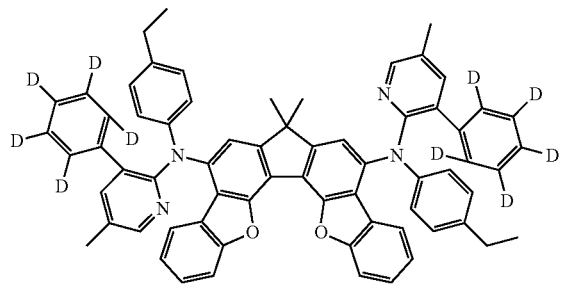
<Chemical Formula 147>
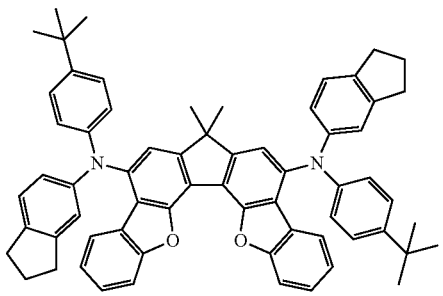
<Chemical Formula 148>
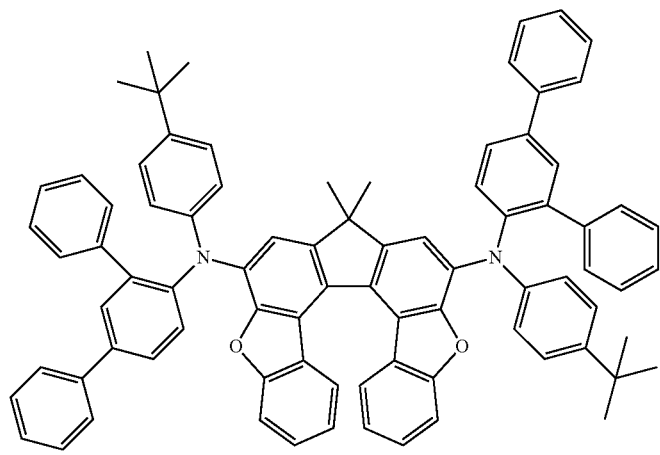
<Chemical Formula 149>
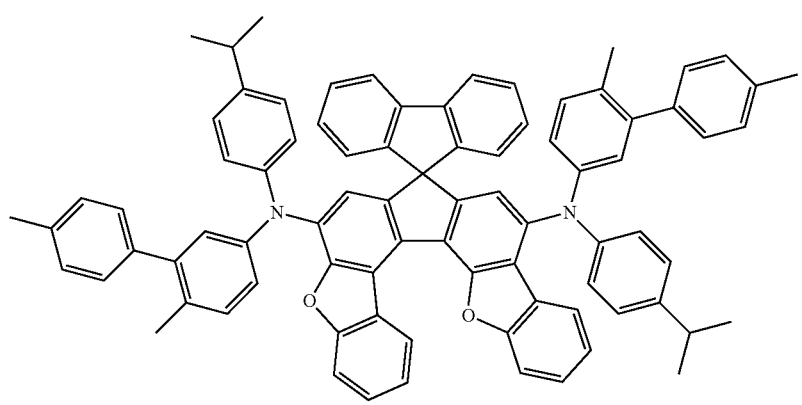
<Chemical Formula 150>
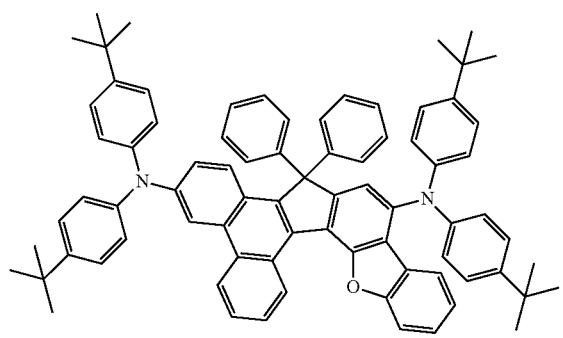
<Chemical Formula 151>
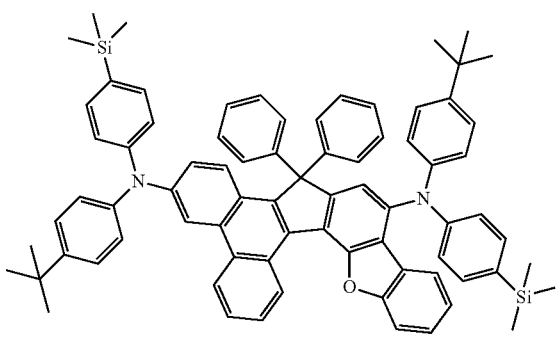

-continued
<Chemical Formula 152>
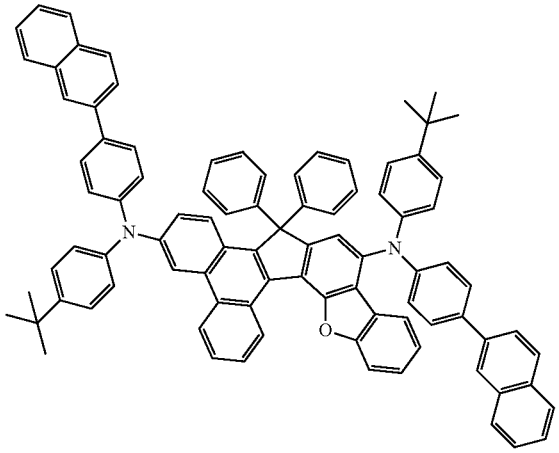
<Chemical Formula 153>
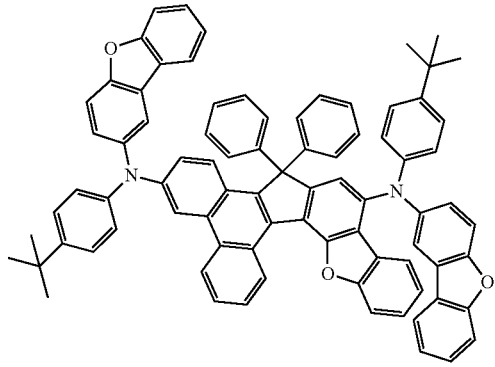
<Chemical Formula 154>
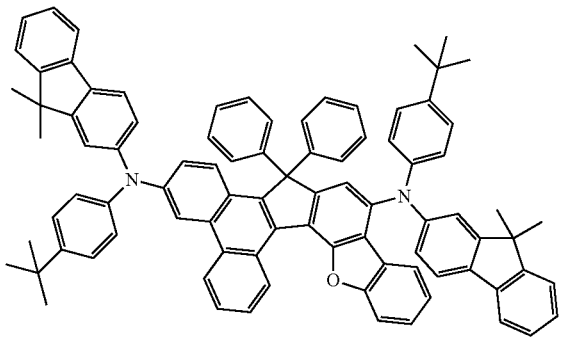
<Chemical Formula 155>
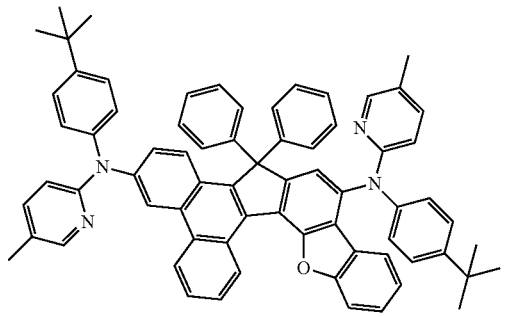
<Chemical Formula 156>
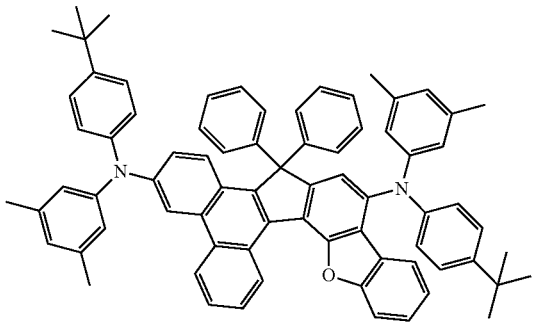
<Chemical Formula 157>
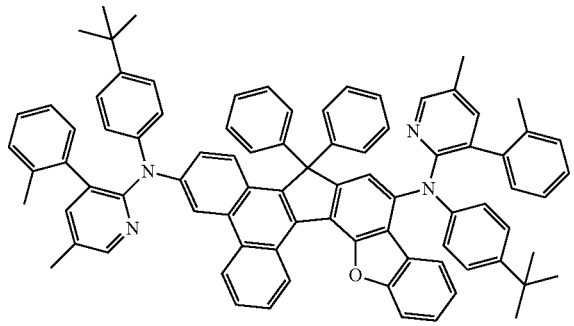
<Chemical Formula 158>
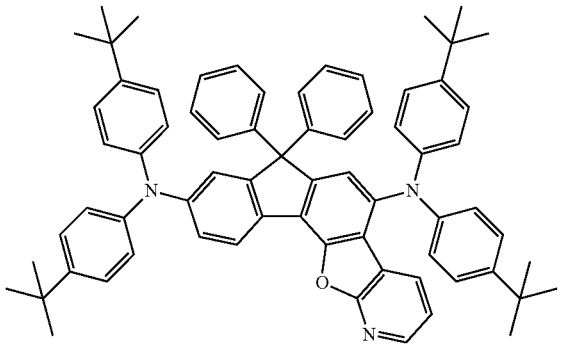
<Chemical Formula 159>
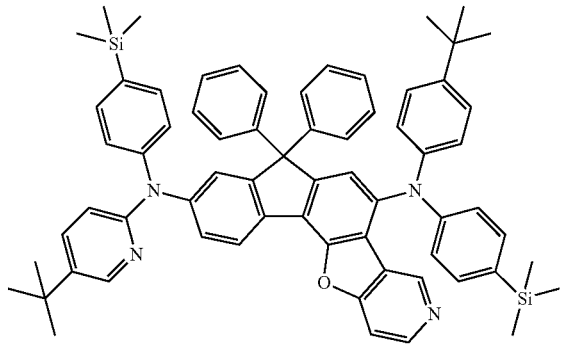

-continued
<Chemical Formula 160>
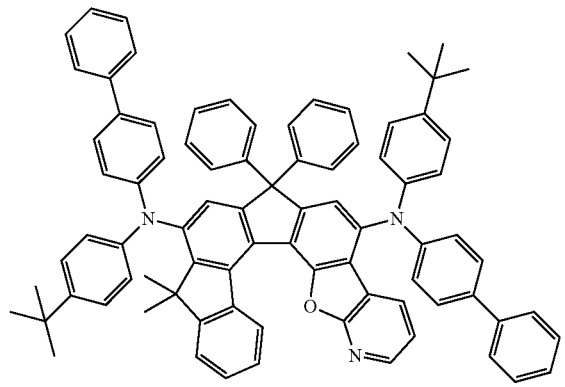
<Chemical Formula 161>
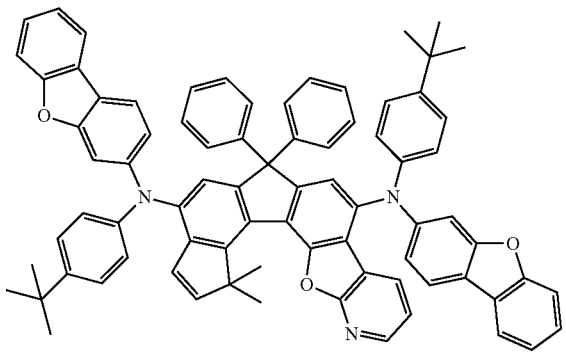
<Chemical Formula 162>
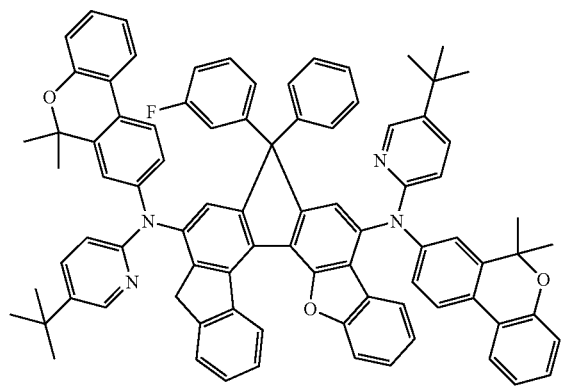
<Chemical Formula 163>
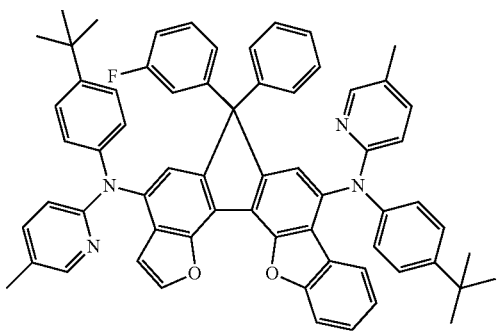
<Chemical Formula 164>
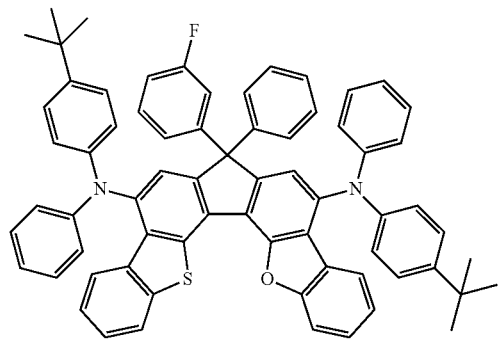
<Chemical Formula 165>
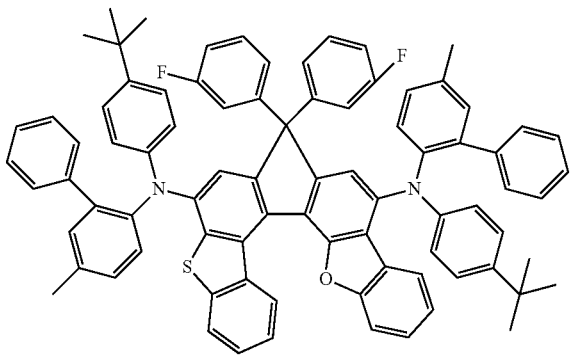
<Chemical Formula 166>
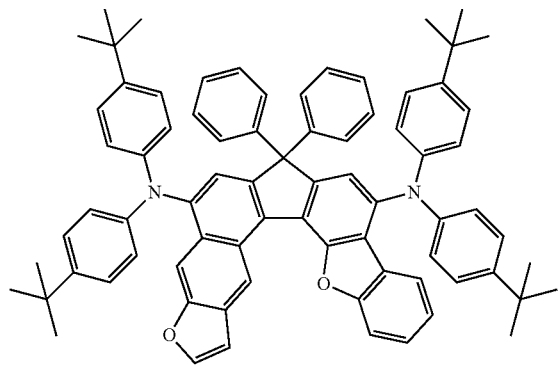
<Chemical Formula 167>
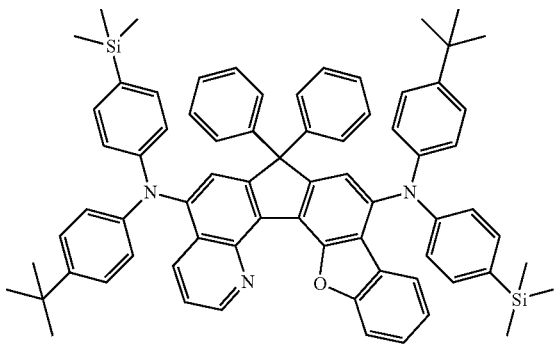

-continued
<Chemical Formula 168>
<Chemical Formula 169>
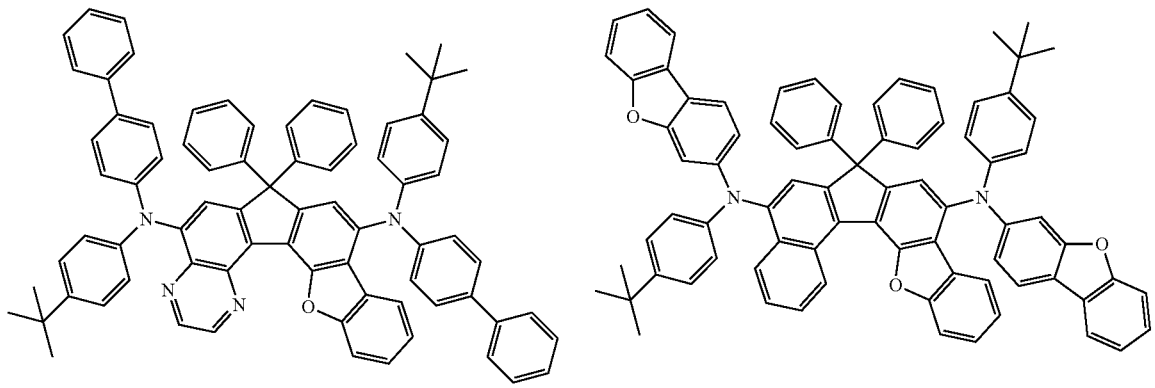
<Chemical Formula 170>
<Chemical Formula 171>
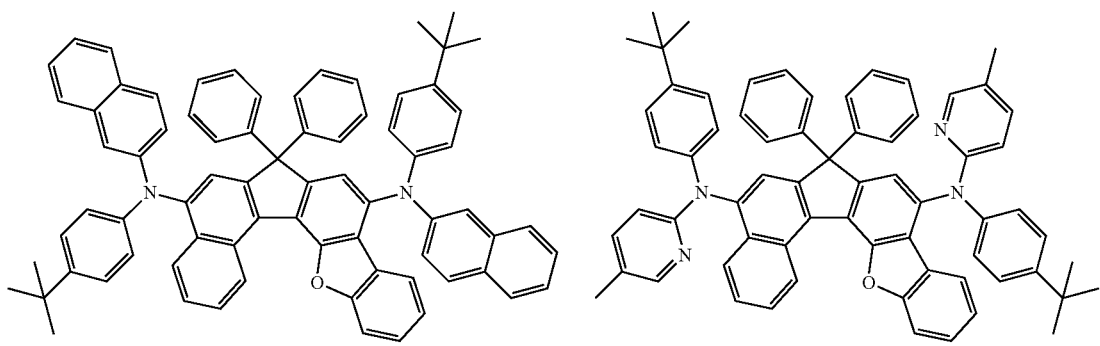
<Chemical Formula 172>
<Chemical Formula 173>
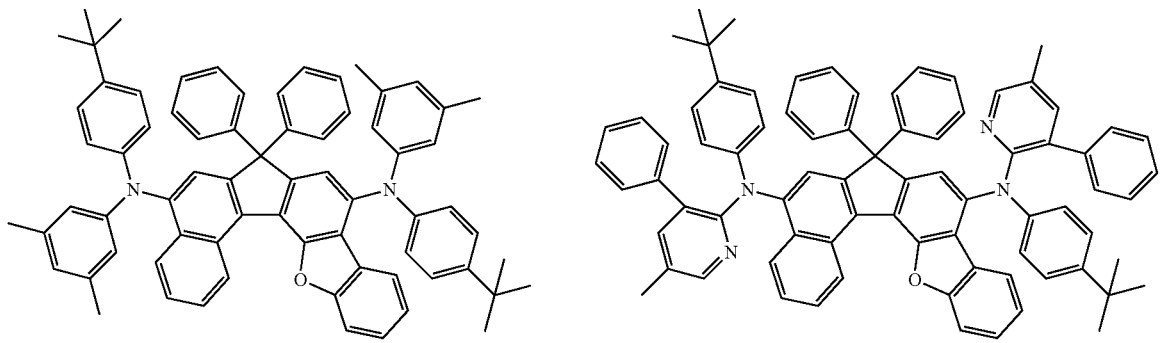
<Chemical Formula 174>
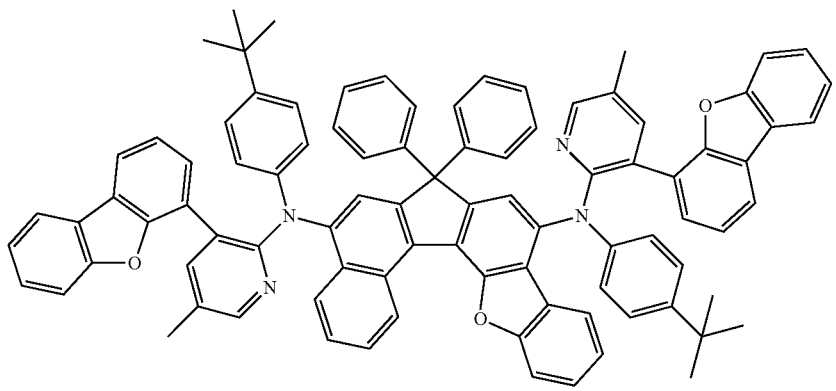

-continued
<Chemical Formula 175>
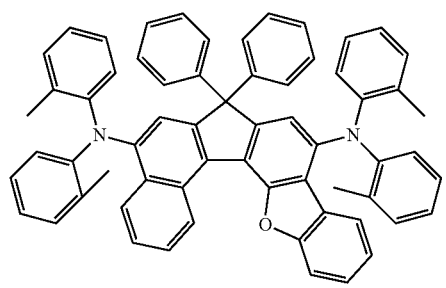
<Chemical Formula 176>
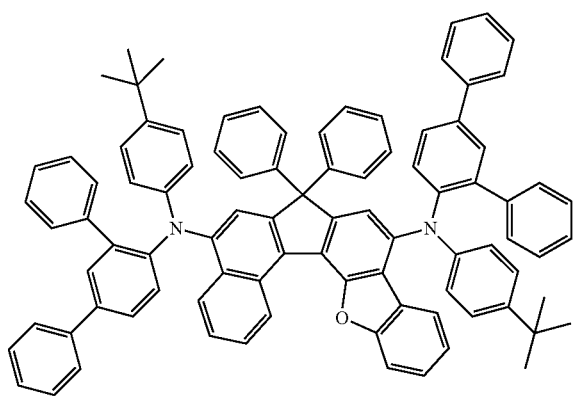
<Chemical Formula 177>
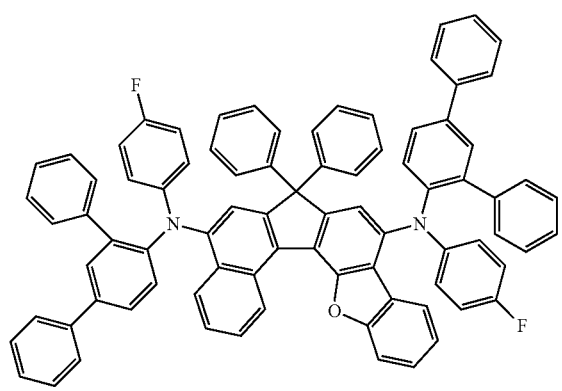
<Chemical Formula 178>
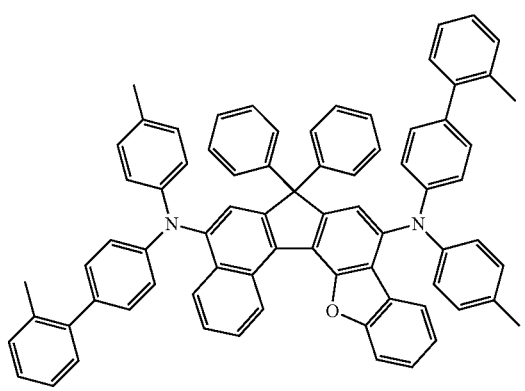
<Chemical Formula 179>
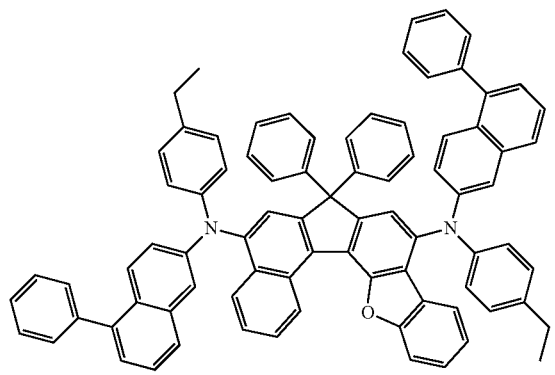
<Chemical Formula 180>
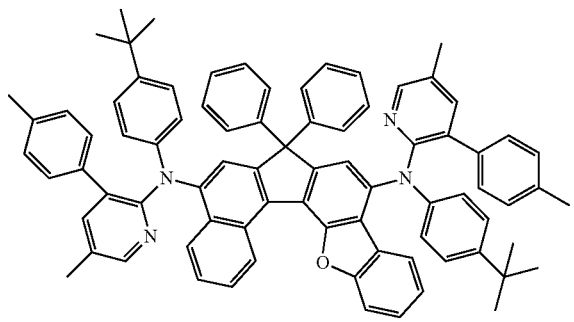
<Chemical Formula 181>
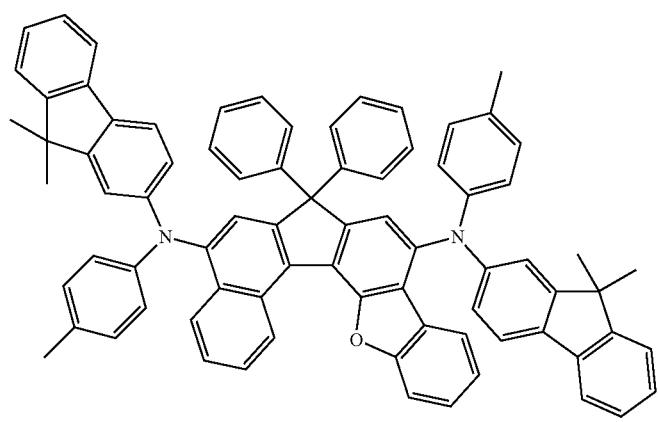

<Chemical Formula 182>
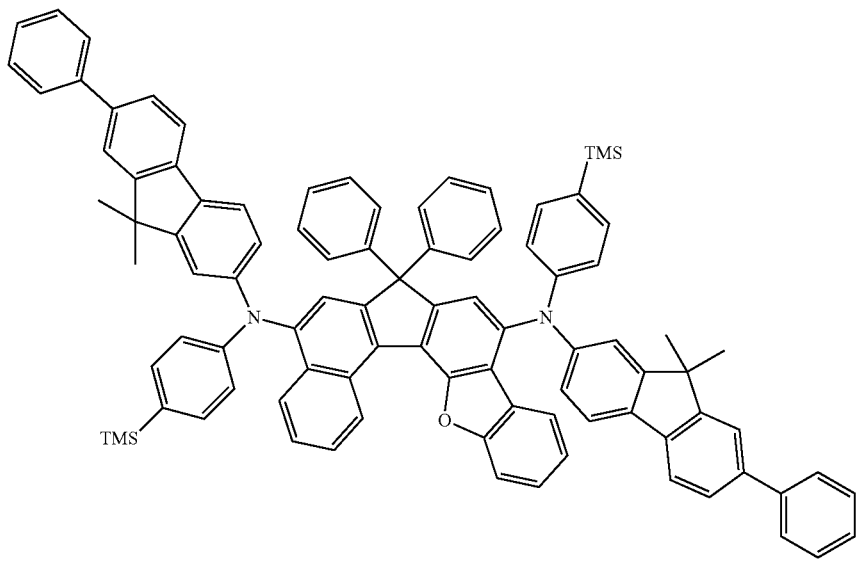
<Chemical Formula 183>
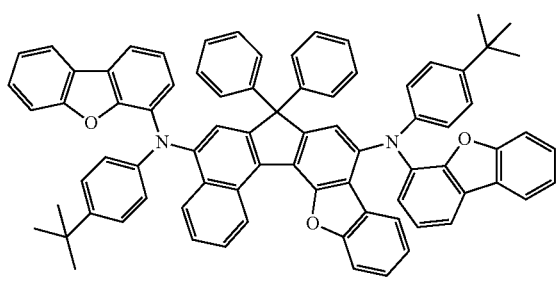
<Chemical Formula 184>
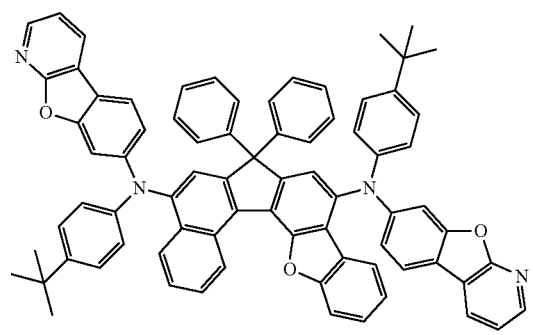
<Chemical Formula 185>
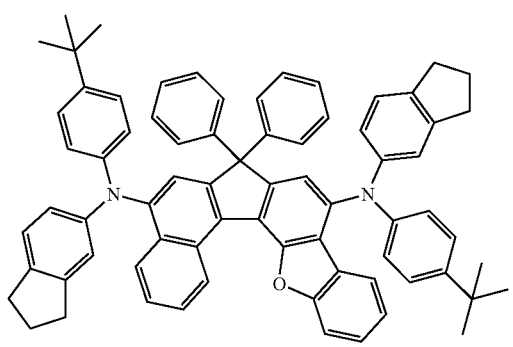
<Chemical Formula 186>
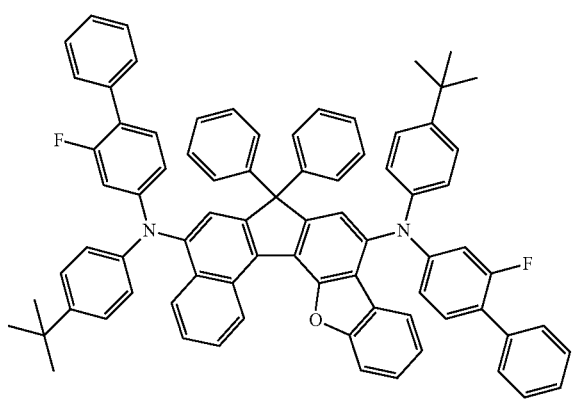
<Chemical Formula 187>
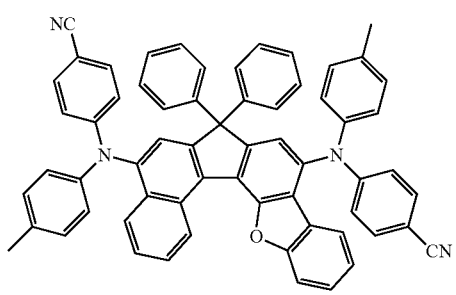
<Chemical Formula 188>
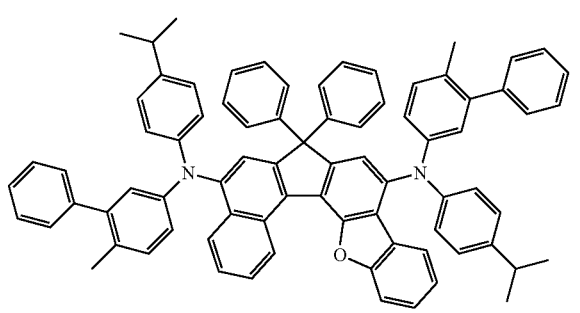

<Chemical Formula 189>                <Chemical Formula 190>
<Chemical Formula 191>                <Chemical Formula 192>
<Chemical Formula 193>                <Chemical Formula 194>
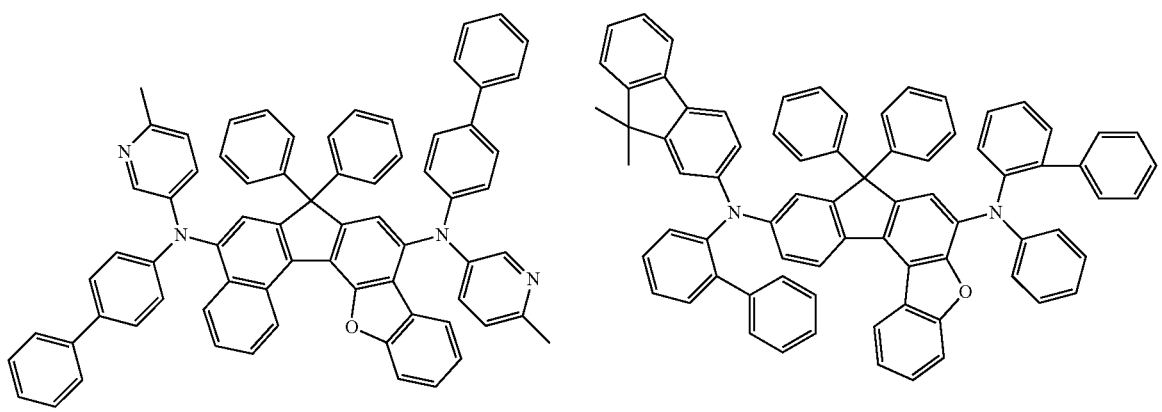
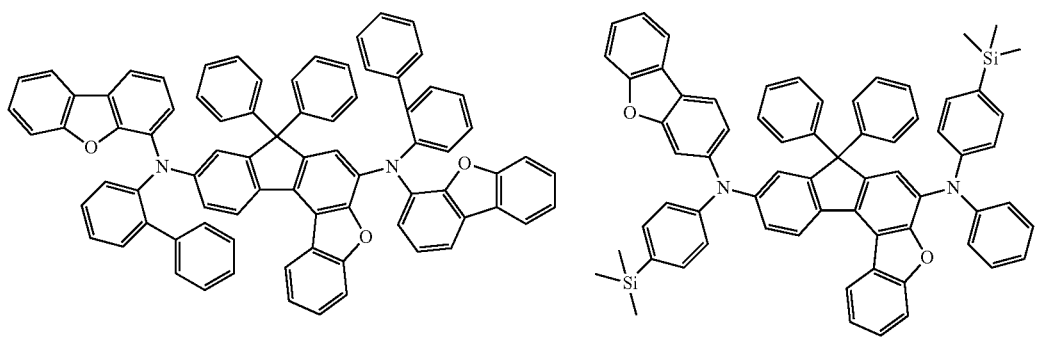
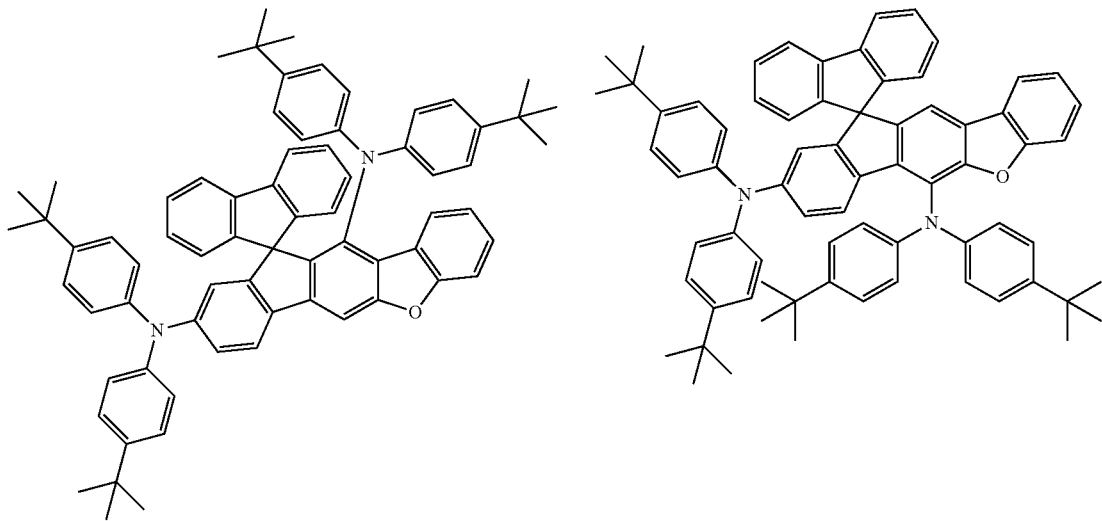

<Chemical Formula 195>
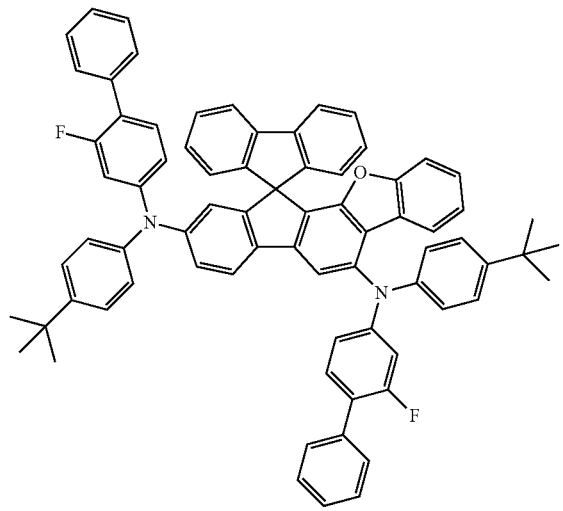
<Chemical Formula 196>
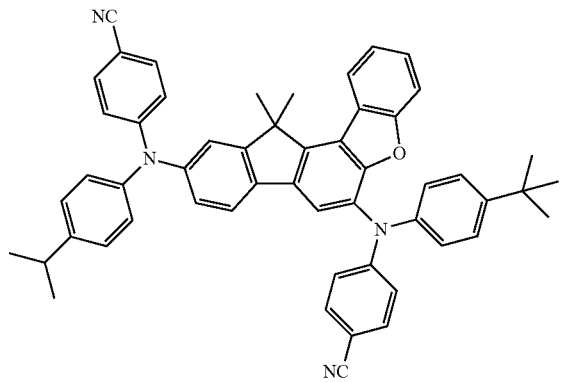
<Chemical Formula 197>
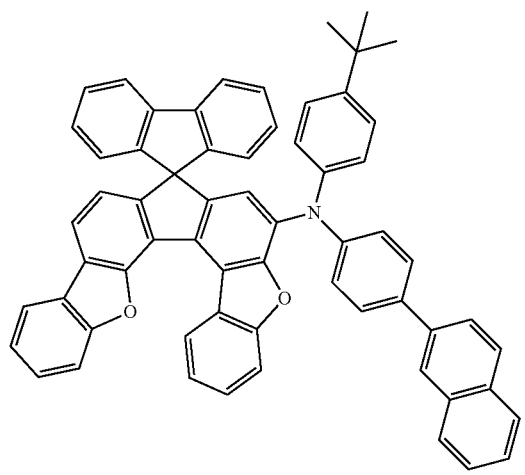
<Chemical Formula 198>
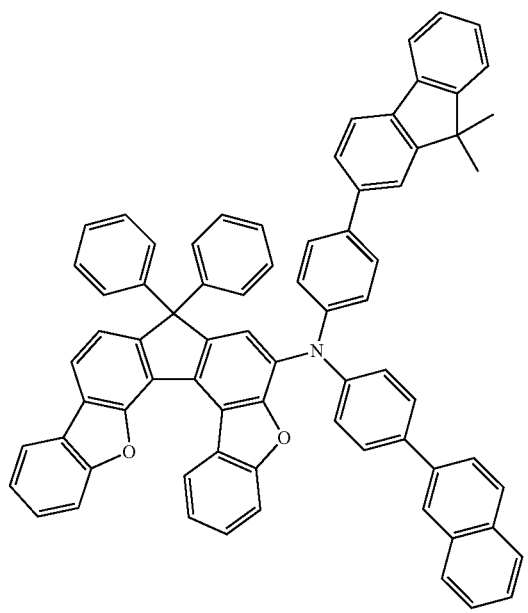

-continued
<Chemical Formula 199>
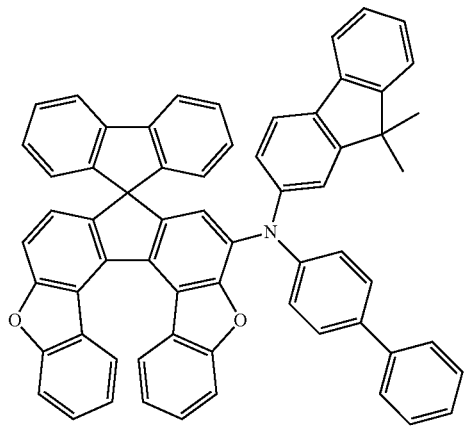
<Chemical Formula 200>
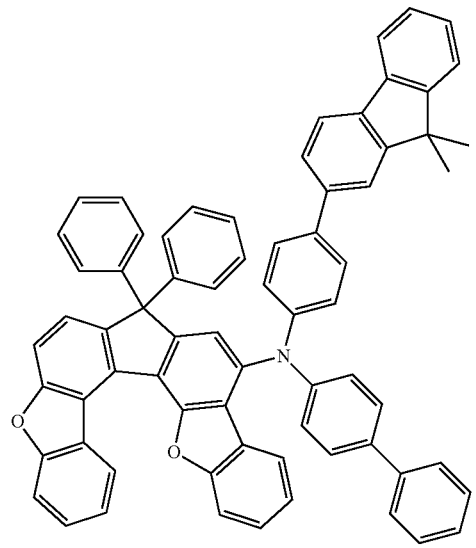
<Chemical Formula 201>
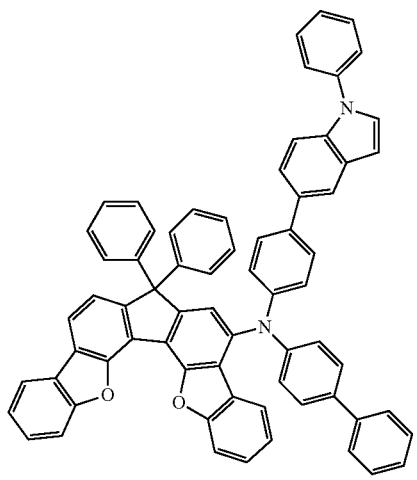
<Chemical Formula 202>
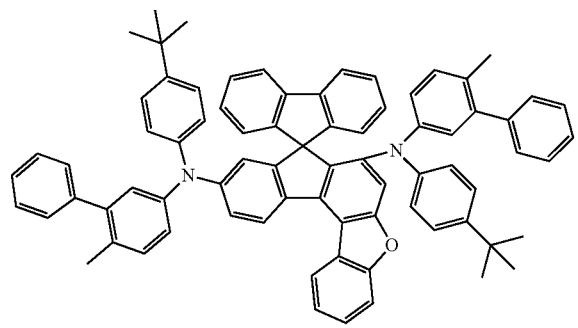
<Chemical Formula 203>
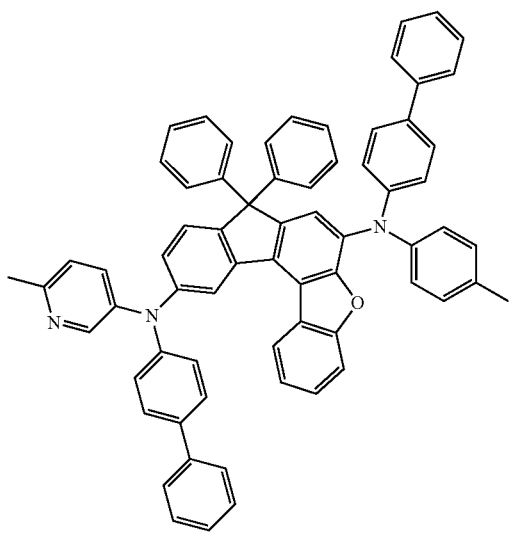
<Chemical Formula 204>
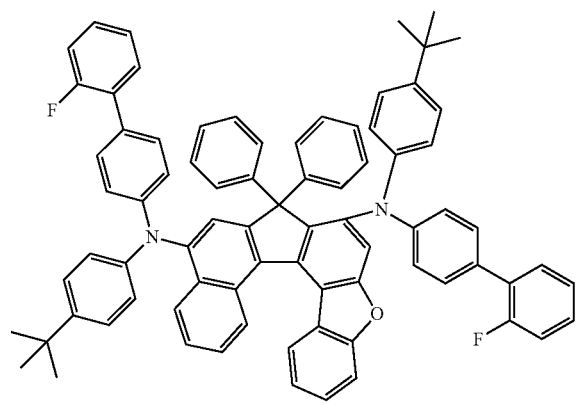

-continued
<Chemical Formula 205>
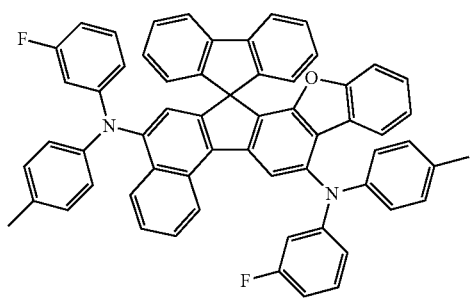
<Chemical Formual 206>
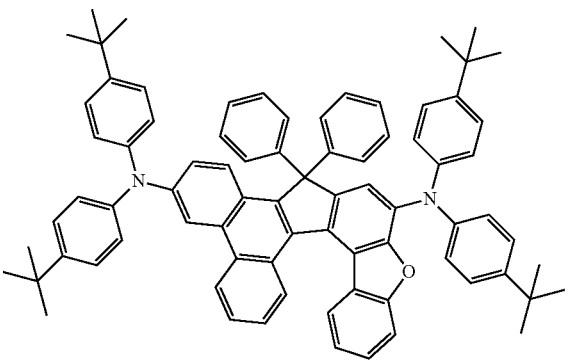
<Chemical Formula 207>
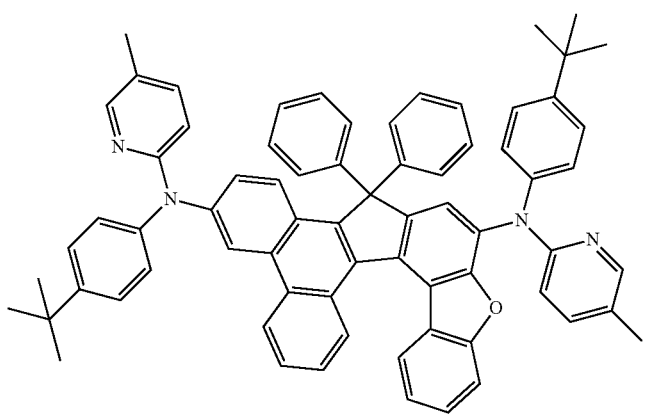
<Chemical Formula 208>
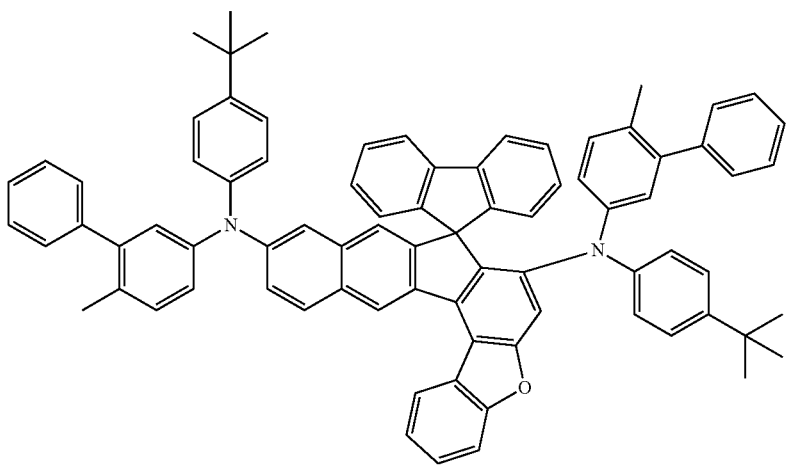
<Chemical Formula 209>
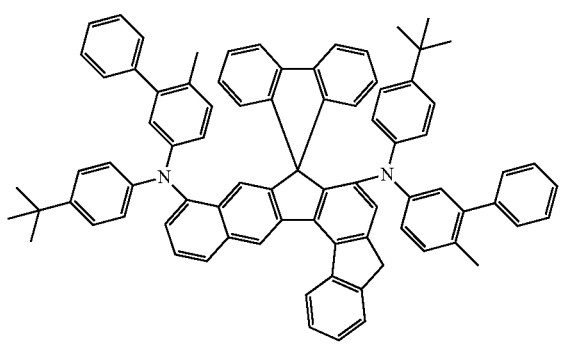
<Chemical Formula 210>
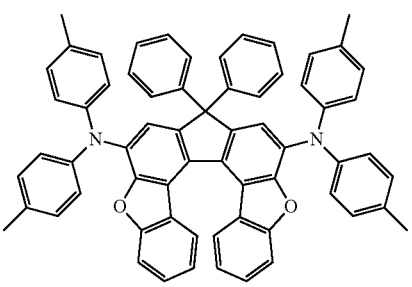

-continued
<Chemical Formula 211>
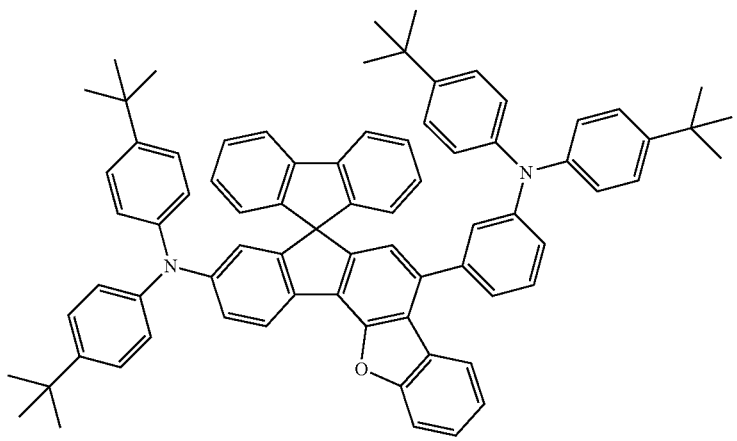
<Chemical Formula 212>
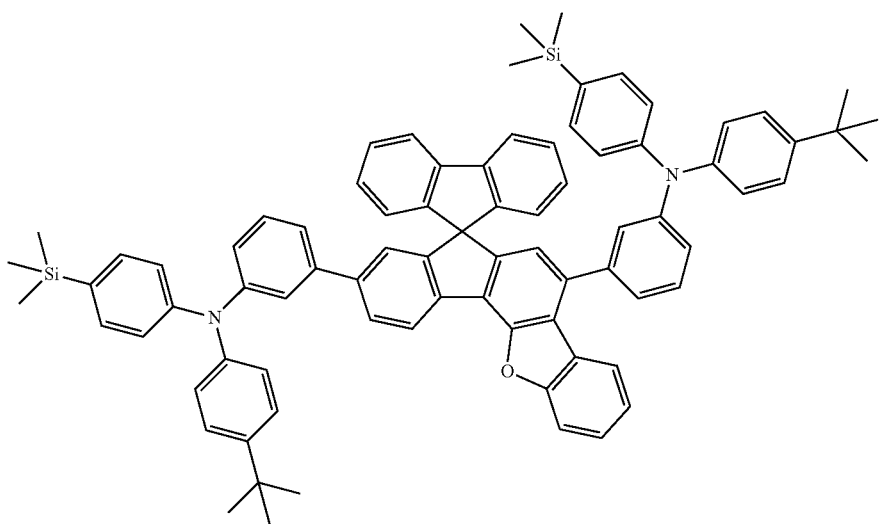
<Chemical Formula 213>
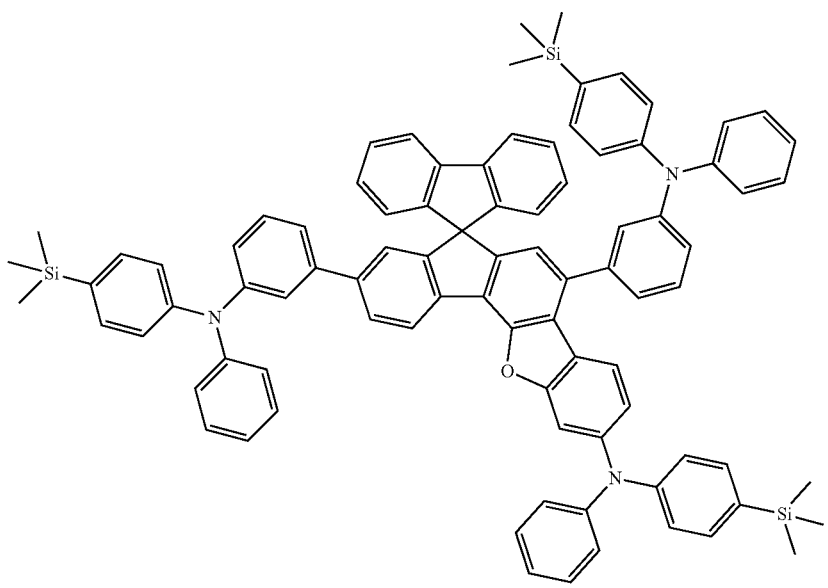

-continued
<Chemical Formula 214>
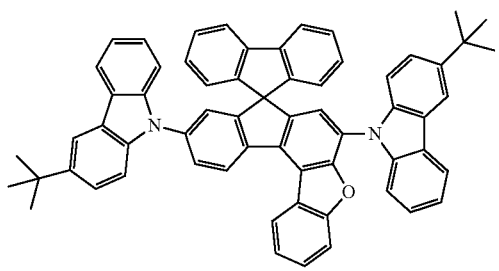
<Chemical Formula 215>
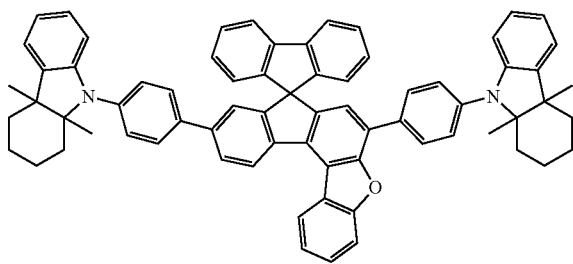
<Chemical Formula 216>
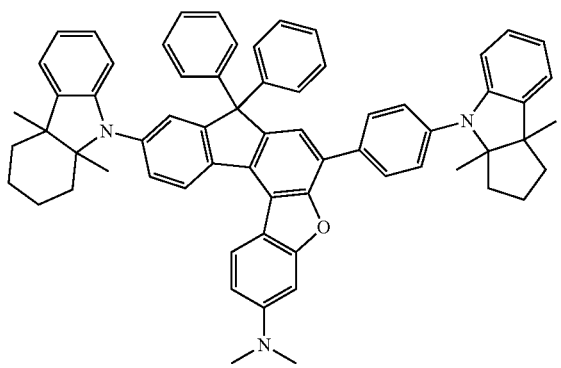
<Chemical Formula 217>
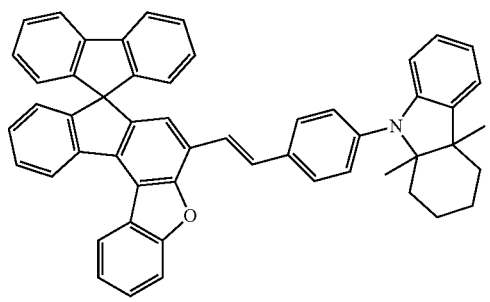
<Chemical Formual 218>
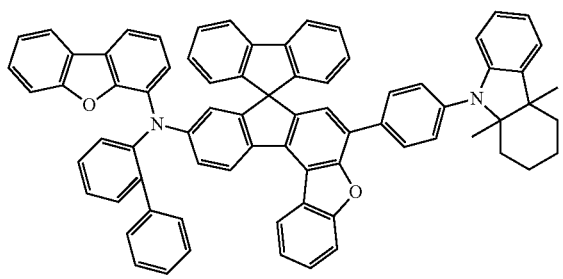
<Chemical Formula 219>
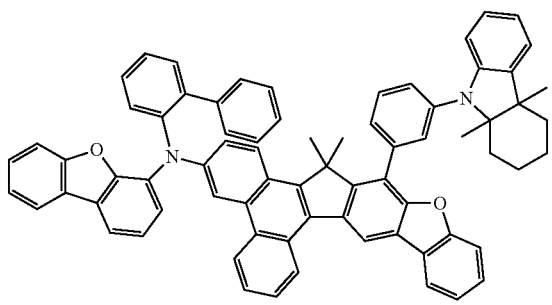
<Chemical Formula 220>
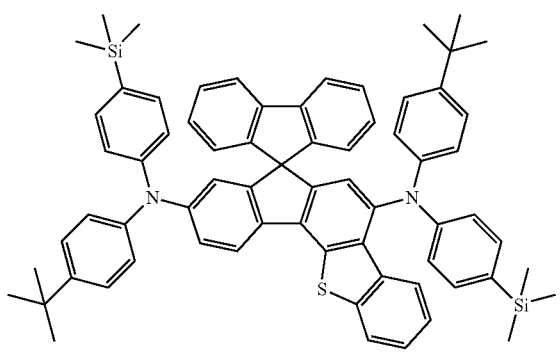
<Chemical Formula 221>
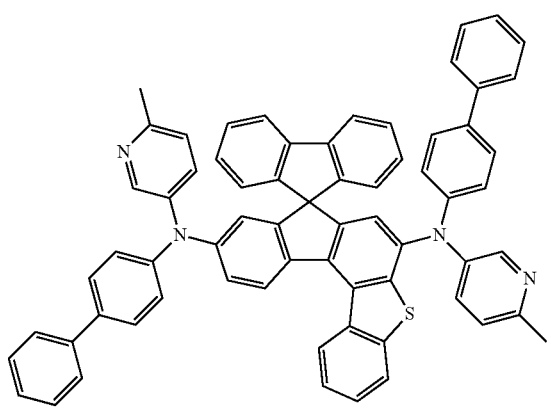

-continued
<Chemical Formula 222>
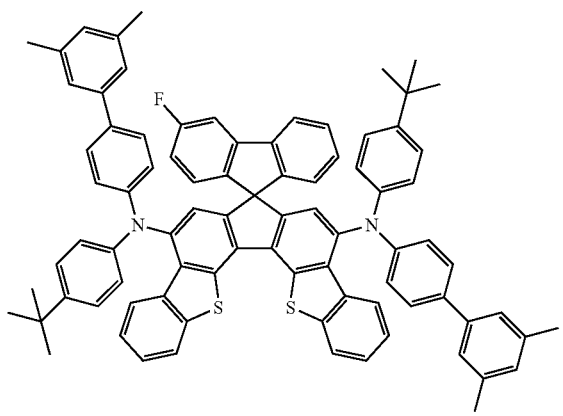
<Chemical Formula 223>
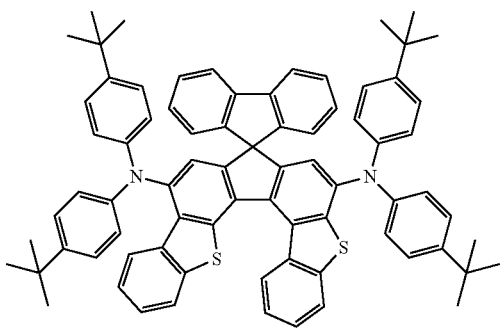
<Chemical Formula 224>
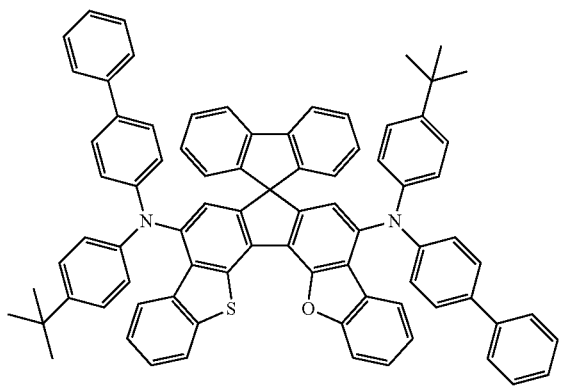
<Chemical Formula 225>
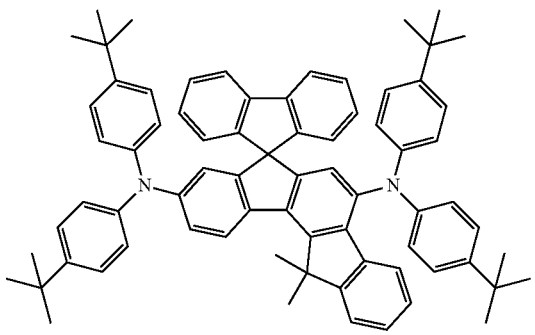
<Chemical Formula 226>
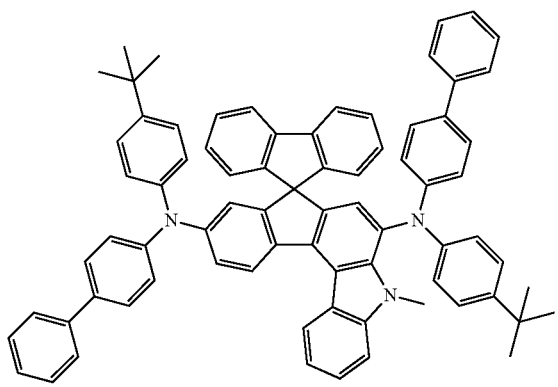
<Chemical Formula 227>
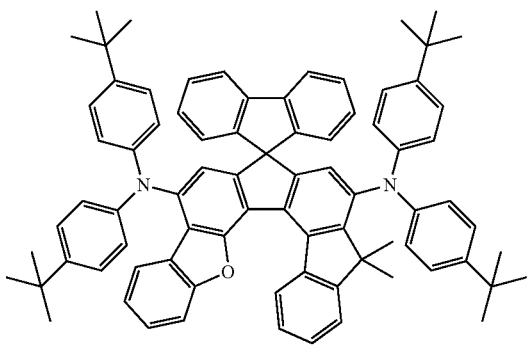

-continued
<Chemical Formula 228>
<Chemical Formula 229>
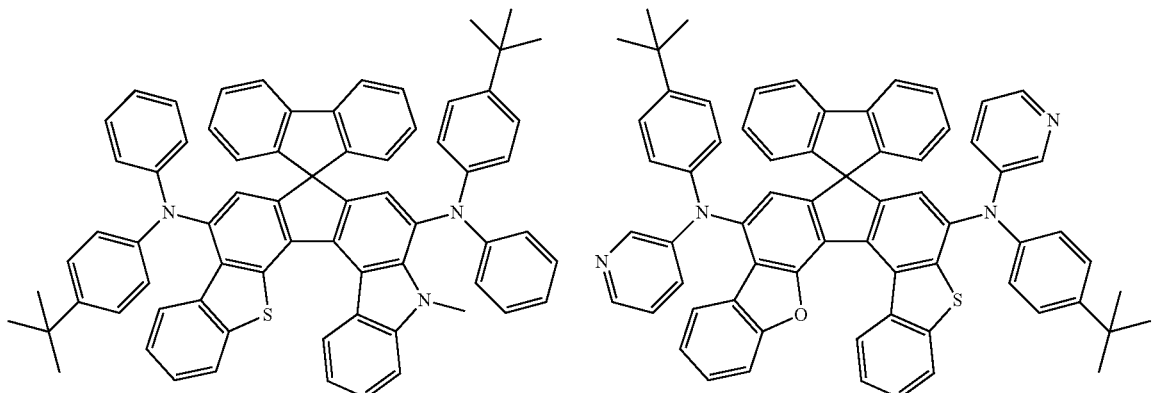
<Chemical Formula 230>
<Chemical Formula 231>
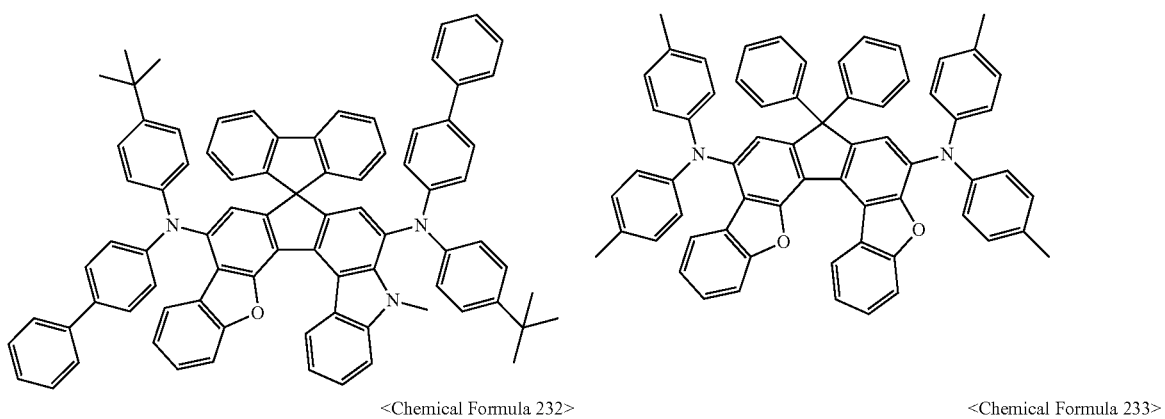
<Chemical Formula 232>
<Chemical Formula 233>
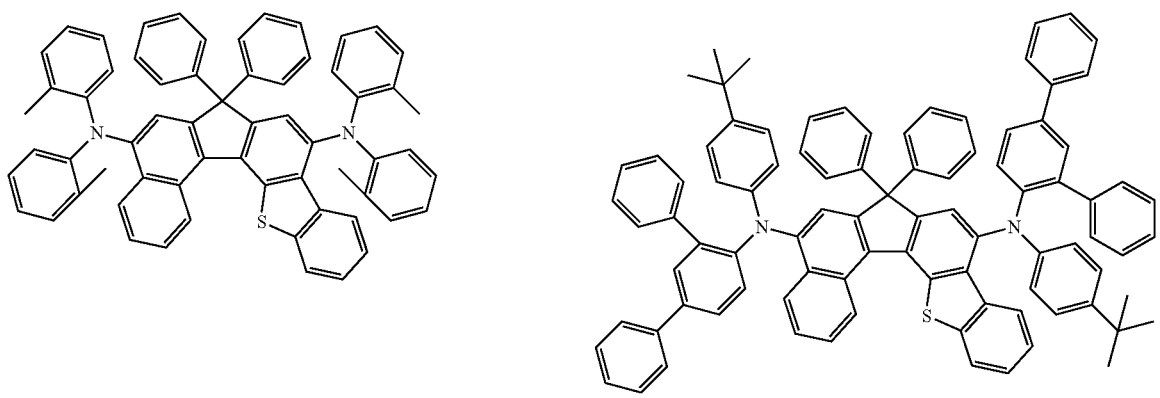
<Chemical Formula 234>
<Chemical Formula 235>
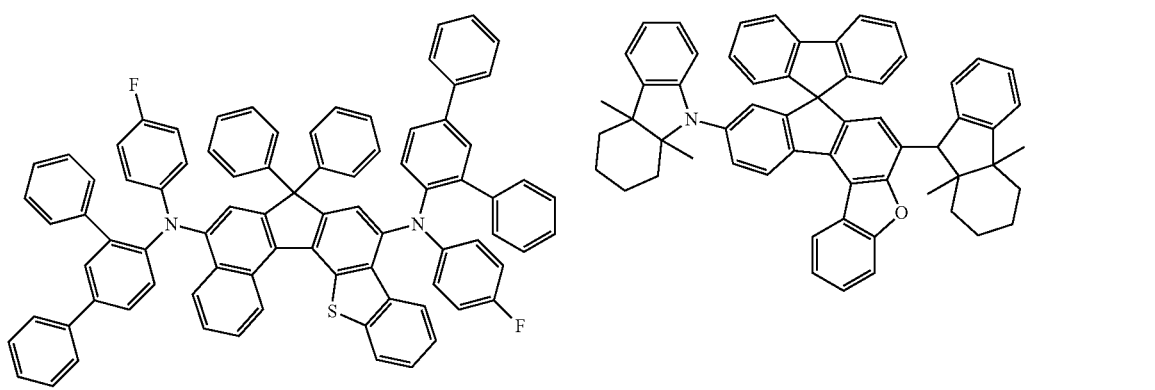

<Chemical Formula 236>

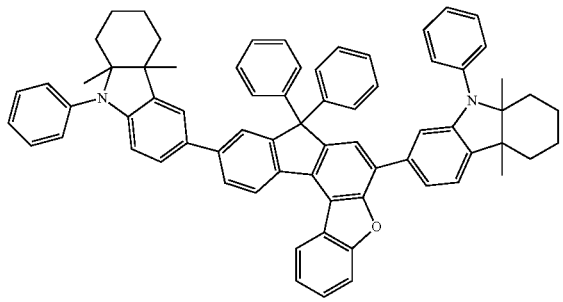

<Chemical Formula 237>

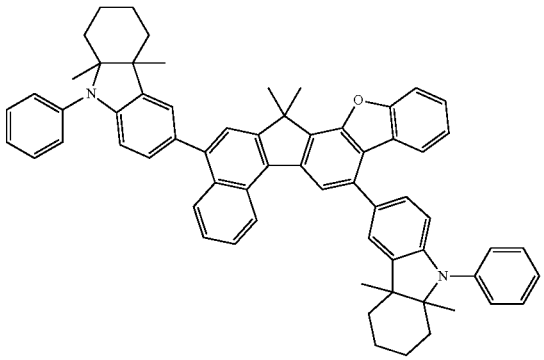

<Chemical Formula 238>

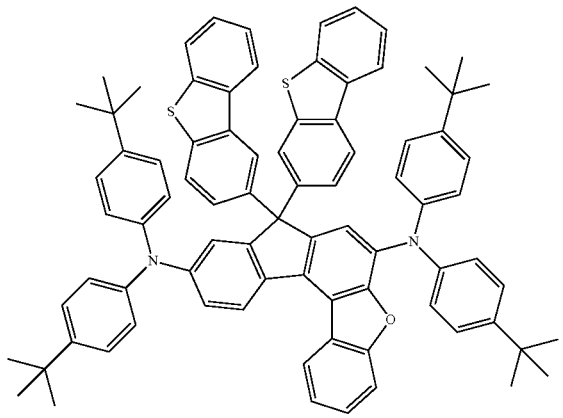

<Chemical Formula 239>

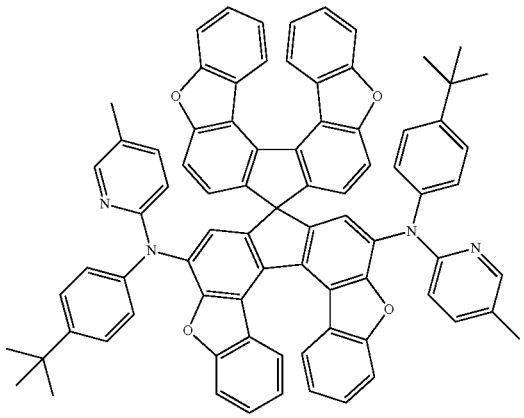

The compound represented by Chemical Formula C is an anthracene ring compound to which a fused ring consisting of the dibenzofuran moiety of Structural Formula A with the ring of P1 or P2 is connected via the linker $L_{21}$ at position 10.

The compound of Chemical Formula C may be used as a host in the light-emitting layer. In this regard, the organic light-emitting diode of the present disclosure may employ the compound of Chemical Formula A or B as a dopant.

In some embodiments, the substituent $Ar_{21}$ on the compound of Chemical Formula C may be a compound represented by the following Chemical Formula C-1:

[Chemical Formula C-1]

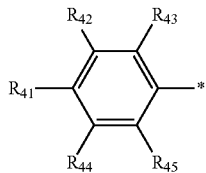

wherein, $R_{41}$ to $R_{45}$ may be the same or different, and are each as defined for $R_{11}$ to $R_{18}$ in claim 1; and may form a saturated or unsaturated ring with respective adjacent substituents.

In a particular embodiment, the linker $L_{21}$ in Chemical Formula C may be a single bond or a substituted or unsubstituted arylene of 6 to 20 carbon atoms.

Concrete examples of the compound represented by Chemical Formula C include, but are not limited to, the following [Cpd. 201] to [Cpd. 275].

<Cpd. 201>

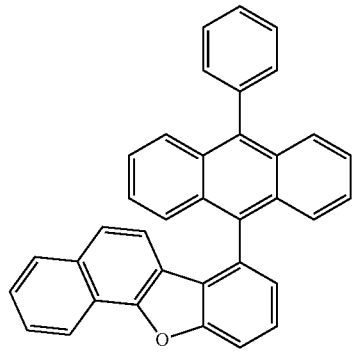

-continued
<Cpd. 202>
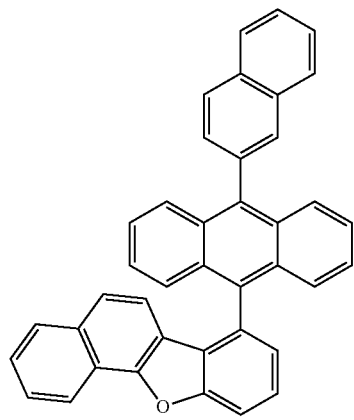
<Cpd. 203>
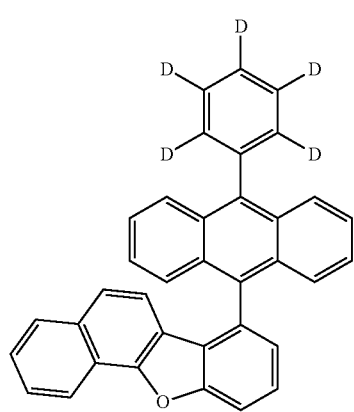
<Cpd. 204>
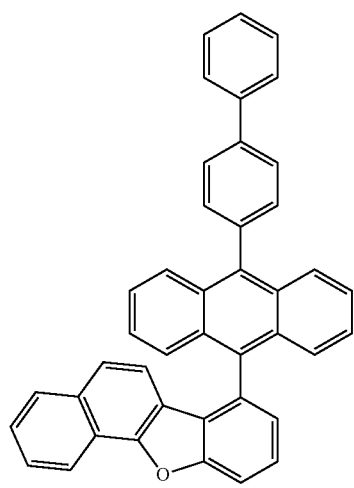
-continued
<Cpd. 205>
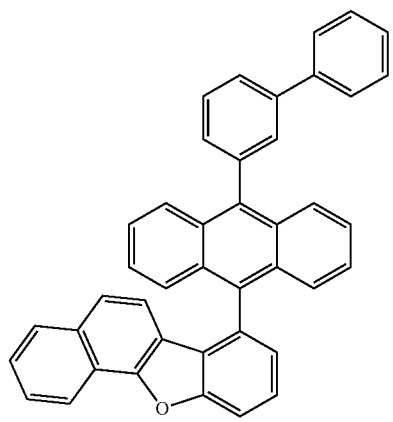
<Cpd. 206>
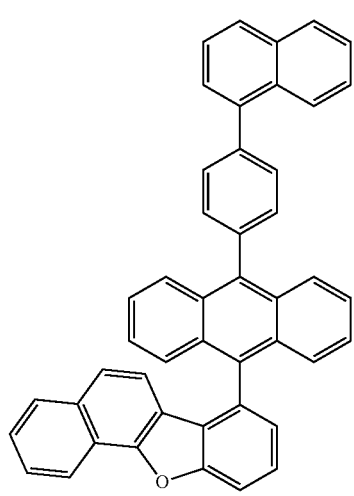
<Cpd. 207>
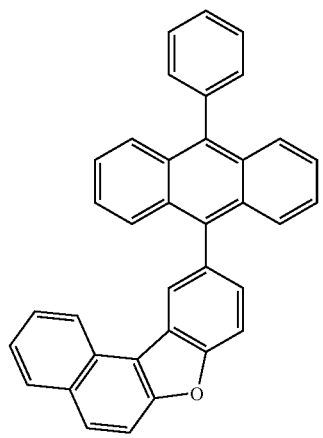

<Cpd. 208>
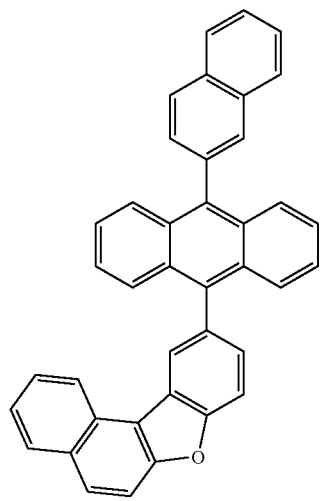
<Cpd. 209>
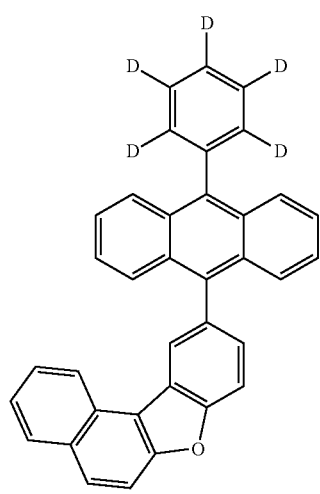
<Cpd. 210>
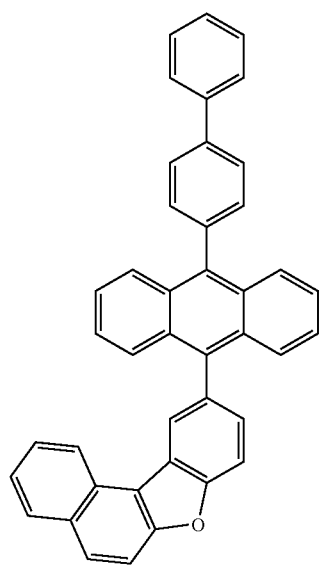
<Cpd. 211>
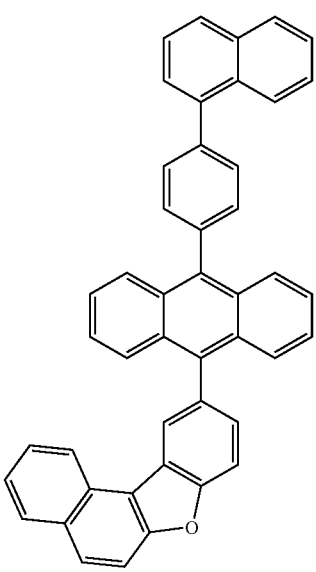
<Cpd. 212>
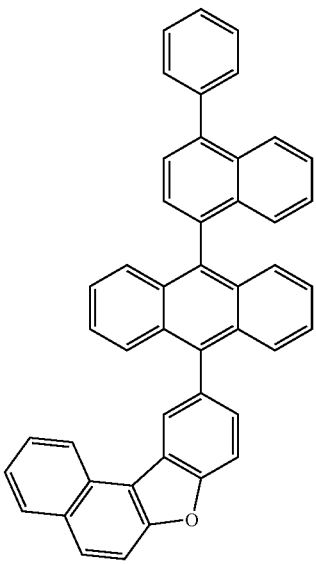
<Cpd. 213>
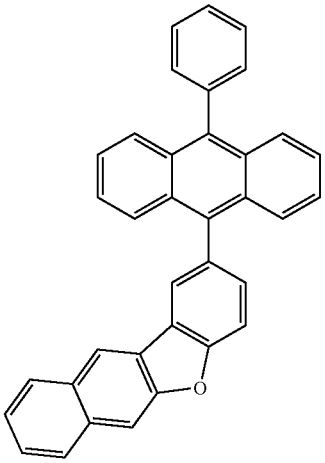

<Cpd. 214>
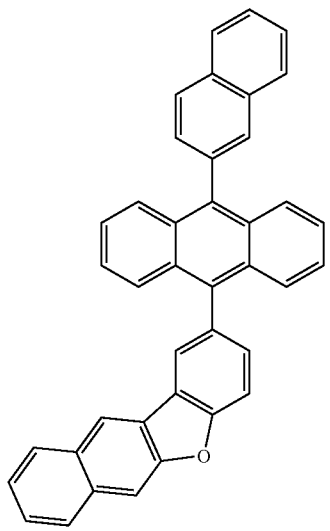
<Cpd. 217>
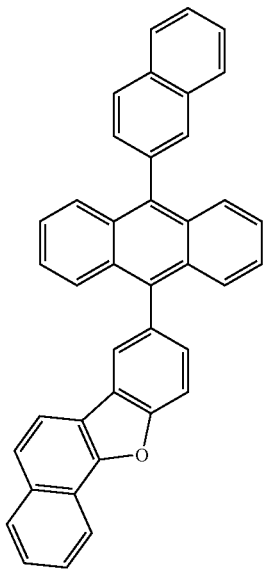
<Cpd. 215>
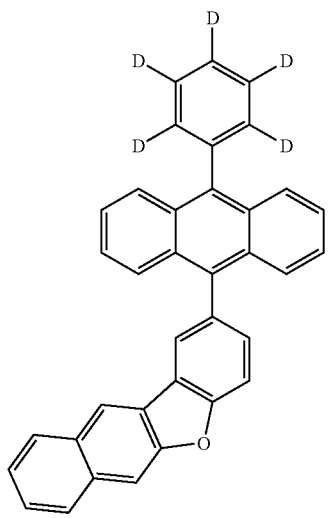
<Cpd. 216>
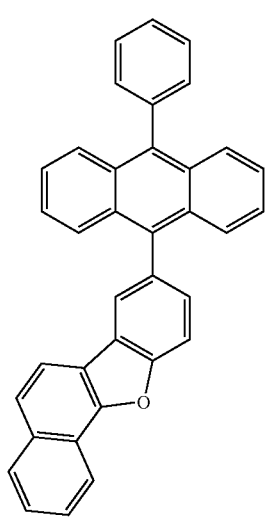
<Cpd. 218>
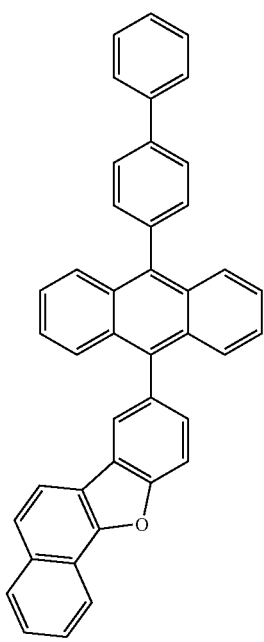

<Cpd. 219>
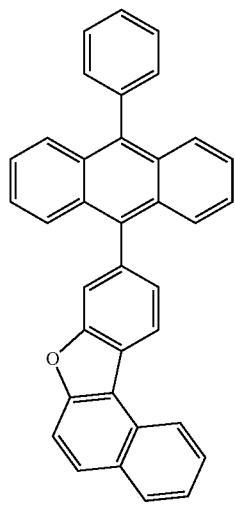
<Cpd. 220>
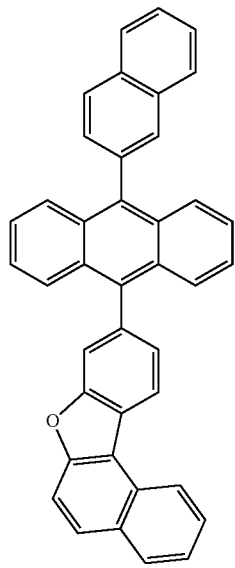
<Cpd. 221>
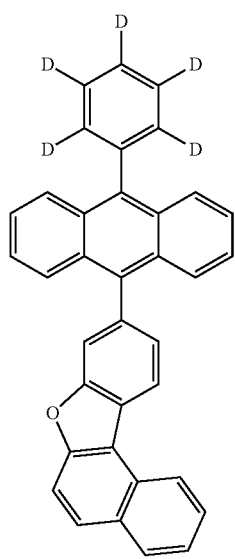
<Cpd. 222>
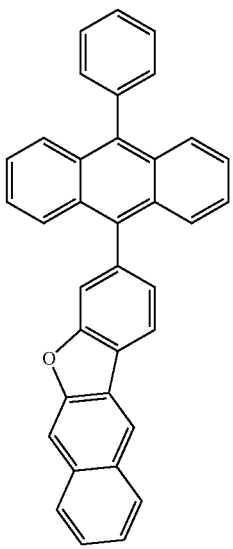
<Cpd. 223>
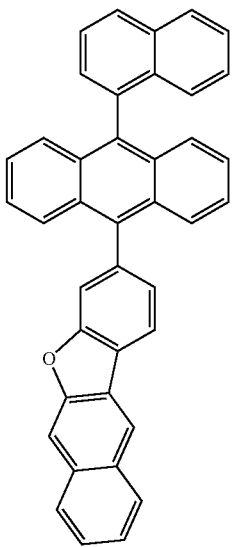

<Cpd. 224>
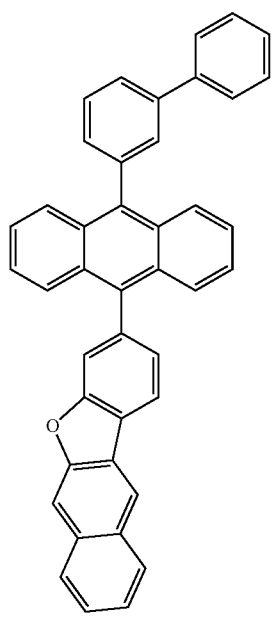
<Cpd. 226>
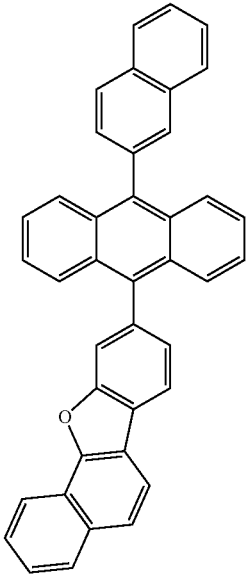
<Cpd. 227>
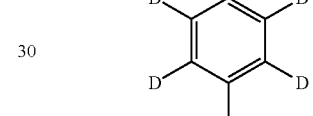
<Cpd. 225>
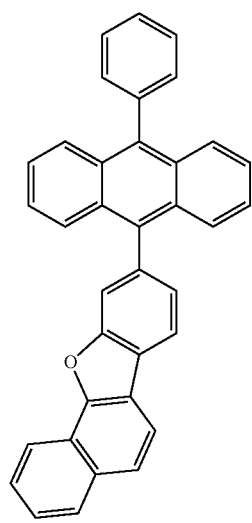
<Cpd. 228>
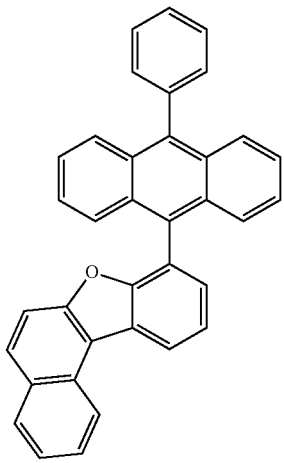

<Cpd. 229>
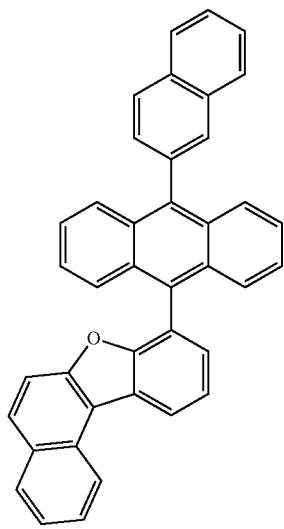
<Cpd. 230>
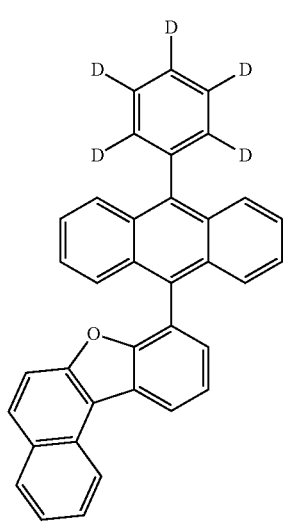
<Cpd. 231>
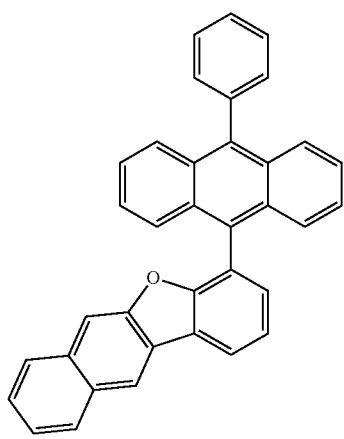
<Cpd. 232>
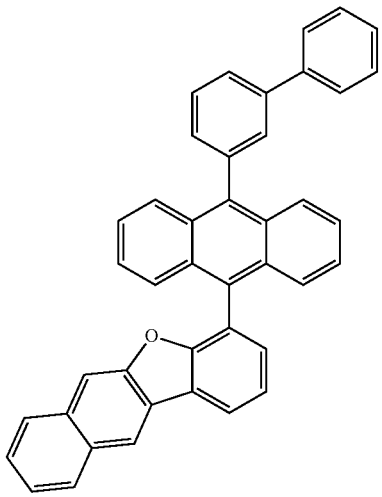
<Cpd. 233>
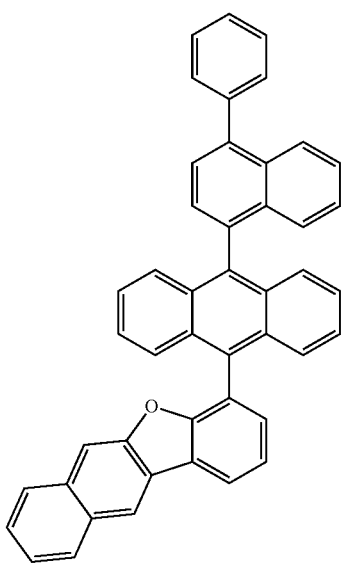
<Cpd. 234>
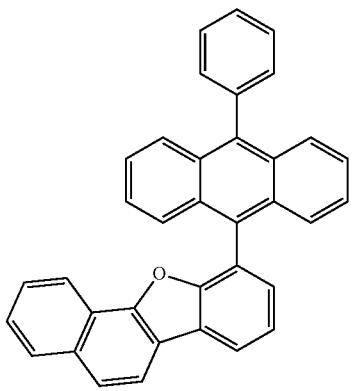

<Cpd. 235>
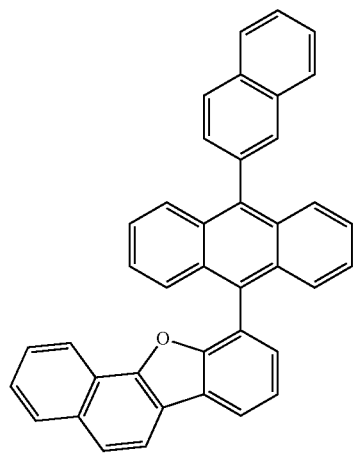
<Cpd. 238>
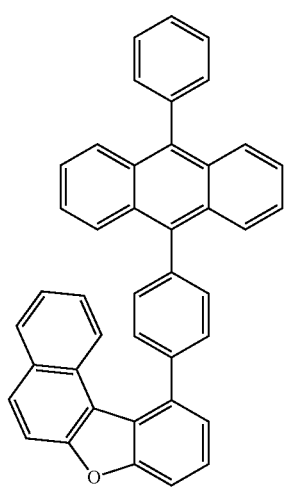
<Cpd. 236>
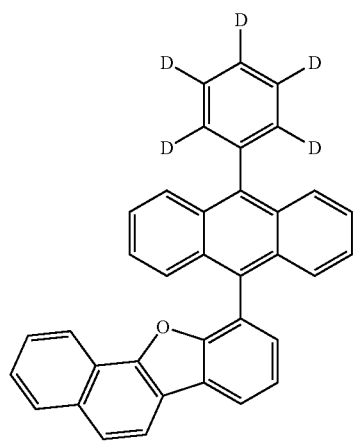
<Cpd. 237>
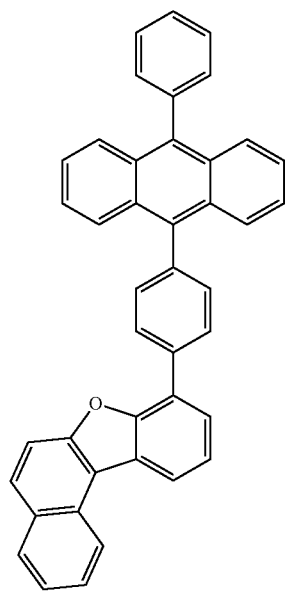
<Cpd. 239>
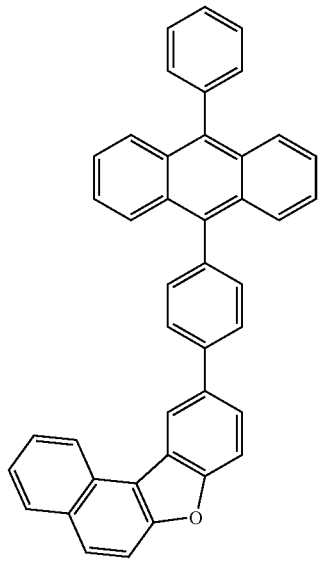

<Cpd. 240>
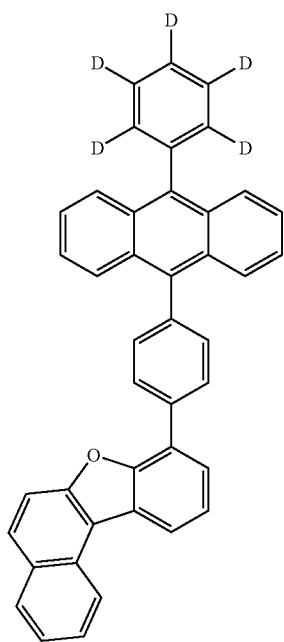
<Cpd. 242>
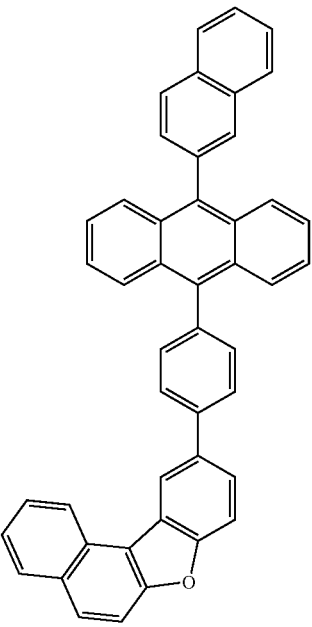
<Cpd. 241>
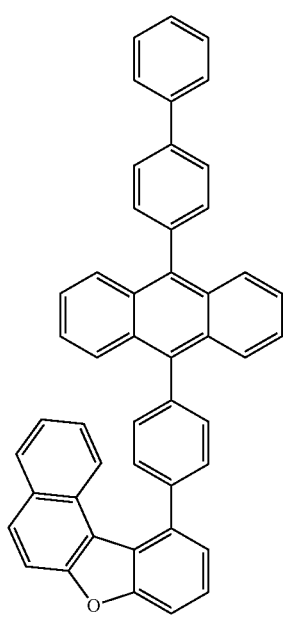
<Cpd. 243>
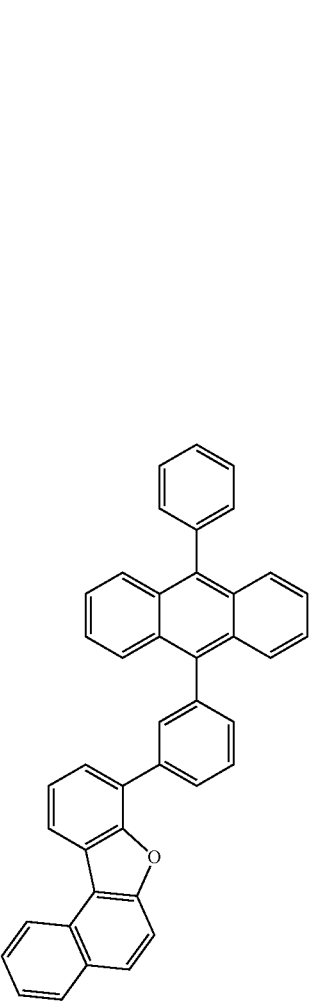

<Cpd. 244>
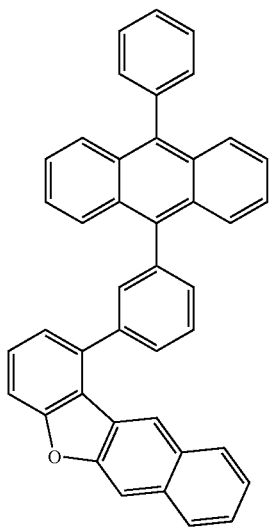
<Cpd. 246>
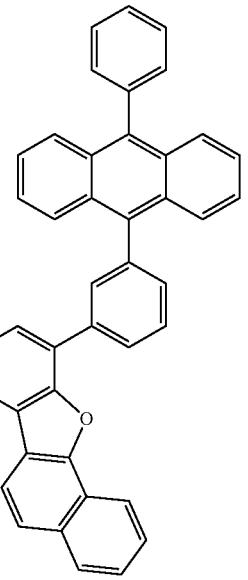
<Cpd. 247>
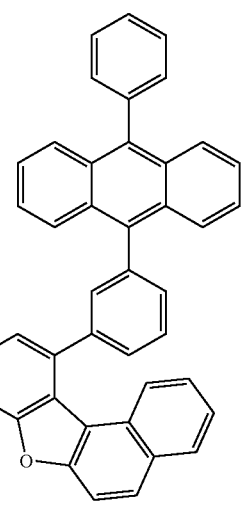
<Cpd. 245>
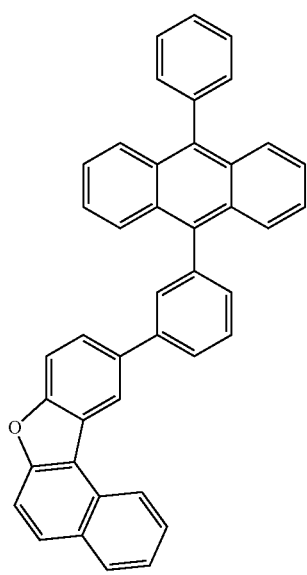
<Cpd. 248>
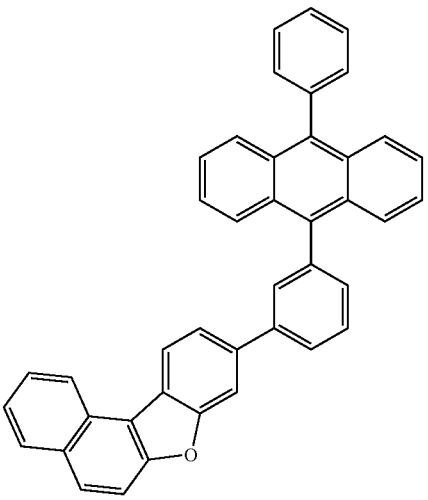

<Cpd. 249>
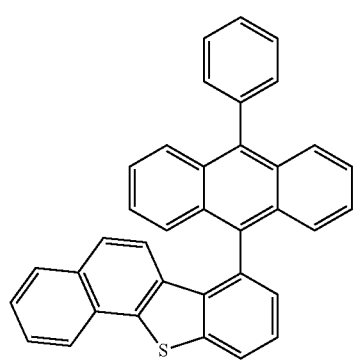
<Cpd. 250>
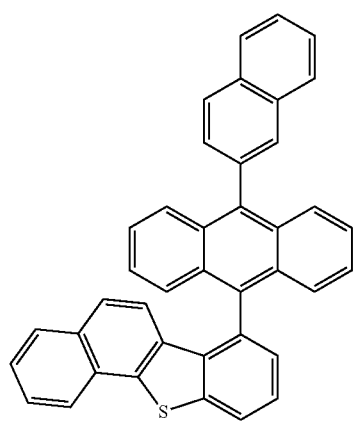
<Cpd. 251>
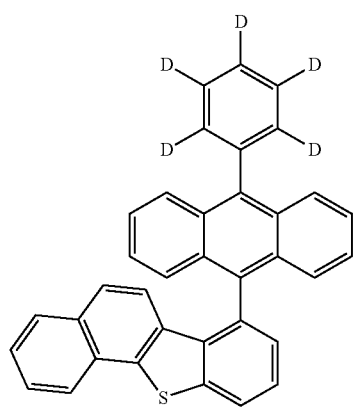
<Cpd. 252>
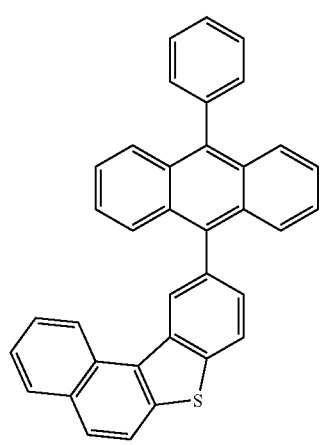
<Cpd. 253>
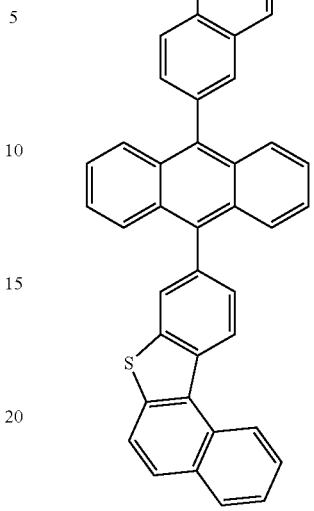
<Cpd. 254>
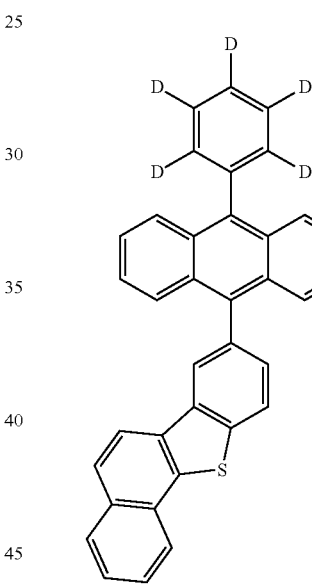
<Cpd. 255>
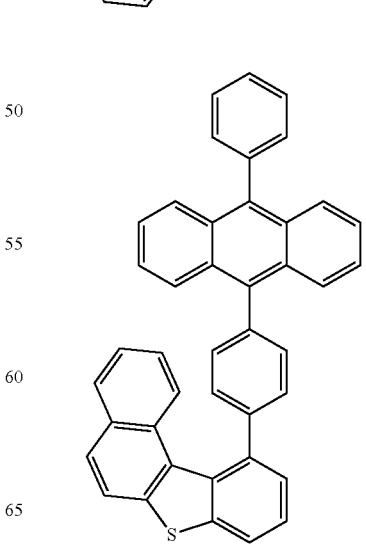

-continued
<Cpd. 256>
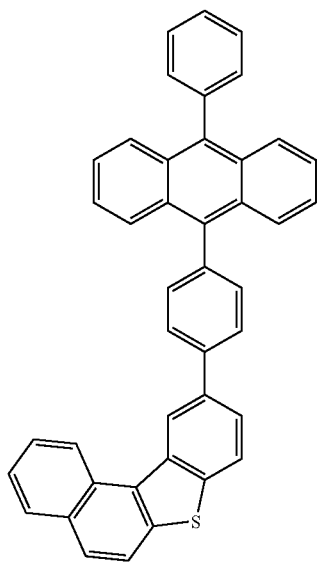
<Cpd. 258>
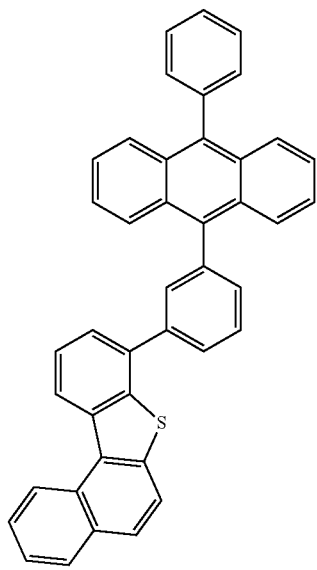
<Cpd. 257>
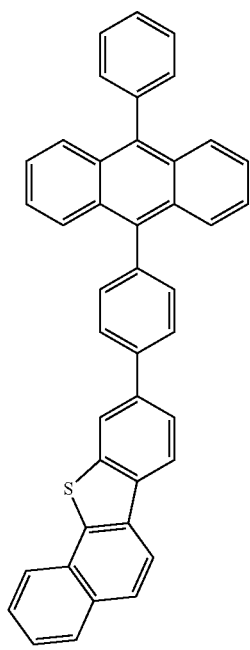
<Cpd. 259>
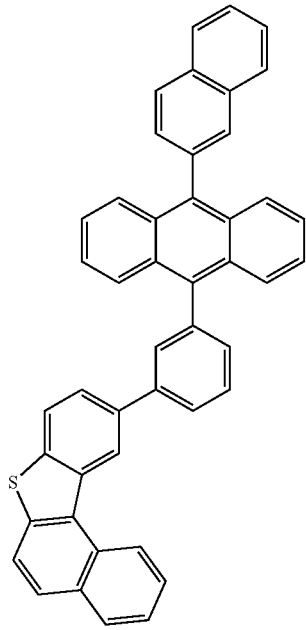

-continued
<Cpd. 260>
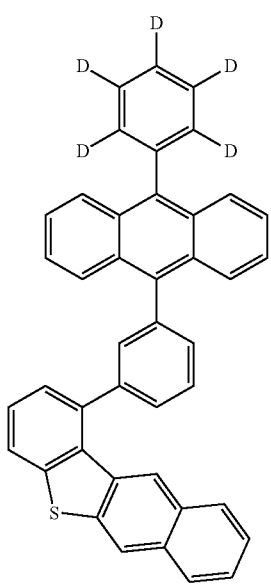
<Cpd. 261>
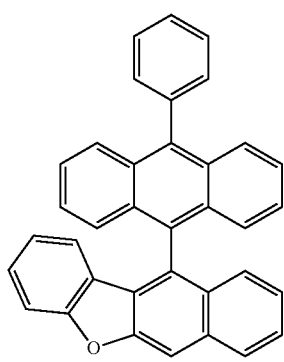
<Cpd. 262>
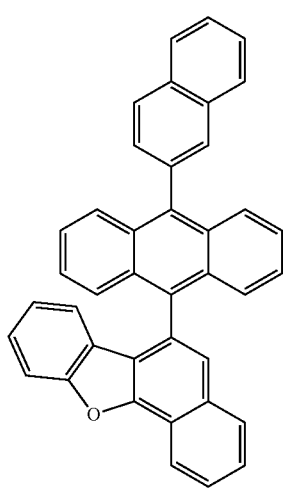
-continued
<Cpd. 263>
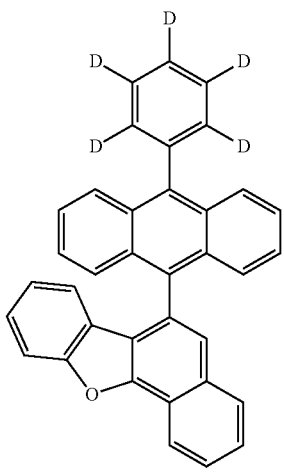
<Cpd. 264>
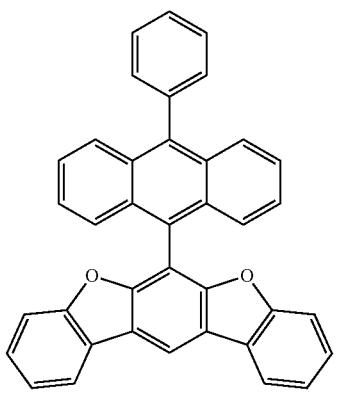
<Cpd. 265>
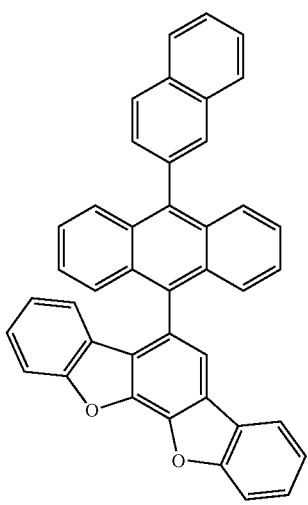

<Cpd. 266>
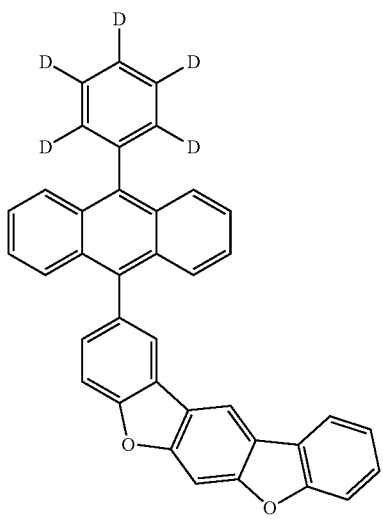
<Cpd. 267>
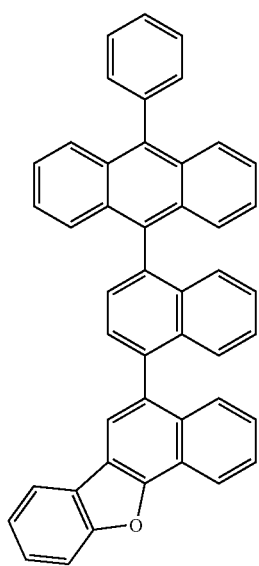
<Cpd. 268>
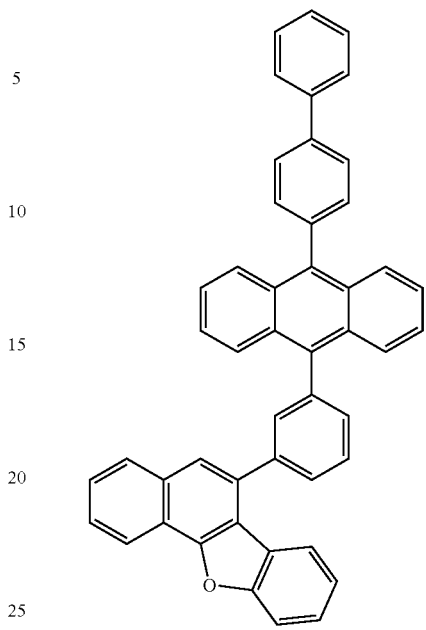
<Cpd. 269>
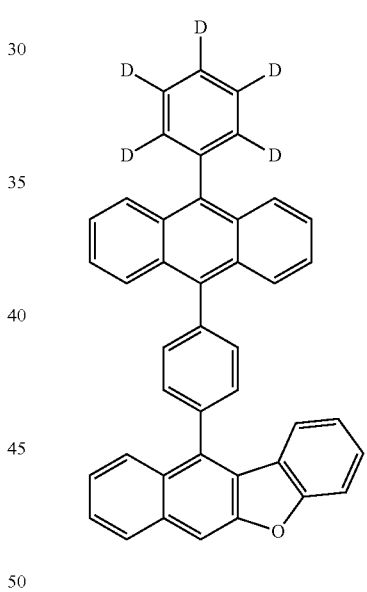
<Cpd. 270>
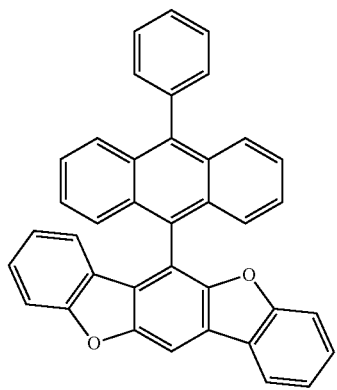

<Cpd. 271>

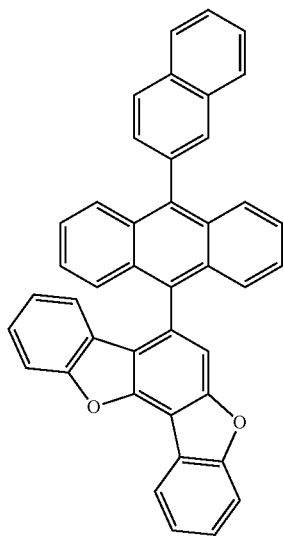

<Cpd. 272>

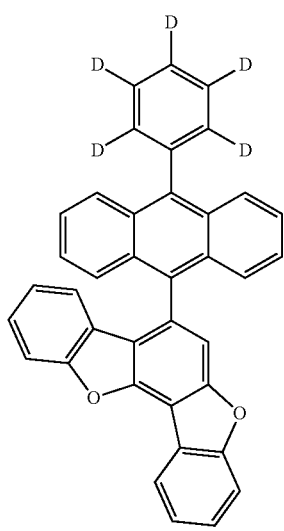

<Cpd. 273>

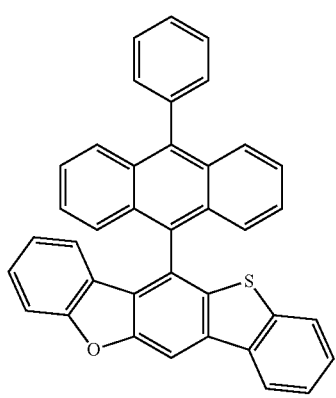

<Cpd. 274>

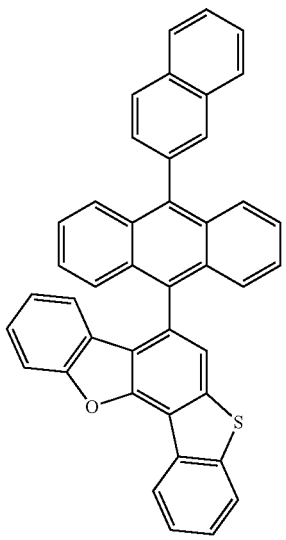

<Cpd. 275>

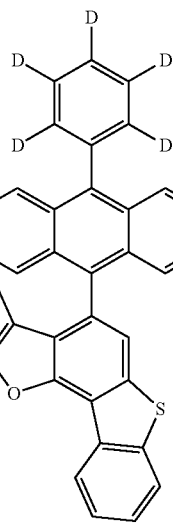

According to a particular embodiment thereof, the present disclosure provides an organic light-emitting diode, comprising: a first electrode; a second electrode facing the first electrode; a light-emitting layer interposed between the first electrode and the second electrode, wherein the light-emitting layer comprises at least one of the amine compounds represented by the following Chemical Formula A or B as a dopant, and at least one of the compounds represented by the following Chemical Formula C as a host.

According to some embodiments of the present disclosure, the content of the dopant in the light-emitting layer may range from about 0.01 to 20 parts by weight based on 100 parts by weight of the host, but is not limited thereto.

Also, the light-emitting layer may further comprise various dopant materials in addition to the dopant and the host.

When the amine compound represented by Chemical Formula A or B has suitable substituents in combination with a suitable host represented by Chemical Formula C in the light-emitting layer, the organic light-emitting diode can operate at a low voltage with high efficiency.

According to some particular embodiments of the present disclosure, the organic light-emitting diode may further comprise at least one of a hole injection layer, a hole transport layer, a functional layer capable of both hole injection and hole transport, an electron transport layer, and an electron injection layer in addition to the light-emitting layer Below, a description will be given of the organic light-emitting diode of the present disclosure, with reference to FIGURE.

FIGURE is a schematic cross-sectional view of the structure of an organic light-emitting diode according to some embodiments of the present disclosure.

As shown in FIGURE, the organic light-emitting diode has a structure in which a hole transport layer is interposed between a first electrode and a light-emitting layer and an electron transport layer is interposed between the light-emitting layer and a second electrode, that is, the organic light-emitting diode comprises an anode 20, a hole transport layer 40, an organic light-emitting layer 50 comprising a host and a dopant, an electron transport layer 60, and a cathode 80, sequentially.

Optionally a hole injection layer 30 and an electron injection layer 70 may be interposed between the anode 20 and the hole transport layer 40 and between the light-emitting layer 50 and the cathode 80, respectively.

Reference is now made to FIGURE with regard to the fabrication of the organic light-emitting diode of the present disclosure.

First, a substrate 10 is coated with an anode electrode material to form an anode 20. So long as it is used in a typical organic EL device, any substrate may be taken as the substrate 10. Preferable is an organic substrate or a transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO) may be used owing to their high transparency and electroconductivity.

A hole injection layer material is applied on the anode electrode 20 by thermal deposition in a vacuum or by spin coating to form a hole injection layer 30. Subsequently, thermal deposition in a vacuum or spin coating of a hole transport layer material may also be conducted to form a hole transport layer 40 on the hole injection layer 30.

No particular limitations are imposed on the hole injection layer material, as long as it is typically used in the art. A examples, mention may be made of 2-TNATA [4,4',4"-tris (2-naphthylphenyl-phenylamino)-triphenylamine], NPD [N,N'-di(1-naphthyl)-N,N'-diphenylbenzidine)], TPD [N,N'-diphenyl-N,N'-bis(3-methylphenyl)-1,1'-biphenyl-4,4'-diamine], and DNTPD [N,N'-diphenyl-N,N'-bis-[4-(phenyl-m-tolyl-amino)-phenyl]-biphenyl-4,4'-diamine].

So long as it is typically used in the art, any material may be selected for the hole transport layer without particular limitations. Examples include, but are not limited to, N,N'-bis(3-methylphenyl)-N,N'-diphenyl-[1,1-biphenyl]-4,4'-diamine (TPD) or N,N'-di(naphthalen-1-yl)-N,N'-diphenyl-benzidine (a-NPD).

Then, a light-emitting layer 50 may be deposited on the hole transport layer 40 by deposition in a vacuum or by spin coating.

Here, the light-emitting layer may consist of a host and a dopant, and the dopant and host materials are as mentioned above.

In some embodiments of the present disclosure, the light-emitting layer particularly ranges in thickness from 50 to 2,000 Å.

Thereafter, the electron transport layer 60 may be deposited on the light-emitting layer via vacuum deposition or spin coating, followed by forming the electron injection layer 70 on the electron transport layer 60 and then the cathode 80 on the electron injection layer 70, thereby fabricating an OLED.

So long as it functions to stably transport the electrons from the cathode, any known material may be used for the electron transport layer. Examples of the known electron transport material include quinoline derivatives, particularly tris(8-quinolinolate)aluminum (Alq3), Liq, TAZ, Balq, beryllium bis(benzoquinolin-10-oate: Bebq2), compound 201, compound 202, BCP, and the oxadiazole derivatives PBD, BMD, and BND, but are not limited thereto.

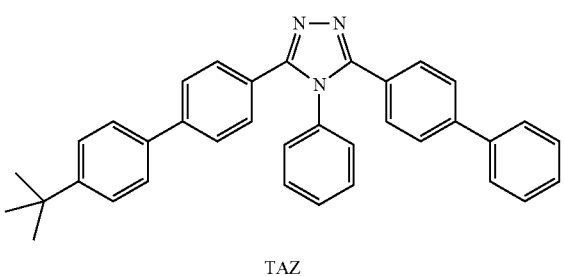

TAZ

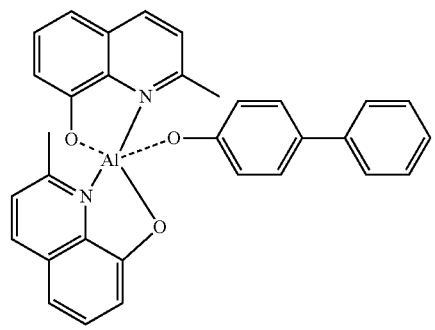

BAlq

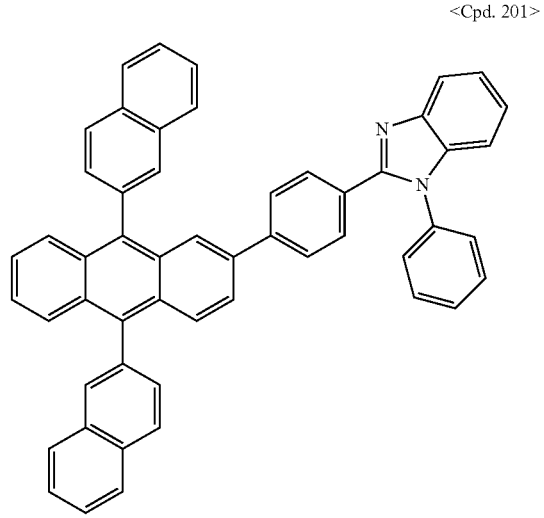

<Cpd. 201>

<Cpd. 202>

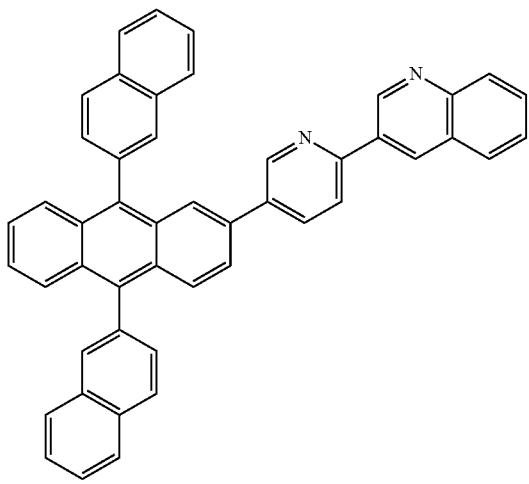

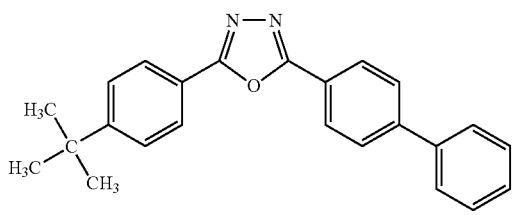
BCP

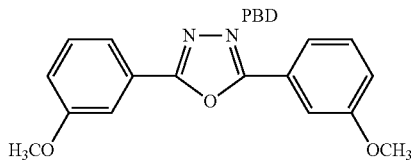
PBD

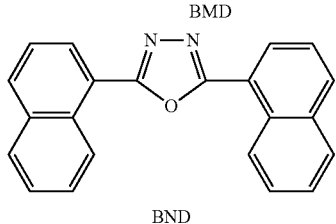
BMD

BND

As described above, an electron injection layer (EIL) is positioned on the electron transport layer in the organic light-emitting diode of the present disclosure. So long as it functions to facilitate the injection of electrons from the cathode, any known material may be available for forming the electron injection layer, without particular limitations.

By way of example, the material for the electron injection layer may be CsF, NaF, LiF, NaCl, $Li_2O$, or BaO. The conditions for depositing the electron injection layer are dependent on the compound that is employed, but may fall within the range of conditions for the formation of the hole injection layer.

The electron injection layer may range in thickness from about 1 Å to about 100 Å, and particularly from about 3 Å to about 90 Å. Given this thickness range, the electron injection layer can exhibit satisfactory electron injection properties without an actual increase in driving voltage.

The cathode may be made of a metal or metal alloy such as lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be employed to form a transparent cathode for a top-emitting organic light-emitting diode.

In another embodiment, the light-emitting diode of the present disclosure may further comprise a light-emitting layer, made of a blue light-emitting material, a green light-emitting material, or a red light-emitting material, which can emit light in a wavelength range of 380 nm to 800 nm. That is, the light-emitting layer in the organic light-emitting diode of the present disclosure may have a multilayer structure in which the additional blue, green, and/or red light-emitting layer may be made of a fluorescent or phosphorescent material.

Further, one or more layers selected from among the above-mentioned layers may be deposited using a single molecule deposition process or a solution process.

Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or white flat illumination devices, and monochrome or white flexible illumination devices.

A better understanding of the light-emitting diode according to the present disclosure may be obtained through the following examples which are set forth to illustrate, but are not to be construed as the limit of the present disclosure.

Synthesis Example 1: Synthesis of Compound of Chemical Formula 1

Synthesis Example 1-(1): Synthesis of Intermediate 1-a

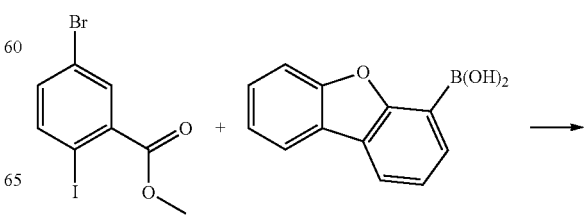

-continued

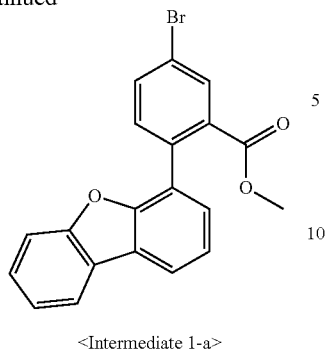
<Intermediate 1-a>

In a 500-mL round-bottom flask reactor, methyl 5-bromo-2-iodobenzoate (25.0 g, 73 mmol), 4-dibenzofuran boronic acid (18.7 g, 88 mmol), tetrakis (triphenylphosphine)palladium (1.7 g, 0.15 mmol), and potassium carbonate (20.2 g, 146.7 mmol) stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 1-a>. (75.0 g, 60.1%).

Synthesis Example 1-(2): Synthesis of [Intermediate 1-b]

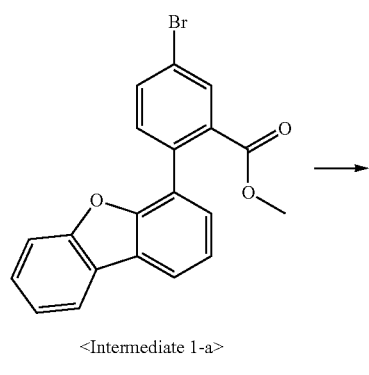
<Intermediate 1-a>

<Intermediate 1-b>

In a 500-mL round-bottom flask reactor, <Intermediate 1-a> (17.0 g, 45 mmol), sodium hydroxide (2.14 g, 54 mmol) and ethanol (170 ml) were stirred together for 48 hrs under reflux. After the completion of the reaction was confirmed by thin layer chromatography, the reaction mixture was cooled to room temperature. The chilled solution was acidified with drops of 2-N HCl, followed by stirring for 30 min. The solid thus formed was filtered, and recrystallized in dichloromethane and n-hexane to afford <Intermediate 1-b>. (14.5 g, 88.6%)

Synthesis Example 1-(3): Synthesis of [Intermediate 1-c]

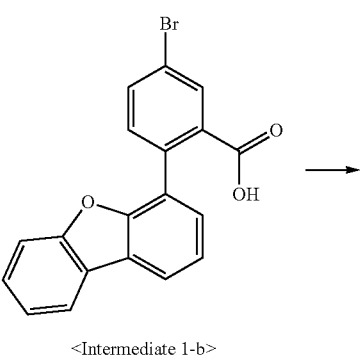
<Intermediate 1-b>

<Intermediate 1-c>

In a 250-mL round-bottom flask reactor, <Intermediate 1-b> (14.5 g, 39 mmol) and methanesulfonic acid (145 ml) were stirred together for 3 hrs at 80° C. After the completion of the reaction was confirmed by thin layer chromatography, the reaction mixture was cooled to room temperature and dropwise added to ice water (150 ml). After stirring for 30 min, the solid thus formed was filtered and washed with water and methanol to afford <Intermediate 1-c>. (11.50 g, 83.4%)

Synthesis Example 1-(4): Synthesis of [Intermediate 1-d]

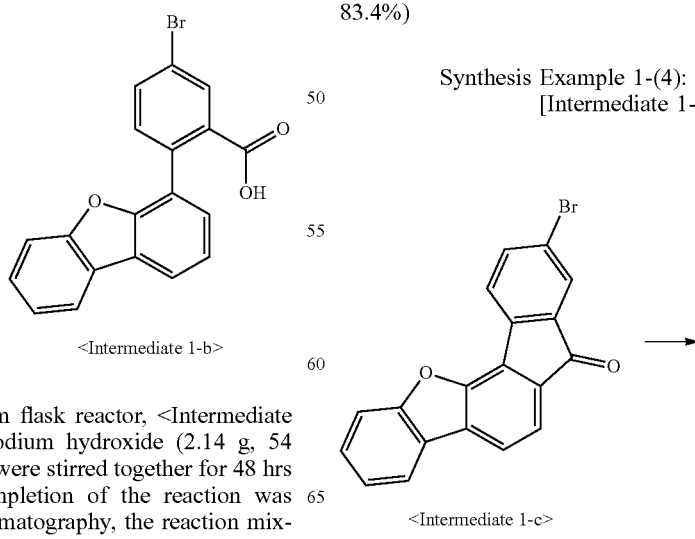
<Intermediate 1-c>

-continued

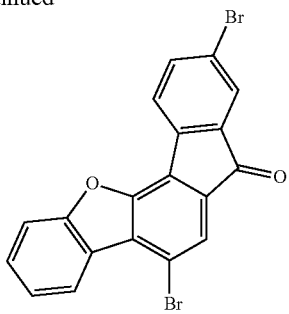
<Intermediate 1-d>

In a 1-L round-bottom flask reactor, <Intermediate 1-c> (11.5 g, 33 mmol> and dichloromethane (300 ml) were stirred together at room temperature. A dilution of bromine (3.4 ml, mmol) in dichloromethane (50 ml) was dropwise added, followed by stirring at room temperature for 8 hrs. After completion of the reaction, the reaction mixture was stirred together with acetone (100 ml). The solid thus formed was filtered, and washed with acetone. Recrystallization in monochlorobenzene afforded <Intermediate 1-d>. (11.0 g, 78%)

Synthesis Example 1-(5): Synthesis of [Intermediate 1-e]

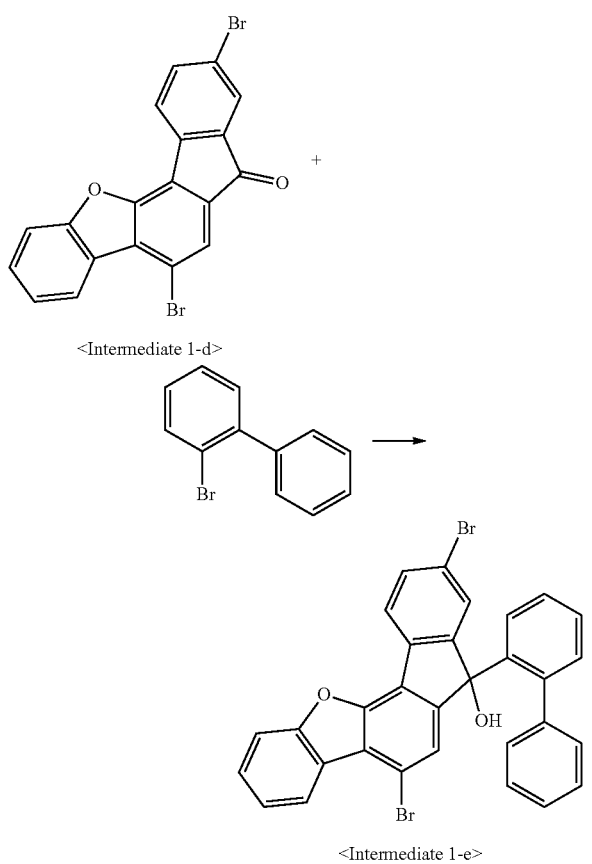

In a 250-ml round-bottom flask reactor, 2-bromobiphenyl (8.4 g, 0.036 mol) and tetrahydrofuran (110 ml) were chilled at −78° C. under a nitrogen atmosphere. At the same temperature, n-butyl lithium (19.3 ml, 0.031 mol) was dropwise added to the reaction solution which was then stirred for 2 hrs. Thereafter, <Intermediate 1-d> (11.0 g, 0.026 mol) was added little by little to the reaction solution, and stirred at room temperature. When the reaction mixture started to change color, the reaction was monitored via thin layer chromatography. After the reaction was stopped with H$_2$O (50 ml), extraction was conducted with ethylacetate and water. The organic layer was separated, concentrated in a vacuum, and recrystallized in acetonitrile to afford <Intermediate 1-e> as a solid. (12.2 g, 81.5%)

Synthesis Example 1-(6): Synthesis of [Intermediate 1-f]

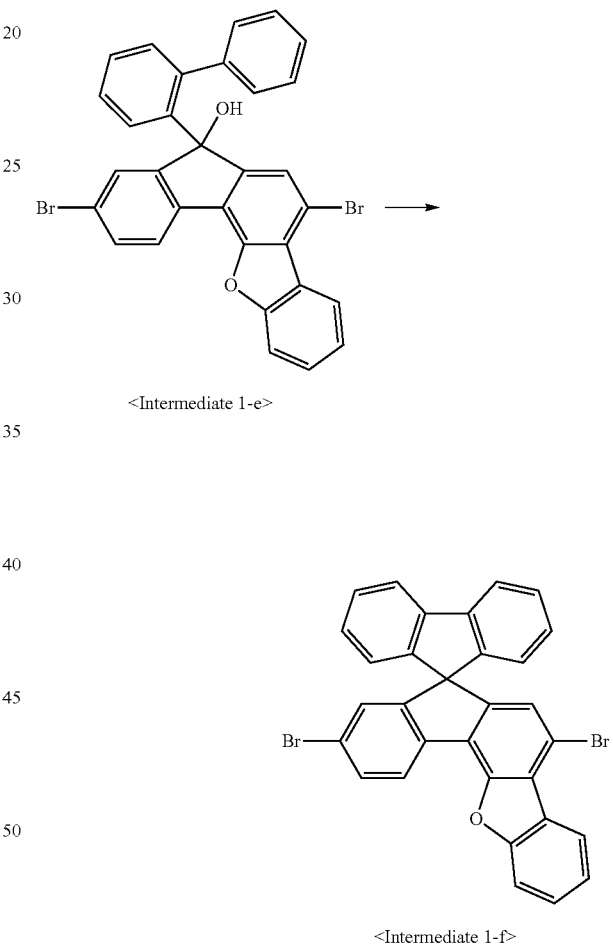

In a 250-ml round-bottom flask reactor, a mixture of <Intermediate 1-e> (12.0 g, 0.021 mol), acetic acid (120 ml), and sulfuric acid (2 ml) was stirred for 5 hrs under reflux. When a precipitate was formed, the completion of the reaction was monitored using thin layer chromatography. The reaction mixture was then cooled to room temperature and filtered. The filtrate was washed with H$_2$O and methanol and dissolved in monochlorobenzene. Following silica gel chromatography, the fraction was concentrated and cooled to room temperature to give <Intermediate 1-f>. (10.7 g, 90%>

Synthesis Example 1-(7): Synthesis of Compound of Chemical Formula 1

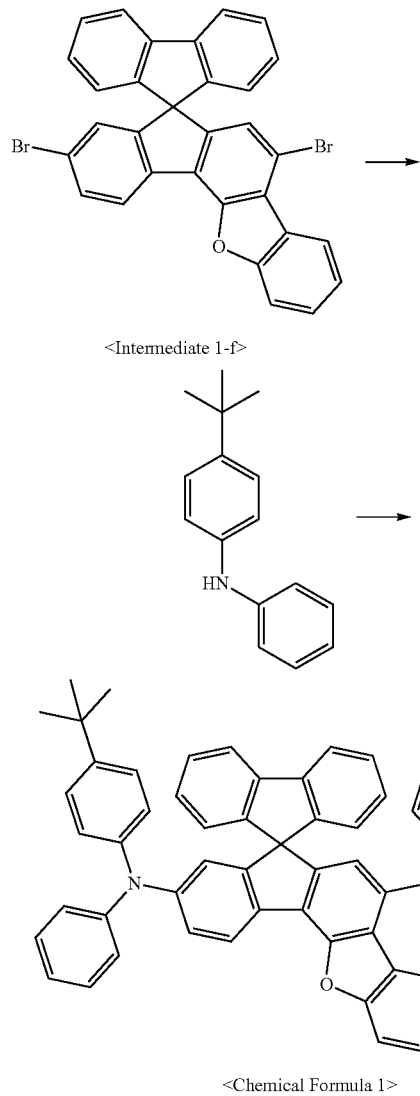

<Intermediate 1-f>

<Chemical Formula 1>

In a 250-ml round-bottom flask reactor, a mixture of <Intermediate 1-f> (5.0 g, 0.009 mol), (4-tert-butylphenyl)-phenylamine (4.7 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) were stirred together for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield the compound of Chemical Formula 1 as a solid (2.9 g, 38%).

MS (MALDI-TOF): m/z 852.41 [M+]

Synthesis Example: Synthesis of Compound of Chemical Formula 231

Synthesis Example 2-(1): Synthesis of Intermediate 2-a

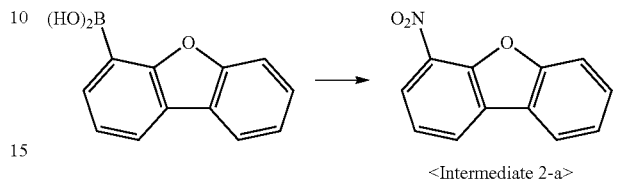

<Intermediate 2-a>

In a 1-L round-bottom flask reactor, dibenzofuran-4-bronic acid (85.0 g, 0.401 mol), bismuth (III) nitrate pentahydrate (99.2 g, 0.200 mol), and toluene (400 ml) were reacted at 70° C. for 3 hrs under a nitrogen atmosphere while stirring. After completion of the reaction, the reaction mixture was cooled to room temperature and washed with toluene. Filtration afforded <Intermediate 2-a> as a solid (61.5 g, 72%).

Synthesis Example 2-(2): Synthesis of Intermediate 2-b

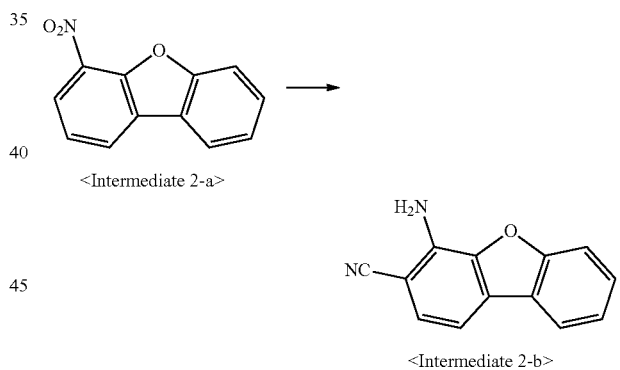

<Intermediate 2-a>

<Intermediate 2-b>

In a 2-L round-bottom flask reactor, ethylcyanoacetate (202.9 g, 1.794 mol), and dimethylformamide (500 ml) were added with potassium hydroxide (67.10 g, 1.196 mol), potassium cyanide (38.95 g, 0.598 mol), and dimethylformamide (200 ml), followed by stirring at room temperature. To this reaction solution, <Intermediate 2-a> (127.5 g, 0.737 mol) was slowly added while stirring at 50° C. for 72 hrs. After completion of the reaction, an aqueous sodium hydroxide solution (25%, 200 ml) was added, and stirred for 3 hrs under reflux. Subsequently, the reaction mixture was cooled to room temperature, followed by extraction with ether acetate and water. The organic layer was separated and concentrated. Purification by column chromatography afforded <Intermediate 2-b> (20.0 g, 16%).

Synthesis Example 2-(3): Synthesis of Intermediate 2-c

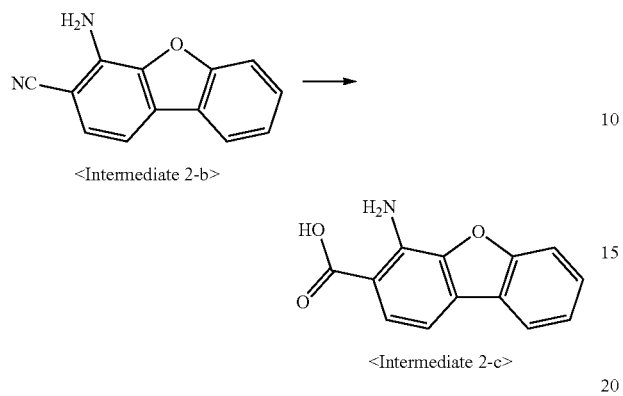

In a 2-L round-bottom flask reactor, <Intermediate 2-b> (20.0 g, 0.096 mol), ethanol (600 ml), and an aqueous solution (170 ml) of potassium hydroxide solution (142.26 g, 2.53 mol) were stirred for 12 hrs under reflux. After completion of the reaction, the reaction mixture was cooled to room temperature, and acidified with 6 N HCl (400 ml). Then, the reaction mixture was stirred for 20 min, and filtered. The filtrate was washed with ethanol to afford <Intermediate 2-c> as a solid (17.0 g, 88.5%).

Synthesis Example 2-(4): Synthesis of Intermediate 2-d

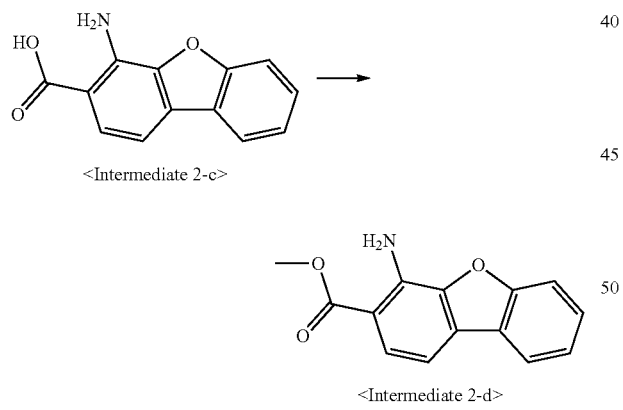

In a 2-L round-bottom flask reactor, <Intermediate 2-c> (17.0 g, 0.075 mol) and sulfuric acid (15 ml) were stirring together for 72 hrs under reflux. After completion of the reaction, the reaction mixture was cooled to room temperature and extracted with ethylacetate and water. The organic layer was separated, and washed with an aqueous sodium hydrogen carbonate solution. An excess of methanol was added during vacuum concentration, followed by filtration to afford <Intermediate 2-d> as a solid (14.0 g, 77.6%).

Synthesis Example 2-(5): Synthesis of Intermediate 2-e

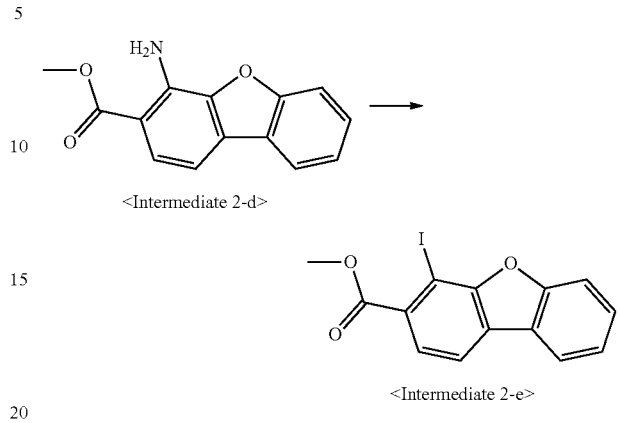

In a 500-mL round-bottom flask reaction, <Intermediate 2-d> (14.0 g, 0.058 mol), HCl (20 ml), and water (100 ml) were stirred together for 1 hr at 0° C. At the same temperature, an aqueous solution (50 ml) of sodium nitrite (7.4 g, 0.116 mol) was dropwise added to the reaction mixture and then stirred for 1 hr. An aqueous solution (100 ml) of potassium iodide (30.0 g, 0.180 mol) was dropwise added with care not to increase the temperature of the reaction solution above 5° C. Stirring was continued for 5 hrs at room temperature, and after completion of the reaction, the reaction mixture was washed with an aqueous sodium thiosulfate solution, and extracted with ethylacetate and water. The organic layer was separated and concentrated in a vacuum. Purification through column chromatography gave <Intermediate 2-e> (9.1 g, 48%).

Synthesis Example 2-(6): Synthesis of Intermediate 2-f

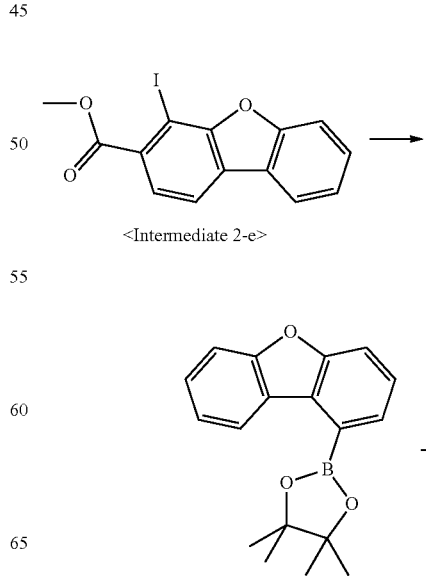

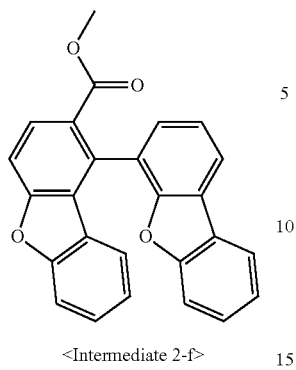

<Intermediate 2-f>

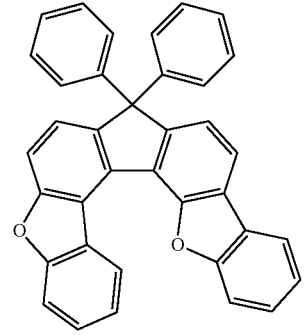

<Intermediate 2-g>

In a 250-mL round-bottom flask reactor, <Intermediate 2-e> (9.3 g, 25 mmol), 4-dibenzofuranborate (8.3 g, 28 mmol), tetrakis(triphenylphosphine)palladium (0.6 g, 0.05 mmol), and potassium carbonate (6.7 g, 50 mmol) were placed, and then toluene (50 mL), tetrahydrofuran (50 mL), and water (20 mL) were added. The temperature of the reactor was elevated to 80° C. before stirring for 10 hrs. After completion of the reaction, the temperature was cooled to room temperature, and extraction was conducted with ethylacetate. The organic layer thus formed was concentrated in a vacuum and purified by column chromatography to afford <Intermediate 2-f> (5.3 g, 52.3%).

Synthesis Example 2-(7): Synthesis of Intermediate 2-g

In a 500-ml round-bottom flask reactor, bromobenzene (25.5 g, 0.163 mol) and tetrahydrofuran (170 ml) were cooled to −78° C. in a nitrogen atmosphere. N-butyl lithium (95.6 ml, 0.153 mol) was dropwise added to the chilled solution, and stirred for 1 hr at the same temperature. Then, <Intermediate 4-f> (20.0 g, 0.051 mol) was added at room temperature while stirring. After completion of the reaction, the reaction mixture was stirred together with water (50 ml), and extraction with ethyl acetate and water was conducted. The organic layer was concentrated and the concentrate was mixed with acetic acid (200 ml) and HCl (1 ml) by stirring at 80° C. After completion of the reaction, the reaction mixture was cooled to room temperature, and the precipitate thus formed was filtered, and washed with methanol to afford <Intermediate 2-g> (20.0 g, 78%).

Synthesis Example 2-(8): Synthesis of Intermediate 2-h

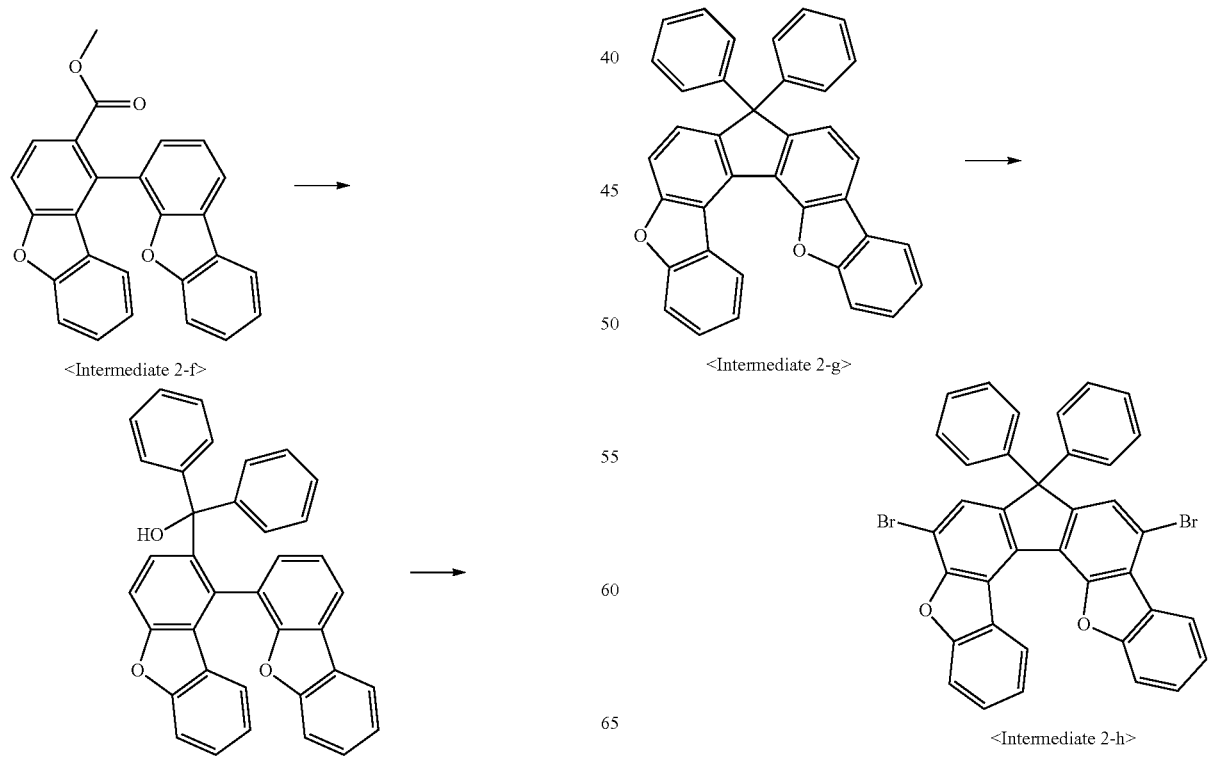

In a 100-mL round-bottom flask reactor, <Intermediate 2-g> (20 g, 58 mmol) and dichloromethane (40 ml) were stirred together at room temperature. A dilution of bromine (5.8 ml, 116 mmol) in dichloromethane (10 ml) was dropwise added, followed by stirring at room temperature for 8 hrs. After completion of the reaction, the reaction mixture was stirred together with acetone (20 ml). The solid thus formed was filtered, and washed with acetone. Recrystallization in monochlorobenzene afforded <Intermediate 2-h> (15.8 g, 55%)

Synthesis Example 2-(9): Synthesis of Compound of Chemical 231

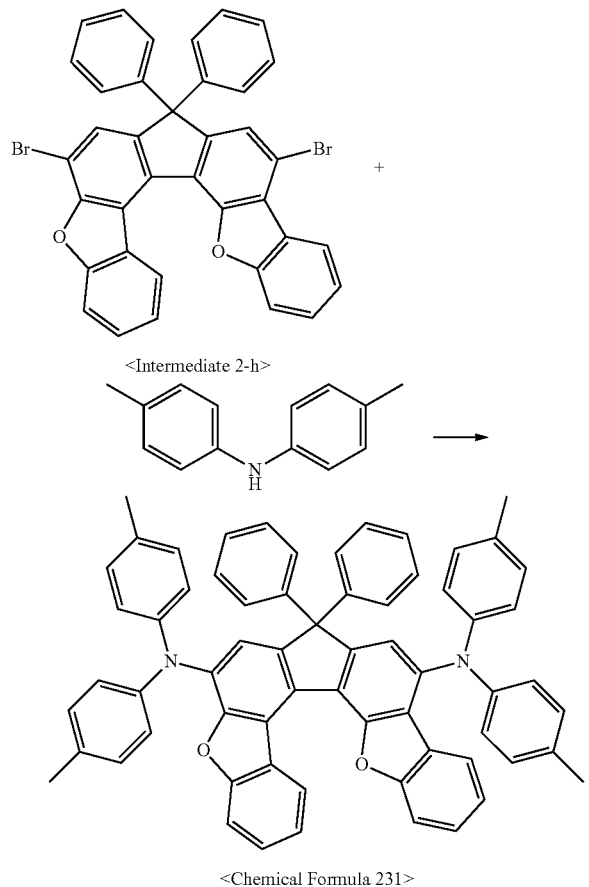

<Chemical Formula 231>

In a 100-ml round-bottom flask reactor, a mixture of <Intermediate 2-h> (4.0 g, 0.006 mol), di-p-tollylamine (3.2 g, 0.016 mol), palladium (II) acetate (0.08 g, 0.4 mmol), sodium tert-butoxide (3.2 g, 0.032 mol), tri-tert-butyl phosphine (0.08 g, 0.4 mmol), and toluene (50 ml) were stirred together for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield <Chemical Formula 231> as a solid (2.1 g, 41%).

MS (MALDI-TOF): m/z 888.37 [M$^+$]

Synthesis Example 3: Synthesis of Compound 207

Synthesis Example 3-(1): Synthesis of Intermediate 3-a

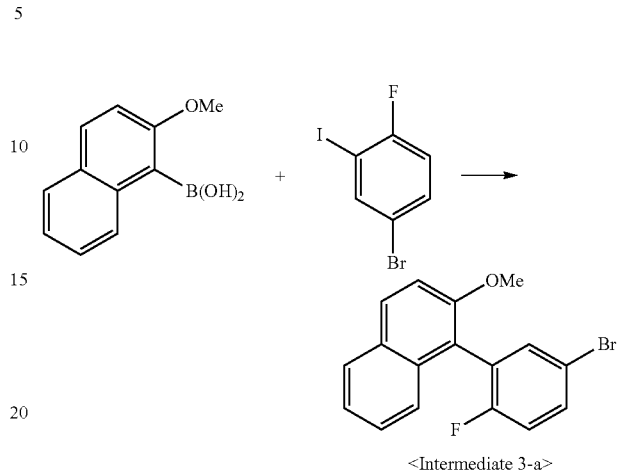

<Intermediate 3-a>

In a 2-L round-bottom flask reactor, 2-methoxynaphthalene-1-boronic acid (100.0 g, 495 mmol), 2-fluoro-5-bromoiodobenzene (141.0 g, 470 mmol), tetrakis(tripheneylphosphine)palladium (10.8 g, 9.4 mmol), and potassium carbonate (68.4 g, 495 mmol) were stirred overnight, together with toluene (500 mL), methanol (500 mL) and water (300 mL) under reflux. After completion of the reaction, the reaction mixture was cooled to room temperature and extracted with ethyl acetate. The organic layer thus formed was separated, and concentrated in a vacuum, followed by column chromatography. Recrystallization in heptanes afforded <Intermediate 3-a> (84.0 g, 54%).

Synthesis Example 3-(2): Synthesis of Intermediate 3-b

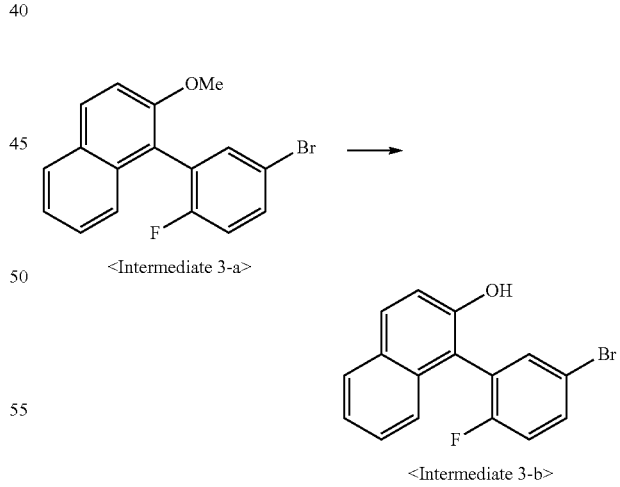

<Intermediate 3-b>

In a 2-L round-bottom flask reactor, <Intermediate 3-a> (84.0 g, 253 mmol) was dissolved in dichloromethane (840 ml). After the temperature was cooled to 0° C., boron tribromide (63.3 g, 253 mmol) was dropwise added to the solution and then stirred at room temperature for 24 hrs. After completion of the reaction, the reaction mixture was cooled to −78° C. and then added with drops of methanol (300 ml). The temperature was elevated to room temperature

Synthesis Example 3-(3): Synthesis of Intermediate 3-c

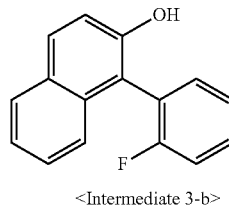

<Intermediate 3-b>

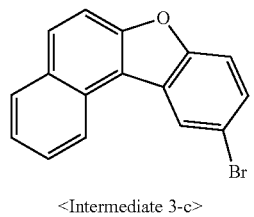

<Intermediate 3-c>

In a 2-L round-bottom flask reactor, <Intermediate 3-b> (73.0 g, 230 mmol) and potassium carbonate (63.6 g, 460 mmol) were dissolved in N-methyl-2-pyrrolidinone (730 ml), and then stirred for 2 hrs under reflux at 180° C. After completion of the reaction, the reaction mixture was cooled to room temperature. Concentration in a vacuum was followed by column chromatography. Recrystallization in methylene chloride and heptanes afforded <Intermediate 3-c> (40.4 g, 59%).

Synthesis Example 3-(4): Synthesis of Compound 207

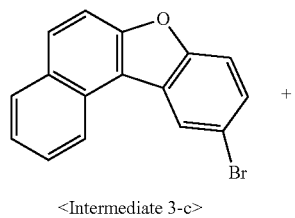

<Intermediate 3-c>

+

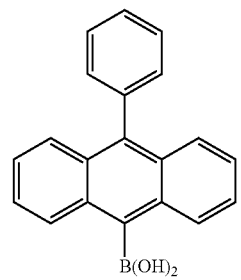

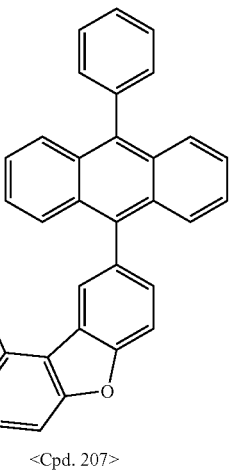

<Cpd. 207>

In a 250-mL round-bottom flask reactor, <Intermediate 3-c> (10.0 g, 33.7 mmol), 10-phenyl-anthracene-9-boronic acid (11.0 g, 37 mmol), tetrakis(triphenylphosphine)palladium (0.8 g, 0.7 mmol), and potassium carbonate (9.3 g, 68 mmol) were placed, followed by toluene (50 mL), ethanol (50 mL) and water (30 mL). The mixture was heated to 90° C. and stirred overnight. After completion of the reaction, the reaction mixture was cooled to room temperature, and stirred together with methanol (50 ml). The precipitate thus formed was filtered and washed with methanol. Recrystallization in toluene and acetone afforded <Cpd. 207> as a solid.

MS (MALDI-TOF): m/z 470.17 [M$^+$]

Synthesis Example 4: Synthesis of Compound 209

Synthesis Example 4-(1): Synthesis of Compound 209

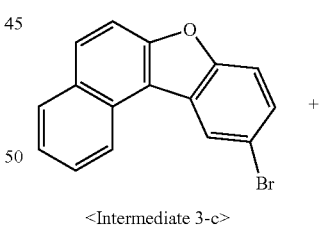

<Intermediate 3-c>

+

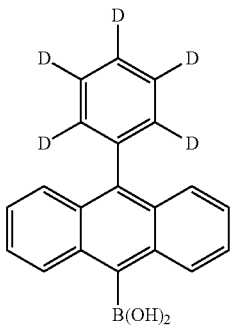

133
-continued

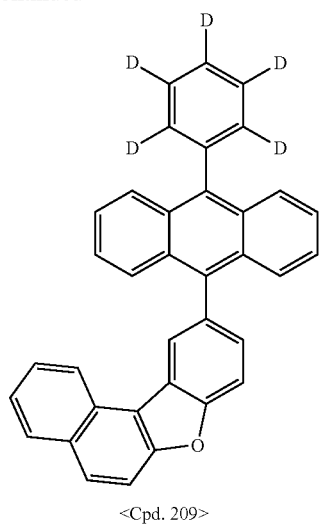
<Cpd. 209>

<Compound 209> was synthesized in the same manner as in Synthesis Example 3-(4), with the exception that 10-phenyl(d5)-anthracene-9-boronic acid was used instead of 10-phenyl-anthracene-9-boronic acid.

MS (MALDI-TOF): m/z 475.20 [M$^+$]

Synthesis Example 5: Synthesis of Compound 219

Synthesis Example 5-(1): Synthesis of Intermediate 5-a

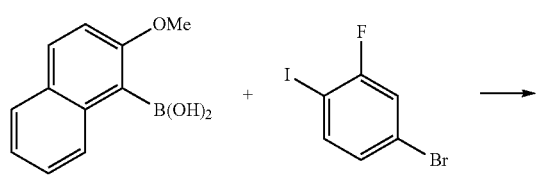

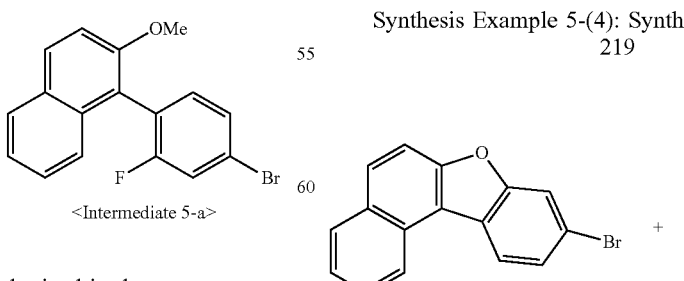
<Intermediate 5-a>

<Intermediate 5-a> was synthesized in the same manner as in Synthesis Example 3-(1), with the exception that 2-fluoro-4-bromoiodobenzene was used instead of 2-fluoro-5-bromoiodobenzene.

134

Synthesis Example 5-(2): Synthesis of Intermediate 5-b

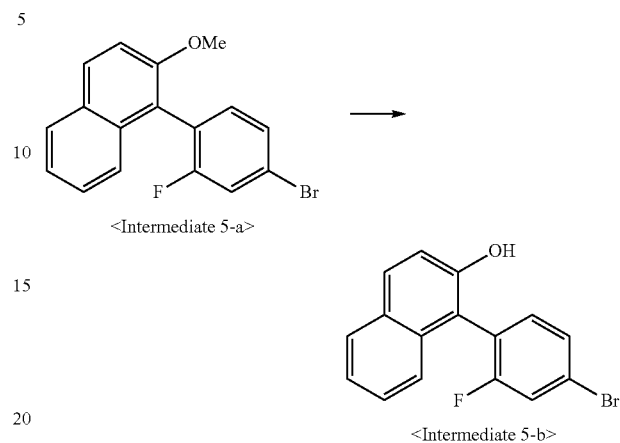

<Intermediate 5-b> was synthesized in the same manner as in Synthesis Example 3-(2), with the exception that <Intermediate 5-a> was used instead of <Intermediate 3-a>.

Synthesis Example 5-(3): Synthesis of Intermediate 5-c

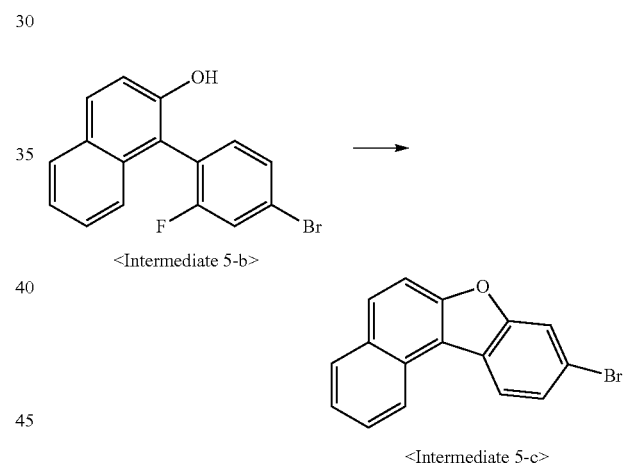

<Intermediate 5-c> was synthesized in the same manner as in Synthesis Example 3-(3), with the exception that <Intermediate 5-b> was used instead of 1<Intermediate 3-b>.

Synthesis Example 5-(4): Synthesis of Compound 219

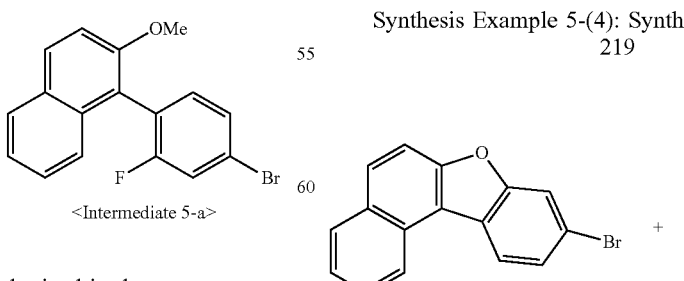
<Intermediate 5-c>

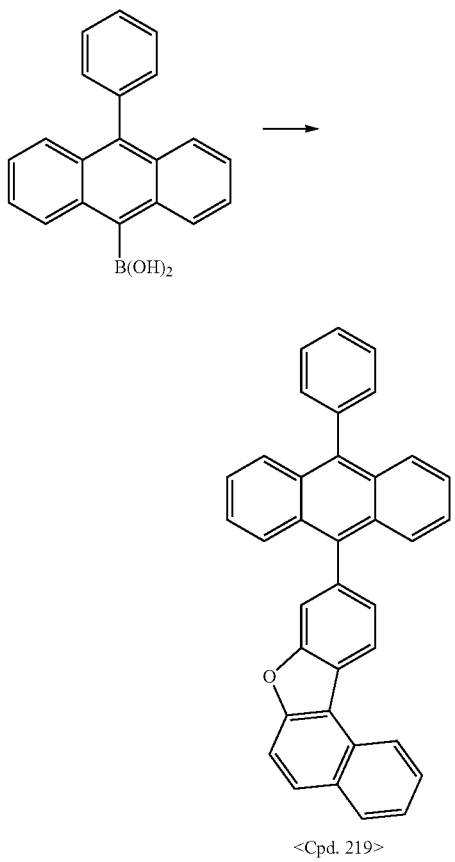

<Cpd. 219>

<Compound 219> was synthesized in the same manner as in Synthesis Example 3-(4), with the exception that <Intermediate 5-c> was used instead of <Intermediate 3-c>.

MS (MALDI-TOF): m/z 470.17 [M⁺]

Synthesis Example 6: Synthesis of Compound 213

Synthesis Example 6-(1): Synthesis of Compound 213

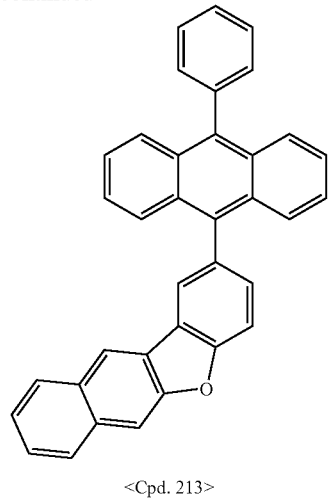

<Cpd. 213>

<Compound 213> was synthesized in the same manner as in Synthesis Example 3-(4), with the exception that 2-bromonaphtho[2,3-b]benzene was used instead of <Intermediate 3-c>.

MS (MALDI-TOF): m/z 470.17 [M⁺]

Examples 1 to 8: Fabrication of Organic Light-Emitting Diodes

An ITO glass substrate was patterned to have a translucent area of 2 mm×2 mm and cleansed. The ITO glass was mounted in a vacuum chamber that was then set to have a base pressure of 1×10⁻⁷ torr. On the ITO glass substrate, films were formed of DNTPD (400 Å) and α-NPD (200 Å) in that order. A light-emitting layer (200 Å) was formed of a mixture of a host and a dopant (w/w 97:3) as shown in Table 1, below. Then, [Chemical Formula E-1] was deposited to form an electron transport layer 300 Å thick, on which an electron injection layer (5 Å) was formed of [Chemical Formula E-2] and then covered with an Al layer (1000 Å) to fabricate an organic light-emitting diode.

The organic light-emitting diode thus obtained was measured at 10 mA/cm² for luminescence properties.

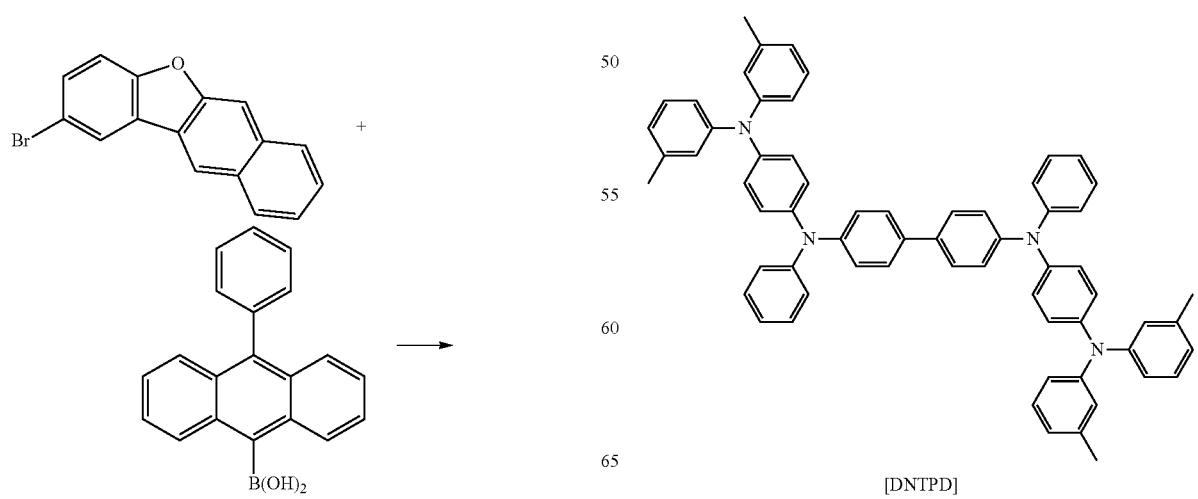

[DNTPD]

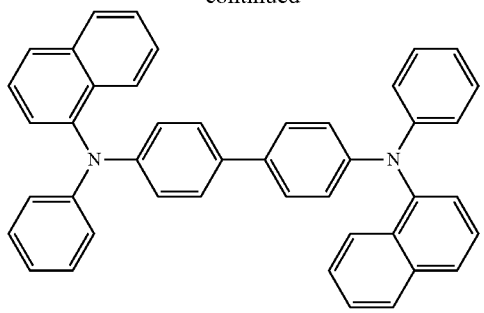

[α-NPD]

[Chemical Formula E-1]

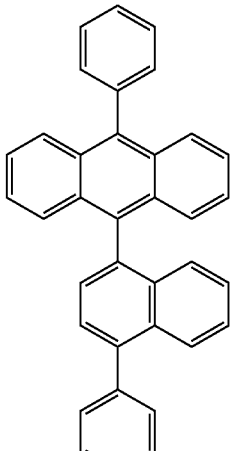

[BH]

TABLE 1

| Ex. # | Dopant | Host | V | lm/W | CIEx | CIEy |
|---|---|---|---|---|---|---|
| 1 | Chemical Formula 1 | Cpd. 207 | 3.3 | 8.2 | 0.137 | 0.115 |
| 2 | Chemical Formula 1 | Cpd. 209 | 3.3 | 8.2 | 0.137 | 0.114 |
| 3 | Chemical Formula 1 | Cpd. 213 | 3.3 | 8.4 | 0.137 | 0.117 |
| 4 | Chemical Formula 1 | Cpd. 219 | 3.2 | 8.3 | 0.137 | 0.111 |
| 5 | Chemical Formula 231 | Cpd. 207 | 3.3 | 8.7 | 0.136 | 0.122 |
| 6 | Chemical Formula 231 | Cpd. 209 | 3.3 | 8.7 | 0.136 | 0.115 |
| 7 | Chemical Formula 231 | Cpd. 213 | 3.3 | 8.8 | 0.136 | 0.114 |
| 8 | Chemical Formula 231 | Cpd. 219 | 3.3 | 8.2 | 0.136 | 0.121 |
| C. 1 | Chemical Formula 1 | BH | 3.9 | 6.9 | 0.138 | 0.107 |
| C. 2 | Chemical Formula 231 | BH | 3.9 | 7.2 | 0.138 | 0.108 |

As is understood from the data of Table 1, the organic light-emitting diodes of the present disclosure exhibited lower driving voltages and higher luminous efficiency (1 m/V) than the organic light-emitting diodes using the compounds of Comparative Examples 1 and 2, thereby demonstrating their high applicability to organic electroluminescence devices.

Therefore, the organic light-emitting diode according to the present disclosure can operate at lower voltages with higher efficiency than those of the conventional arts.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An organic light-emitting diode, comprising:
a first electrode;
a second electrode facing the first electrode; and
a light-emitting layer interposed between the first electrode and the second electrode,
wherein the light-emitting layer comprises at least one of the amine compounds represented by the following Chemical Formula B, and the compound represented by the following Chemical Formula C:

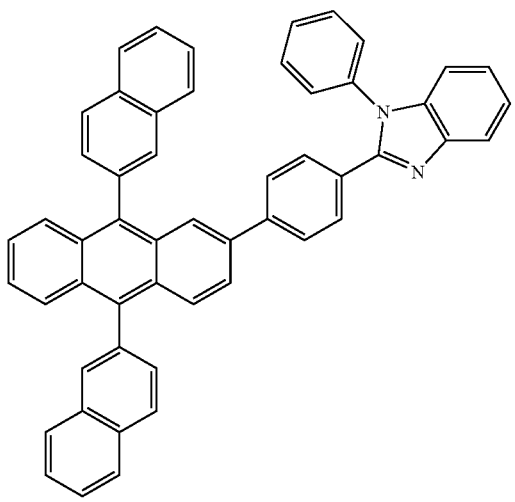

[Chemical Formula E-2]

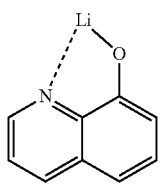

Comparative Examples 1 and 2

Organic light-emitting diodes were fabricated in the same manner as in Examples 1 to 8, with the exception that [BD1] was used as a host in a light-emitting layer. Luminescence properties of the organic light-emitting diodes were measured at 10 mA/cm². The structure of [BD1] is as follows.

[Chemical Formula B]

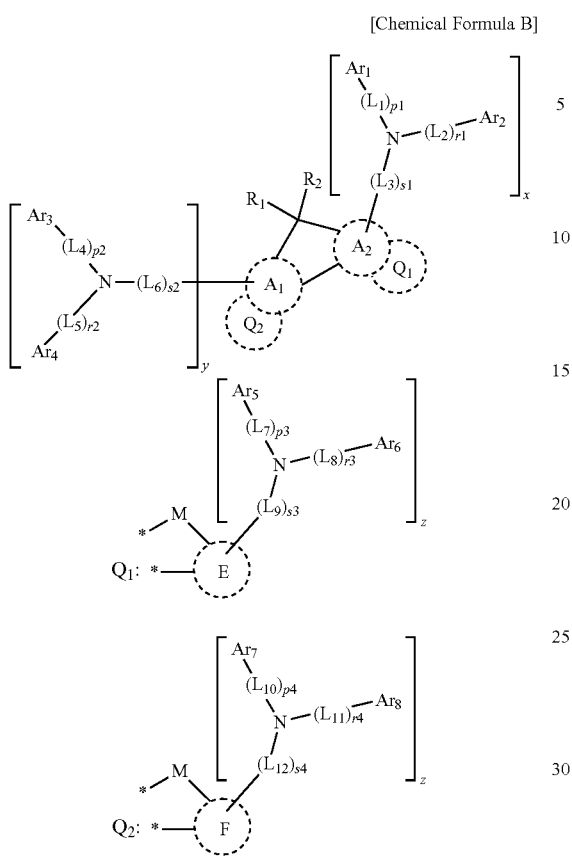

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring Ai and two adjacent carbon atoms of the aromatic ring $A_2$ form a 5-membered fused ring together with a carbon atom to which the substituents $R_1$ and $R_2$ are bonded;

linkers $L_1$ to $L_{12}$ may be the same or different, and are each independently a direct bond or a substituted or unsubstituted arylene of 6 to 60 carbon atoms;

M is any one selected from among N-$R_3$, $CR_4R_5$, O, and S;

$R_1$ to $R_5$, and $Ar_1$ to $Ar_8$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, a substituted or unsubstituted arylsilyl of 6 to 30 carbon atoms, a cyano, a nitro, and a halogen, with the proviso that $R_1$ and $R_2$ together may form a mono- or polycyclic aliphatic or aromatic ring, which may be a heterocyclic ring containing a heteroatom selected from among N, O, P, Si, and S as a ring member;

p1 to p4, $R_1$ to $R_4$, and s1 to s4 are each independently an integer of 1 to 3, with the proviso that when any of them is 2 or greater, the corresponding linkers may be the same or different, x is 1, and y and z may be the same or different, and are each independently an integer of 0 or 1; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$, and two adjacent carbon atoms of the Ai ring moiety of Chemical Formula B may occupy respective positions * of structural Formula $Q_2$ to form a fused ring,

[Chemical Formula C]

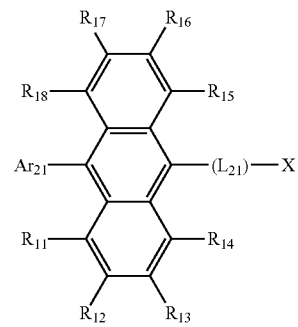

wherein, $Ar_{21}$ is selected from among a substituted or unsubstituted aryl of 6 to 50 carbon atoms, and a substituted or unsubstituted heteroaryl of 3 to 50 carbon atoms containing O, N or S as a heteroatom:

$L_{21}$ is a single bond or a substituted or unsubstituted arylene of 6 to 50 carbon atoms;

$R_{11}$ and $R_{18}$ may be the same or different, and are each independently selected from the group consisting of hydrogen, deuterium, a substituted or unsubstituted alkyl of 1 to 30 carbon atoms, a substituted or unsubstituted cycloalkyl of 3 to 30 carbon atoms, a substituted or unsubstituted aryl of 6 to 50 carbon atoms, a substituted or unsubstituted heteroaryl of 3 to 50 carbon atoms containing O, N or S as a heteroatom, a nitrile, a nitro, and a halogen;

$R_{12}$ and $R_{16}$ may form a saturated or unsaturated ring with $R_{13}$ and $R_{17}$, respectively X is a substituent represented by the following Structural Formula A,

[Structural Formula A]

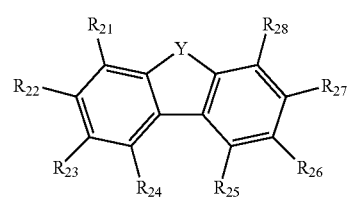

P1

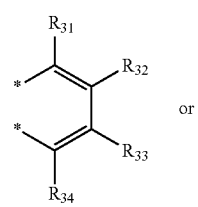

-continued

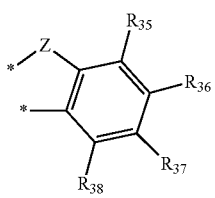

P2 wherein,

Y and Z may be the same or different, and are each independently an oxygen atom or a sulfur atom, $R_{21}$ to $R_{38}$ may be the same or different, and are each independently selected from among a hydrogen atom, a deuterium atom, a substituted or unsubstituted alkyl of 1 to 30 carbon atoms, a substituted or unsubstituted cycloalkyl of 1 to 30 carbon atoms, a substituted or unsubstituted aryl of 6 to 50 carbon atoms, a cyano, and a halogen, two adjacent substituents of $R_{21}$ to $R_{24}$ occupy respective positions '*' of P1 or P2, and any one substituent of $R_{25}$ to $R_{28}$ represents a single bond connected to the linker $L_{21}$, wherein the term 'substituted' in the expression 'substituted or unsubstituted' for Chemical Formulas B and C means having at least one substituent selected from the group consisting of a deuterium, a cyano, a halogen, a nitro, an alkyl of 1 to 24 carbon atoms, a halogenated alkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkylsilyl of 1 to 24 carbon atoms, and an arylsilyl of 6 to 24 carbon atoms.

2. The organic light-emitting diode of claim 1, wherein the light-emitting layer comprises a host and a dopant, the amine compound of Chemical Formula B serving as the dopant, the compound of Chemical Formula C serving as the host.

3. The organic light-emitting diode of claim 1, wherein $A_1$, $A_2$, E, and F of Chemical Formula B may be identical or different, and are each independently a substituted or unsubstituted aromatic hydrocarbon ring of 6 to 50 carbon atoms.

4. The organic light-emitting diode of claim 3, wherein the substituted or unsubstituted aromatic hydrocarbon ring of 6 to 50 carbon atoms is selected from among compounds represented by [Structural Formula 10] to [Structural Formula 21]:

[Structural Formula 10]

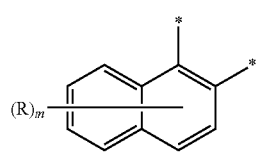

[Structural Formula 11]

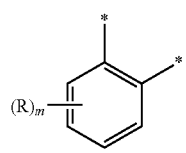

[Structural Formula 12]

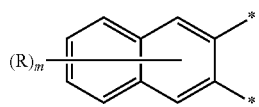

[Structural Formula 13]

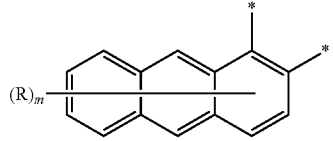

[Structural Formula 14]

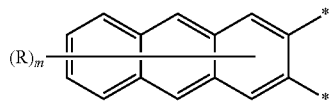

[Structural Formula 15]

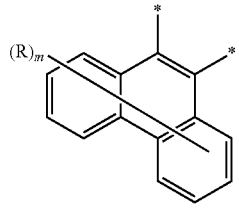

[Structural Formula 16]

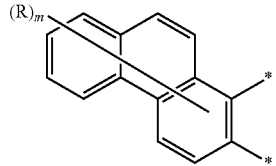

[Structural Formula 17]

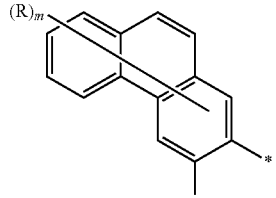

[Structural Formula 18]

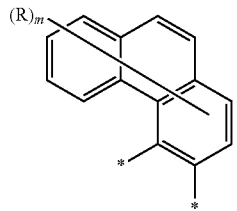

[Structural Formula 19]

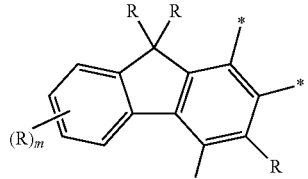

[Structural Formula 20]

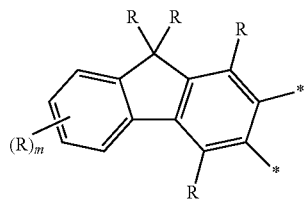

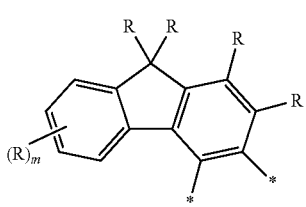

[Structural Formula 21]

[Structural Formula 19] [Structural Formula 20] [Structural Formula 21]

wherein,

"-*" denotes a bonding site for forming a 5-membered ring containing the carbon atom connected to both the substituents $R_1$ and $R_2$, or a bonding site for forming a 5-membered ring containing M of the structural Formula $Q_1$ and $Q_2$ with moiety $A_I$ or $A_2$, when one of the aromatic hydrocarbon rings of [Structural Formula 10] to [Structural Formula 21] for $A_I$ or Az is bonded to Structural Formula Qi or Structural Formula $Q_2$, two adjacent carbon atoms of the aromatic hydrocarbon ring occupy respective positions * of Structural Formula $Q_1$ or $Q_2$ to form a fused ring; and R is selected from the group consisting of hydrogen, a deuterium, a cyano, a halogen, a nitro, an alkyl of 1 to 24 carbon atoms, an aryl of 6 to 24 carbon atoms, an arylalkyl of 7 to 24 carbon atoms, a heteroaryl of 2 to 24 carbon atoms, a heteroarylalkyl of 2 to 24 carbon atoms, an alkylsilyl of 1 to 24 carbon atoms, and an arylsilyl of 6 to 24 carbon atoms, m is an integer of 1 to 8, with the proviso that when m is 2 or greater or two or more R's exist, the corresponding R's may be the same or different.

5. The organic light-emitting diode of claim 1, wherein the substituent Aril on the compound of Chemical Formula C is a compound represented by the following Chemical Formula C-1:

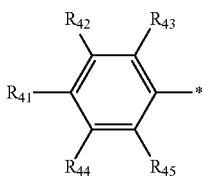

[Chemical Formula C-1]

wherein, $R_{41}$ to $R_{45}$ may be the same or different, and are each as defined for $R_{11}$ to $R_{18}$ in claim 1; and may form a saturated or unsaturated ring with respective adjacent substituents.

6. The organic light-emitting diode of claim 1, wherein the linkers $L_1$ to $L_{12}$ of Chemical Formula B represent single bonds, or are each any one selected from the following [Structural Formula 22], [Structural Formula 23], [Structural Formula 25], [Structural Formula 27], [Structural Formula 28], and [Structural Formula 30], p1 to p4, r1 to r4, and s1 to s4 are each 1 or 2, and x is 1:

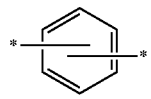

[Structural Formula 22]

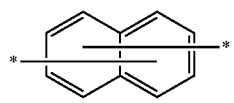

[Structural Formula 23]

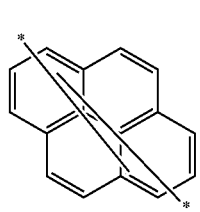

[Structural Formula 25]

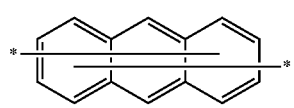

[Structural Formula 27]

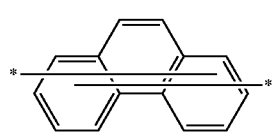

[Structural Formula 28]

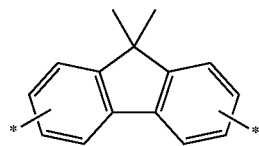

[Structural Formula 30]

wherein hydrogen or deuterium may be positioned on a carbon atom as a member in aromatic rings of the linkers.

7. The organic light-emitting diode of claim 1, wherein the linker $L_{21}$ in Chemical Formula C is a single bond.

8. The organic light-emitting diode of claim 1, wherein x and y are each 1 and z is 0 in Chemical Formula B.

9. The organic light-emitting diode of claim 1, wherein the amine compound is any one selected from among the compounds represented by [Chemical Formula 25] to [Chemical Formula 32], [Chemical Formula 85], [Chemical Formula 91], [Chemical Formula 92], [Chemical Formula 97], [Chemical Formula 98], [Chemical Formula 102], [Chemical Formula 117], [Chemical Formula 142] to [Chemical Formula 149], [Chemical Formula 160], [Chemical Formula 162], [Chemical Formula 164], [Chemical Formula 165], [Chemical Formula 197] to [Chemical Formula 201], [Chemical Formula 210], [Chemical Formula 222] to [Chemical Formula 224], [Chemical Formula 227] to [Chemical Formula , [Chemical Formula 239]:

<Chemical Formula 25>
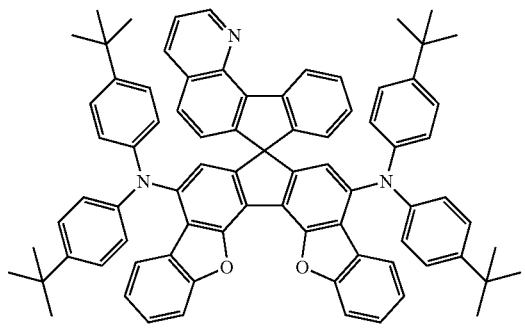
<Chemical Formula 26>
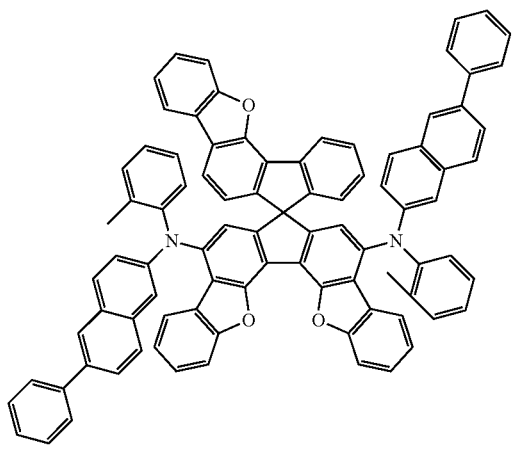
<Chemical Formula 27>
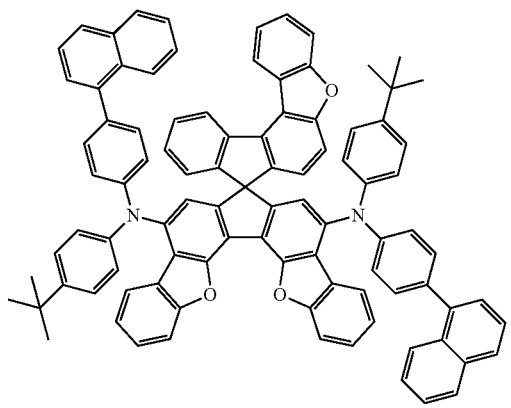
<Chemical Formula 28>
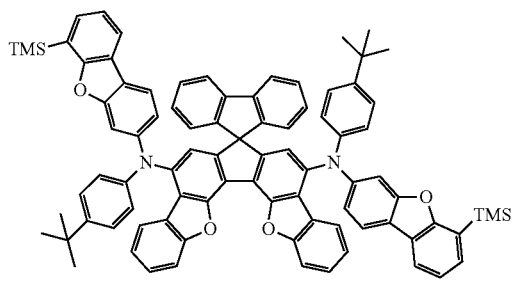
<Chemical Formula 29>
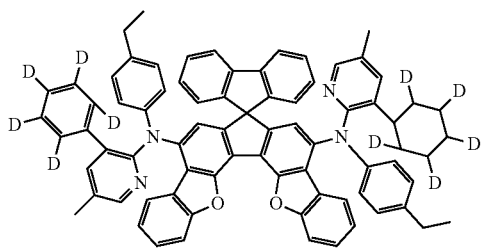
<Chemical Formula 30>
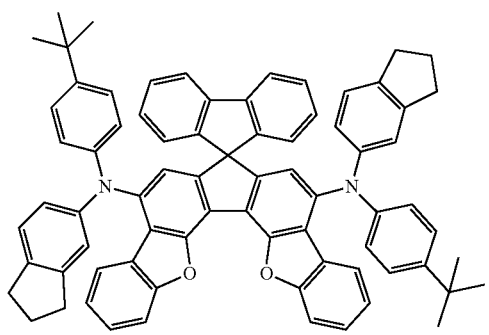
<Chemical Formula 31>
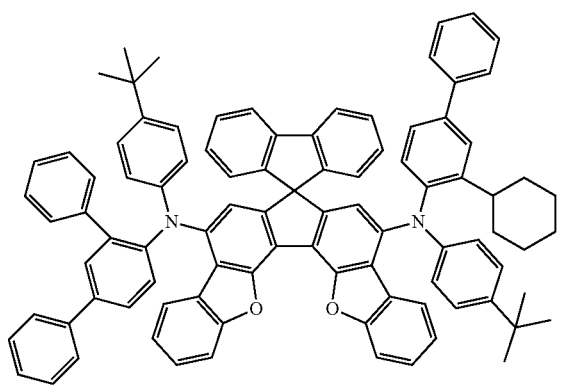

<Chemical Formula 32>
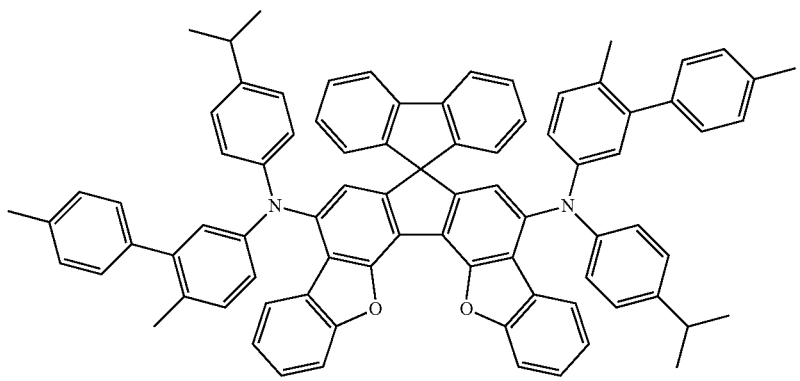
<Chemical Formula 85>
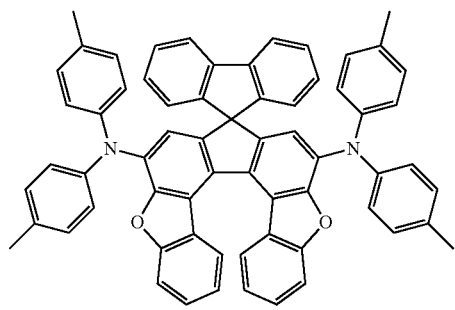
<Chemical Formula 91>
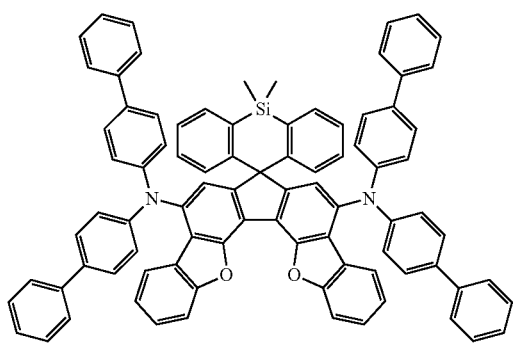
<Chemical Formula 92>
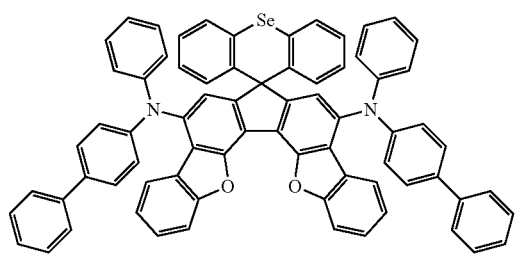
<Chemical Formula 97>
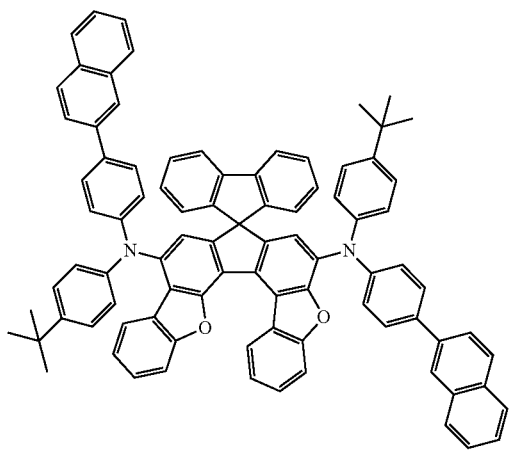
<Chemical Formula 98>
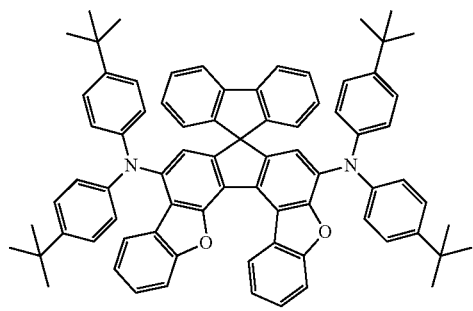

-continued
<Chemical Formula 102>
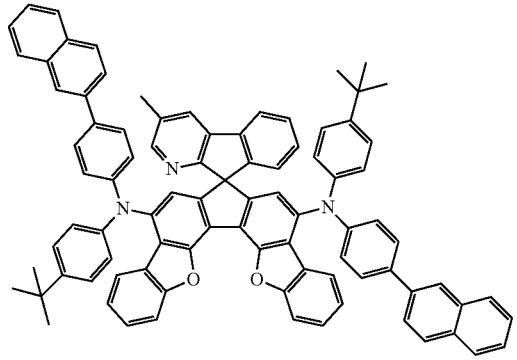
<Chemical Formula 117>
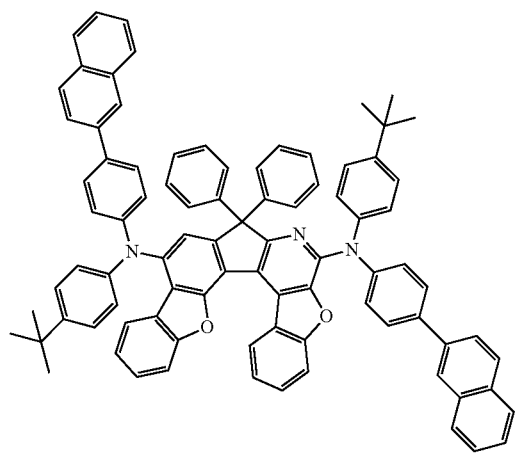
<Chemical Formula 142>
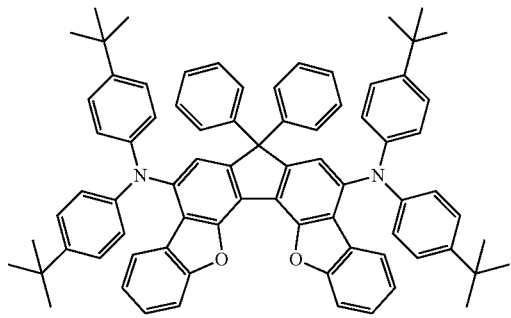
<Chemical Formula 143>
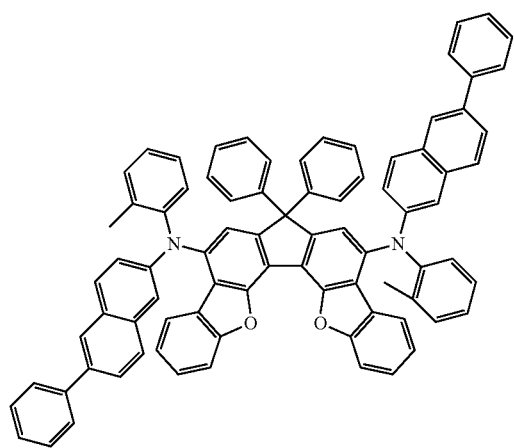
<Chemical Formula 144>
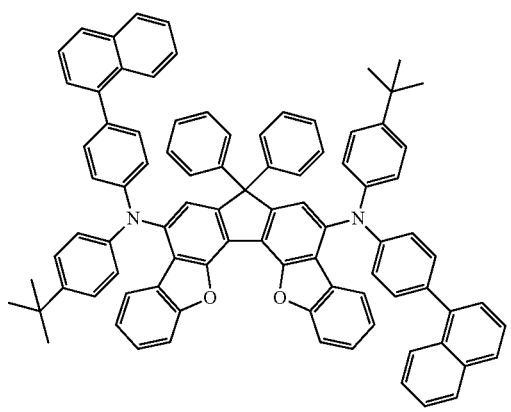

<Chemical Formula 145>
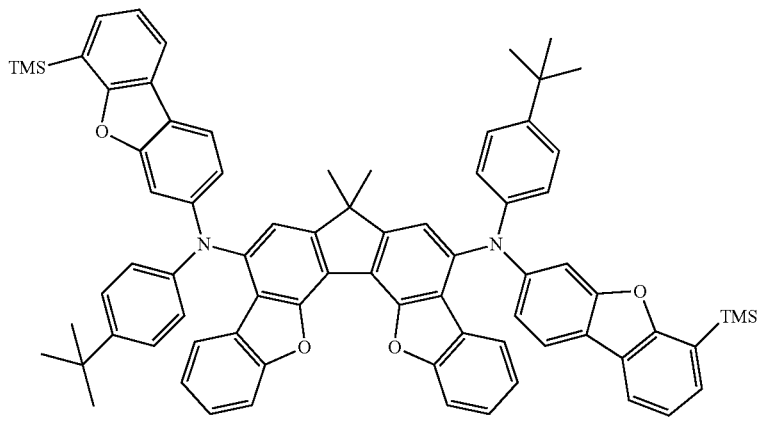
<Chemical Formula 146>
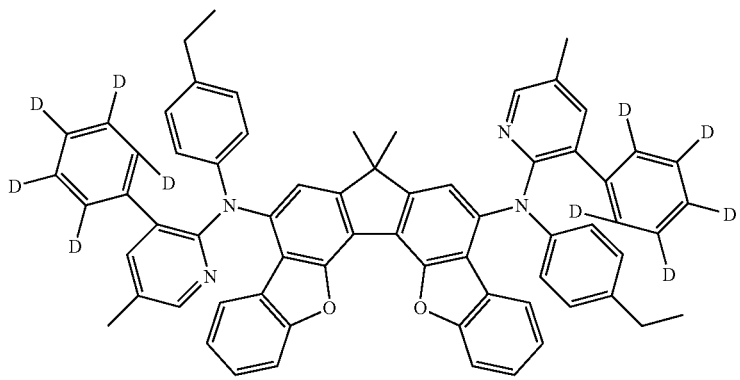
<Chemical Formula 147>
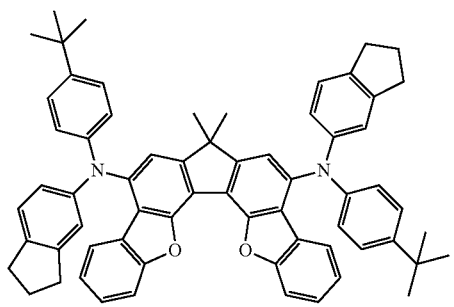
<Chemical Formula 148>
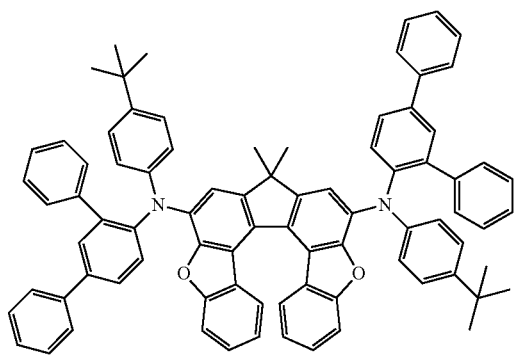
<Chemical Formula 149>
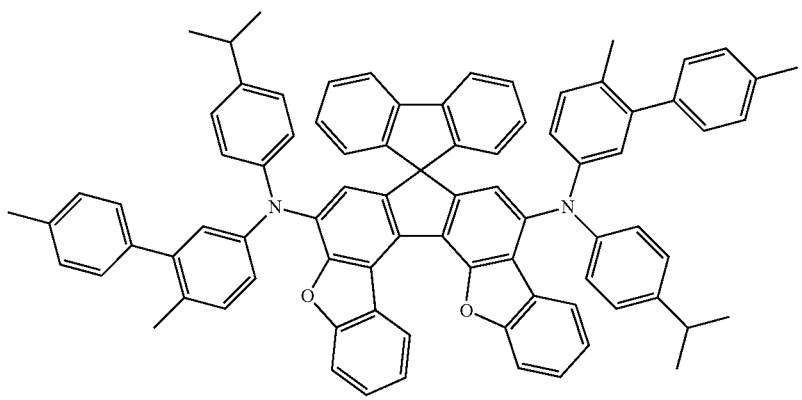

-continued
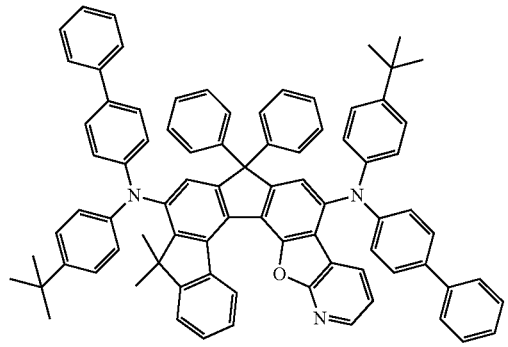
<Chemical Formula 160>
<Chemical Formula 162>
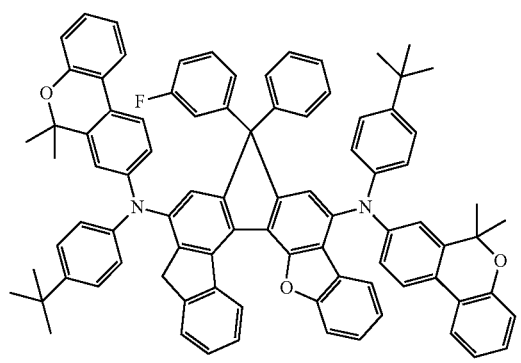
<Chemical Formula 164>
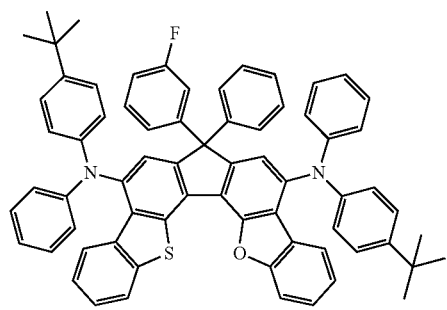
<Chemical Formula 165>
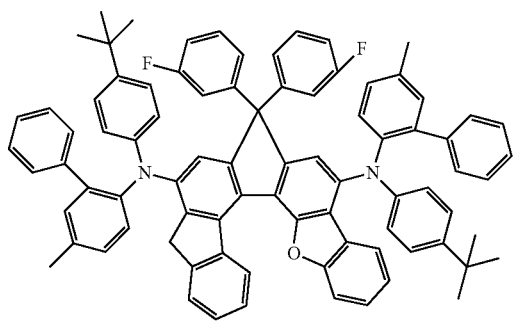

-continued
<Chemical Formula 197>
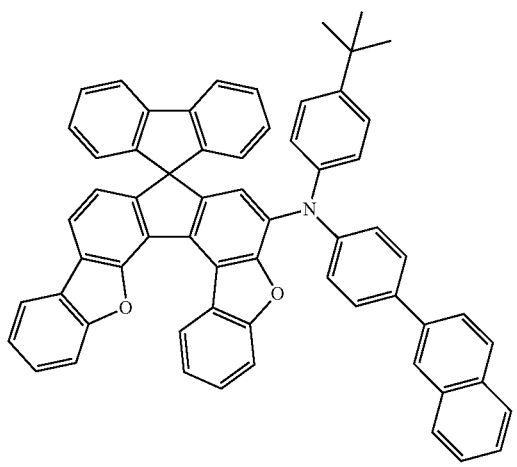
<Chemical Formula 198>
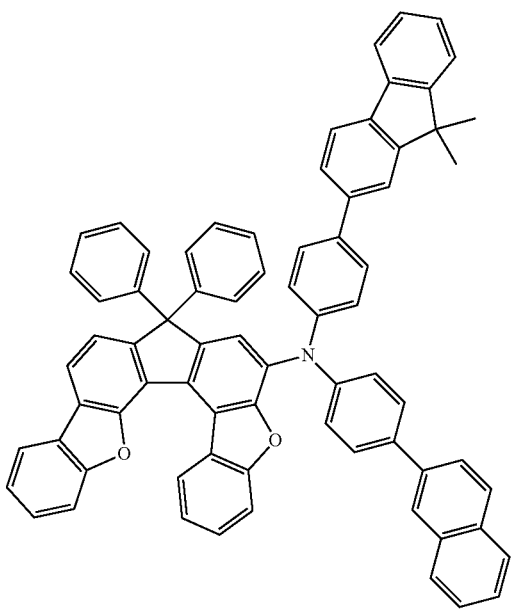
<Chemical Formula 199>
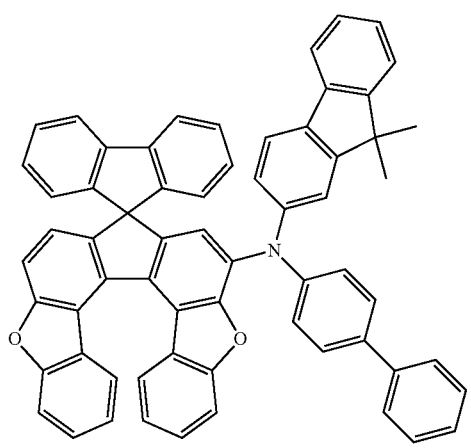
<Chemical Formula 200>
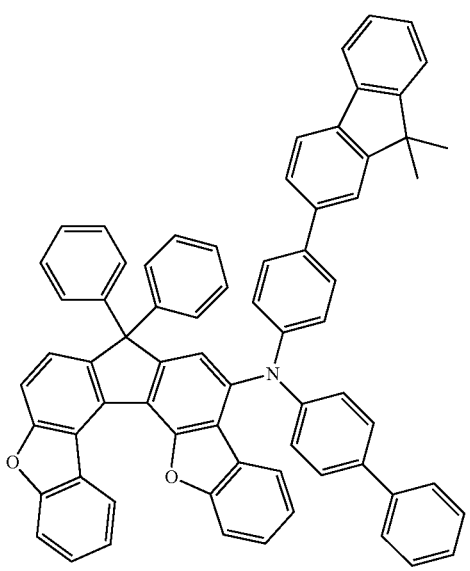
<Chemical Formula 201>
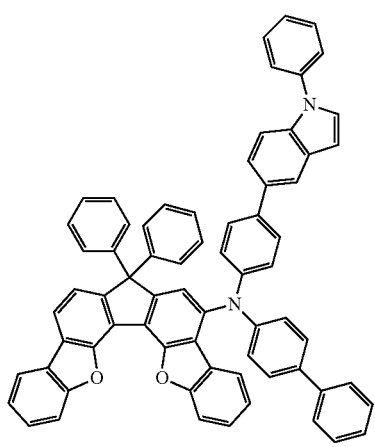

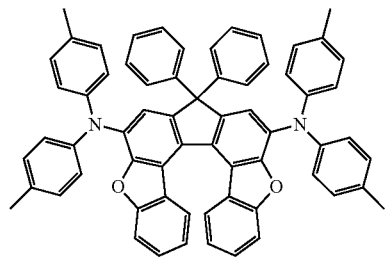
<Chemical Formula 210>
<Chemical Formula 222>
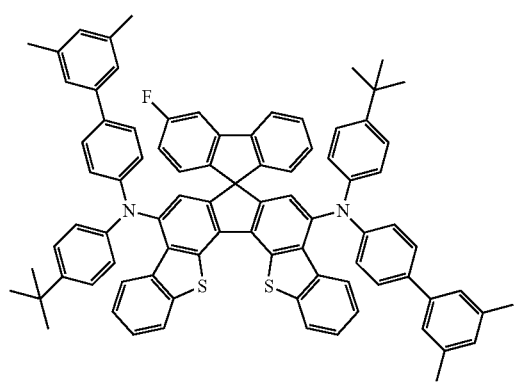
<Chemical Formula 223>
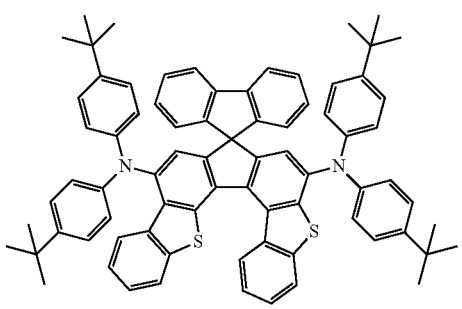
<Chemical Formula 224>
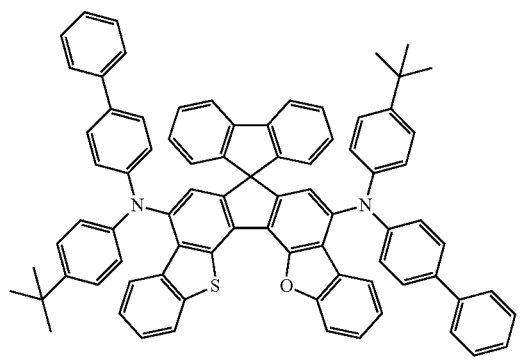
<Chemical Formula 227>
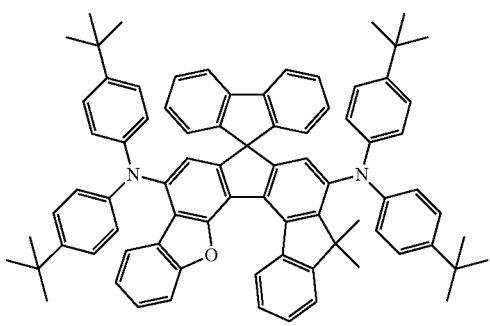

<Chemical Formula 228>
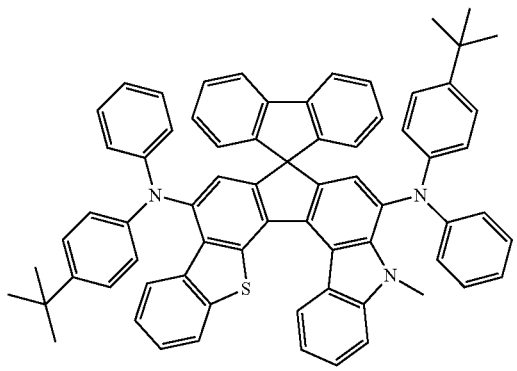
<Chemical Formula 229>
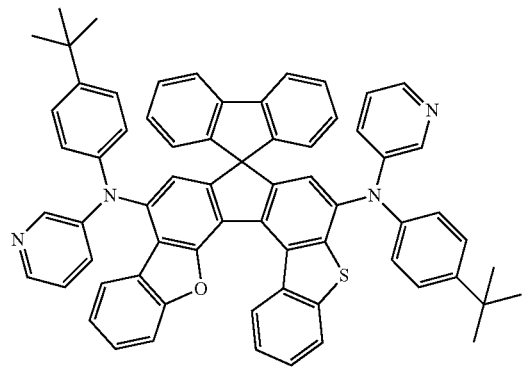
<Chemical Formula 230>
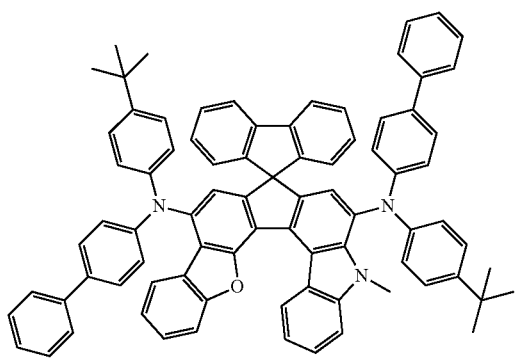
<Chemical Formula 231>
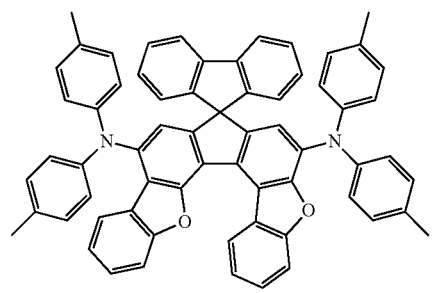
<Chemical Formula 239>
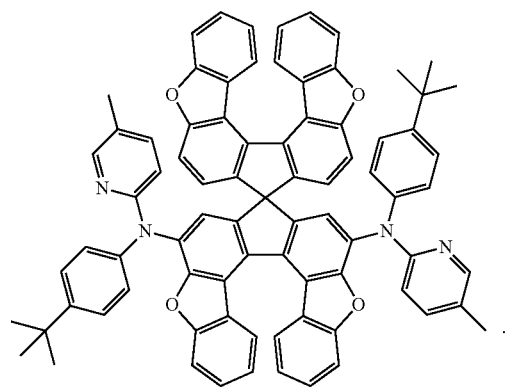

10. The organic light-emitting diode of claim 1, wherein the compound represented by Chemical Formula C is any one selected from among the compounds represented by [Cpd 201] to [Cpd 275]:
<Cpd. 201>
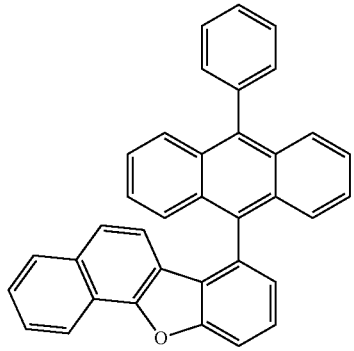
<Cpd. 202>
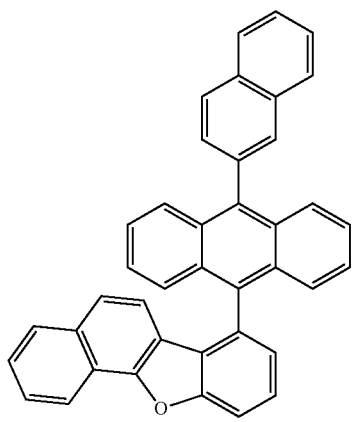
<Cpd. 203>
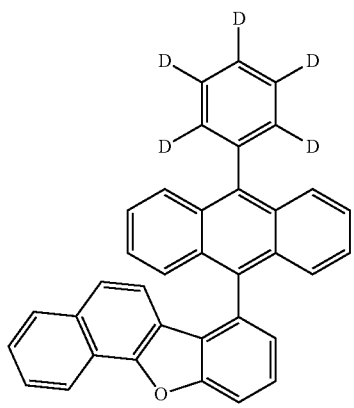
<Cpd. 204>
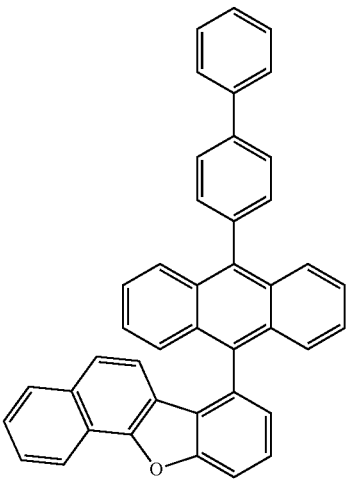
<Cpd. 205>
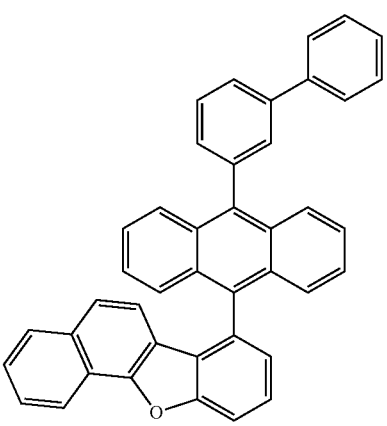
<Cpd. 206>
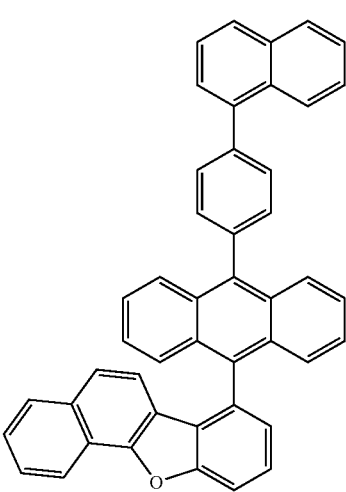

<Cpd. 207>
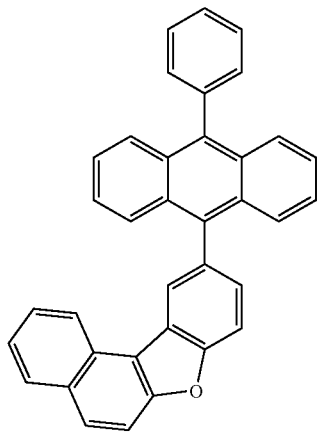
<Cpd. 208>
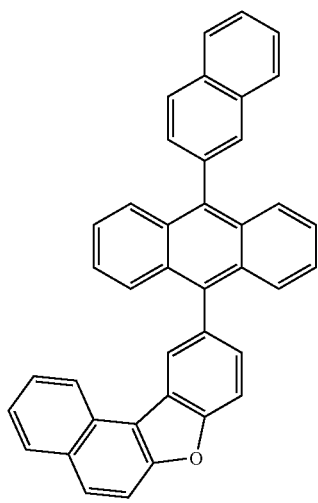
<Cpd. 209>
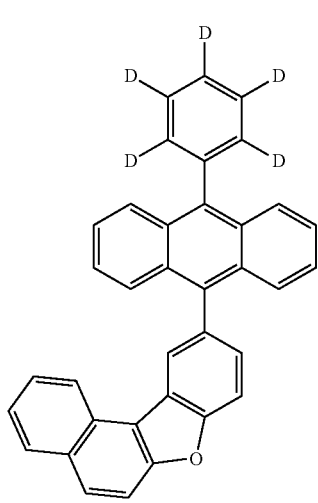
<Cpd. 210>
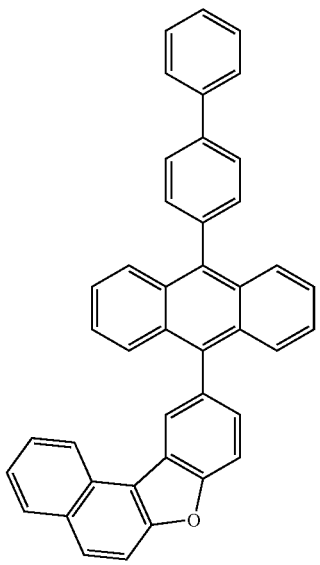
<Cpd. 211>
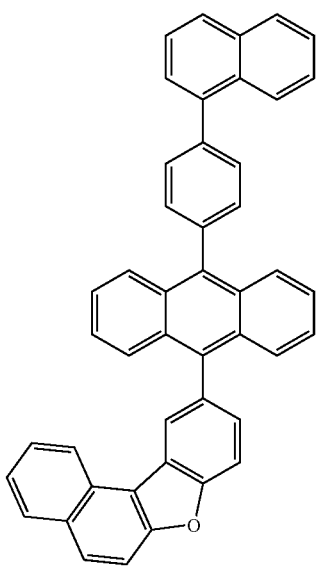

<Cpd. 212>
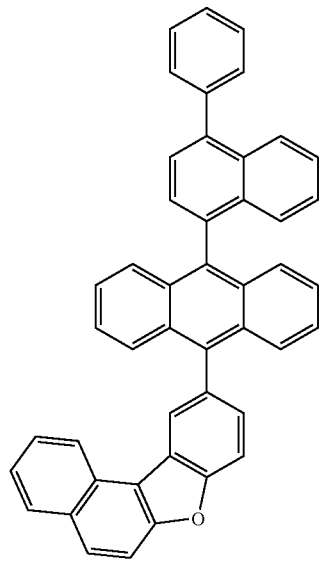
<Cpd. 213>
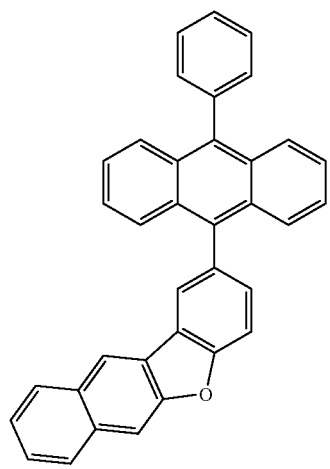
<Cpd. 214>
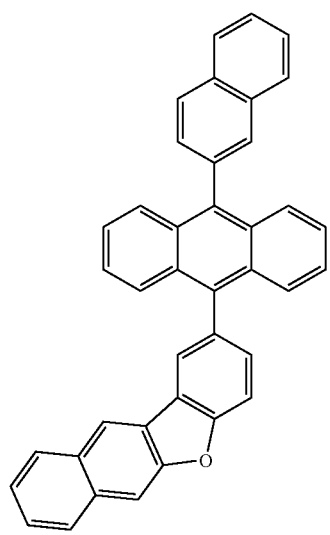
<Cpd. 215>
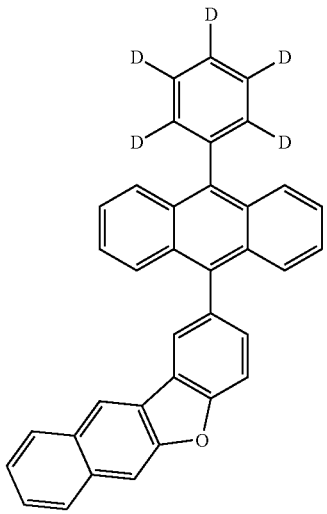
<Cpd. 216>
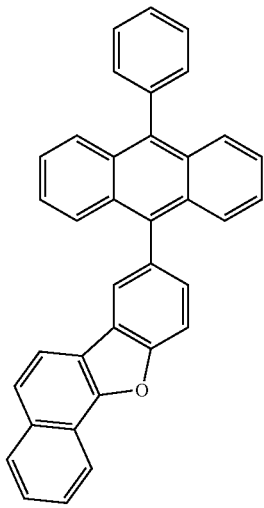
<Cpd. 217>
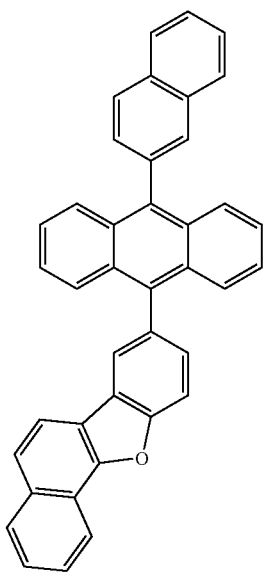

<Cpd. 218>
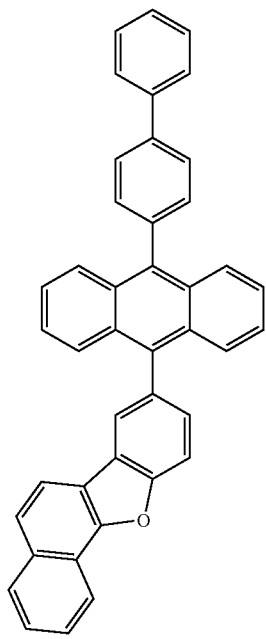
<Cpd. 220>
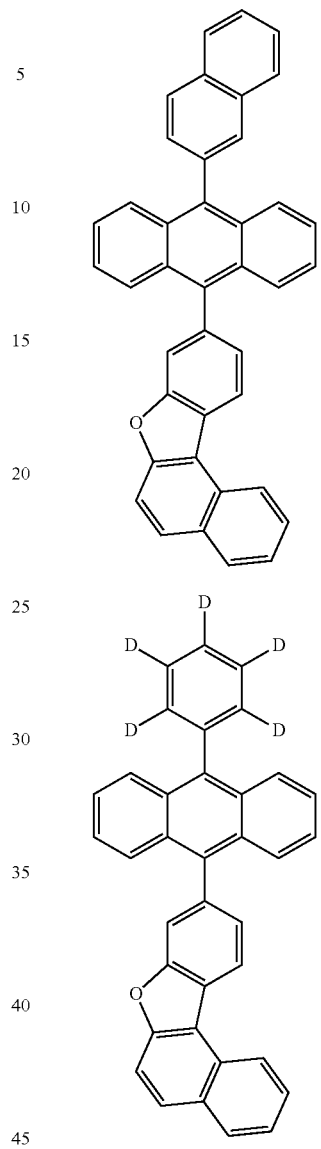
<Cpd. 221>
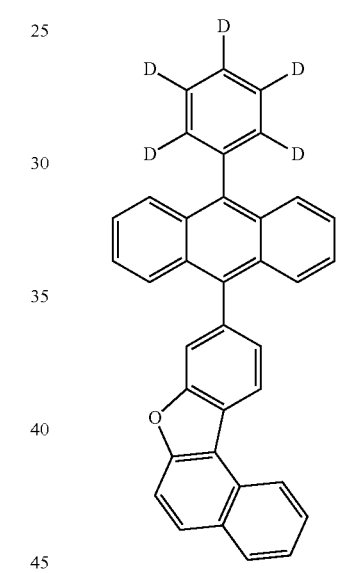
<Cpd. 219>
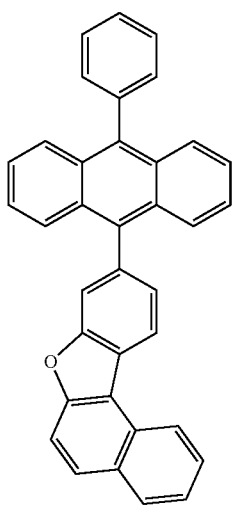
<Cpd. 222>
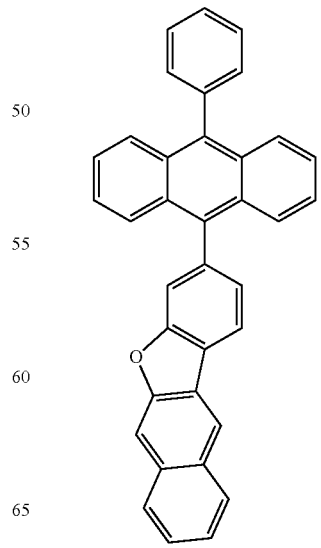

<Cpd. 223>
<Cpd. 226>
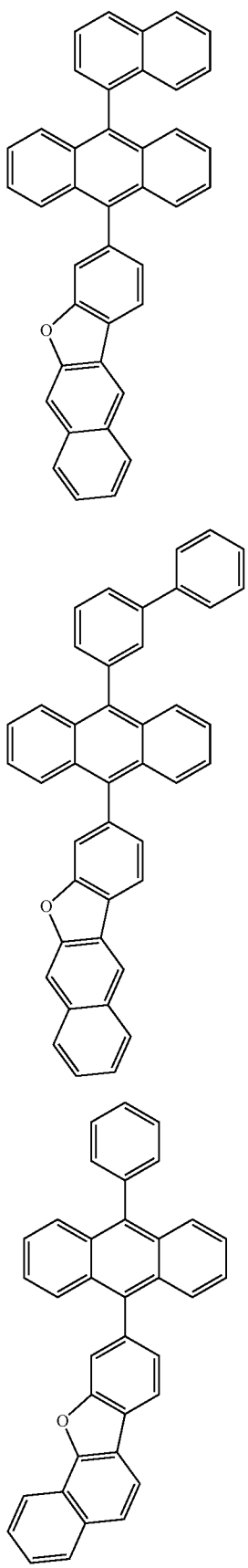
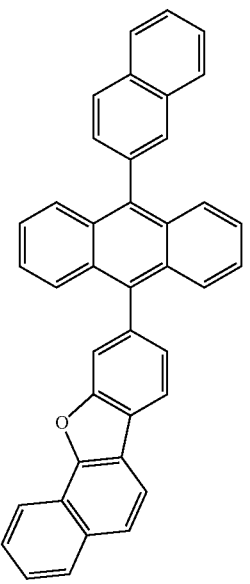
<Cpd. 224>
<Cpd. 227>
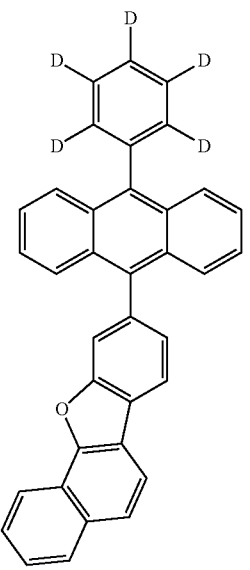
<Cpd. 225>
<Cpd. 228>
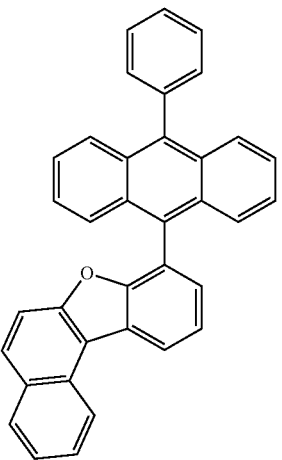

<Cpd. 229>
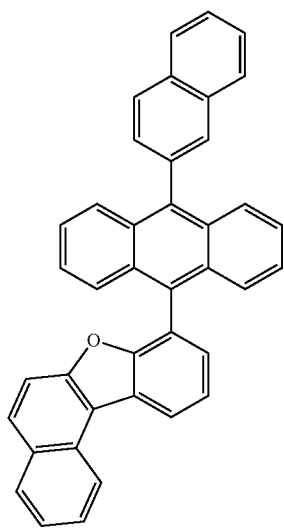
<Cpd. 232>
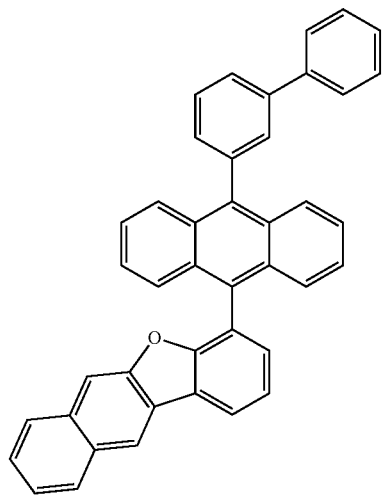
<Cpd. 230>
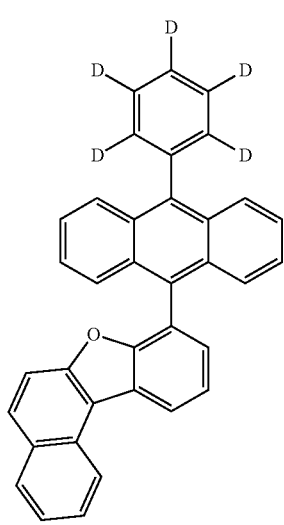
<Cpd. 233>
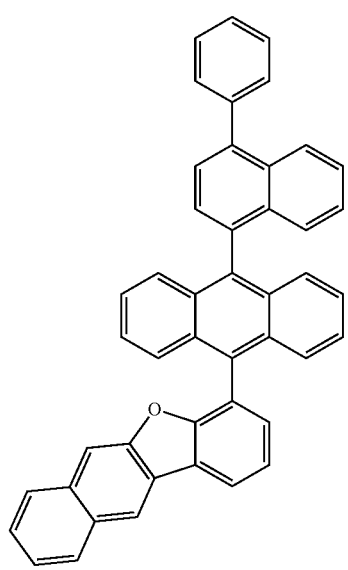
<Cpd. 231>
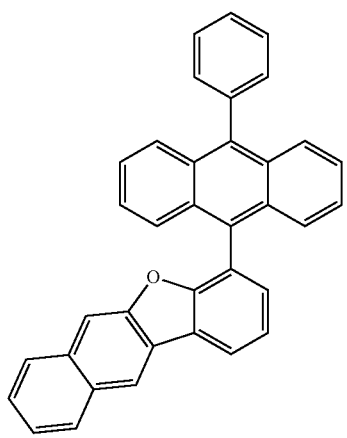
<Cpd. 234>
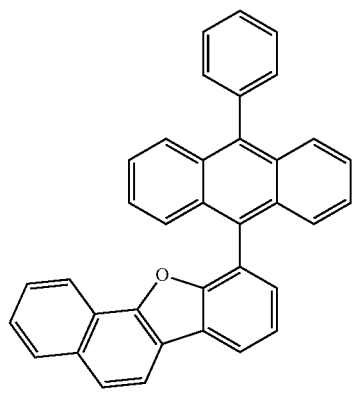

<Cpd. 235>
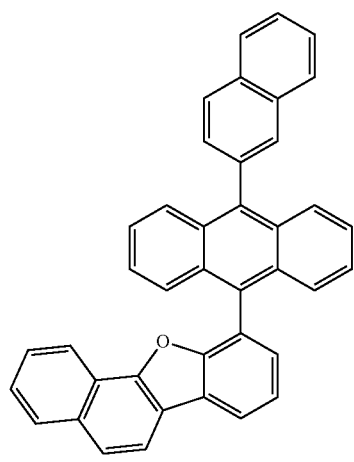
<Cpd. 236>
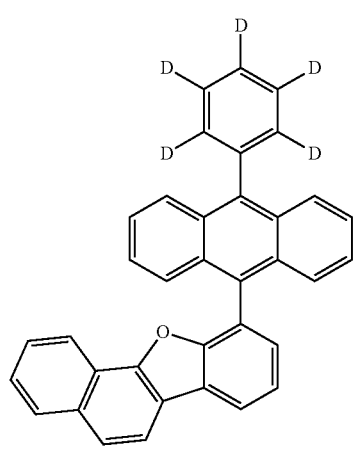
<Cpd. 237>
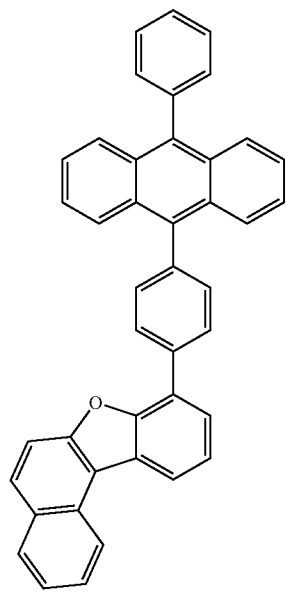
<Cpd. 238>
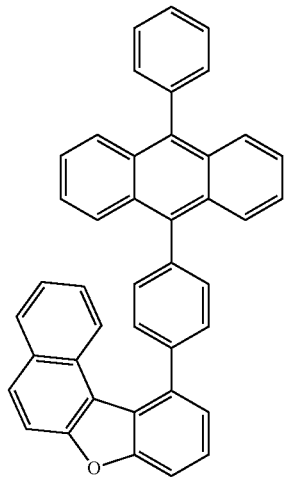
<Cpd. 239>
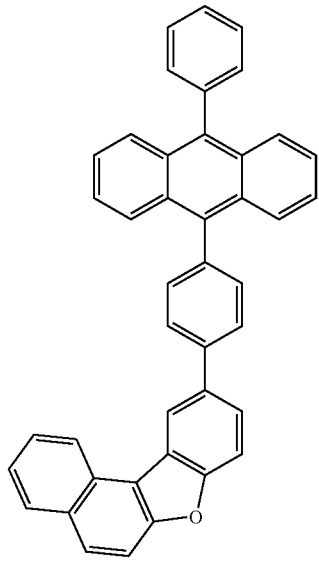

<Cpd. 240>
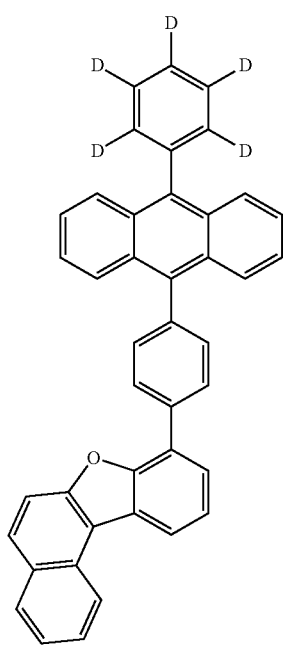
<Cpd. 241>
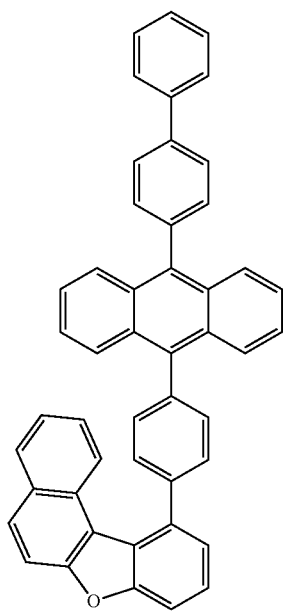
<Cpd. 242>
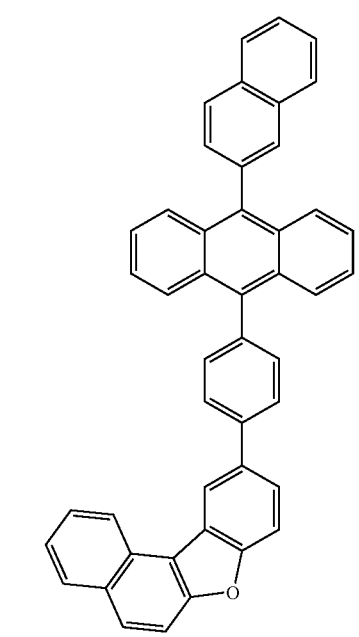
<Cpd. 243>
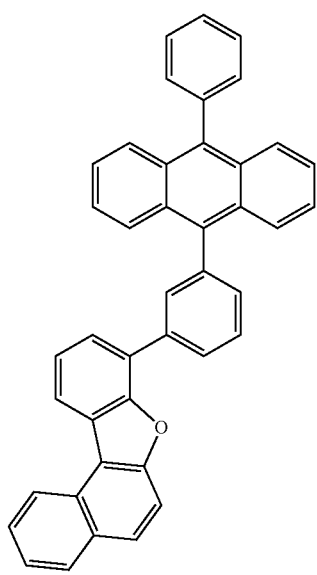

<Cpd. 244>
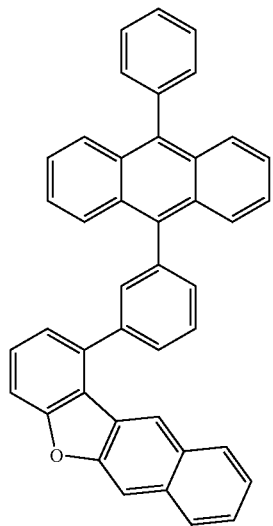
<Cpd.245>
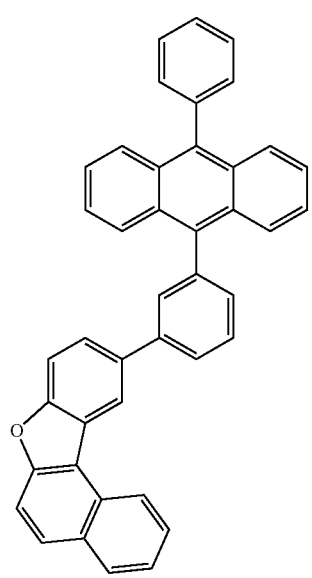
<Cpd 246>
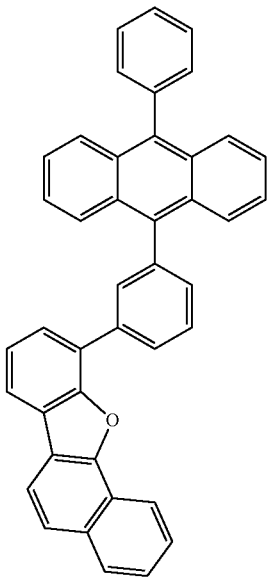
<Cpd. 247>
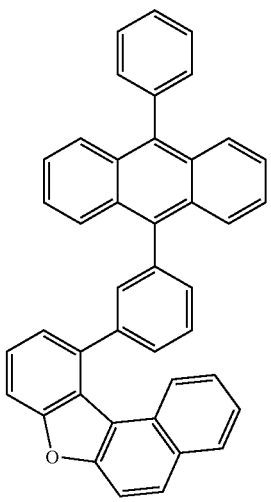
<Cpd. 258>
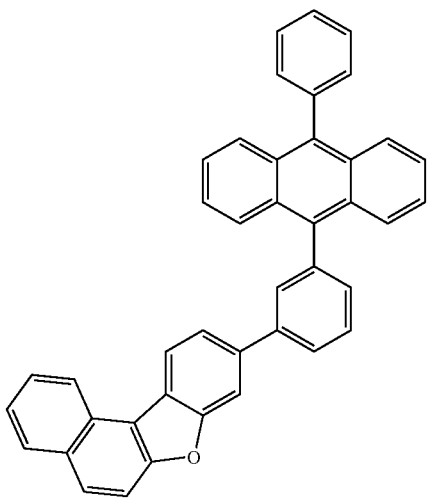

<Cpd. 249>
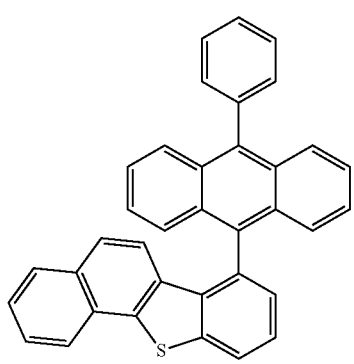
<Cpd. 250>
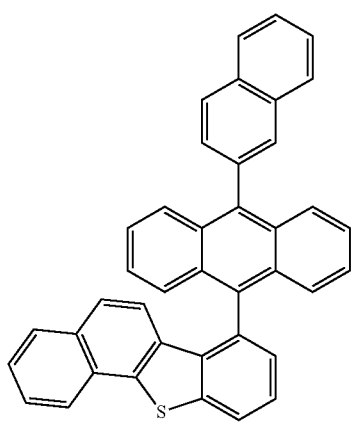
<Cpd. 251>
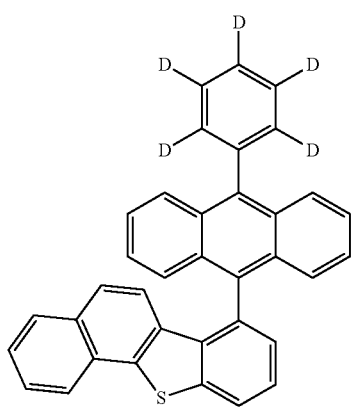
<Cpd. 252>
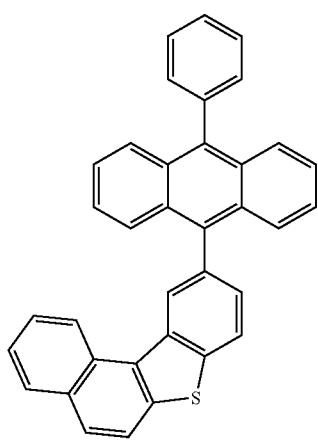
<Cpd. 253>
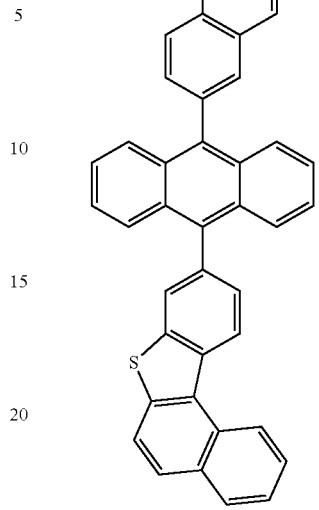
<Cpd. 254>
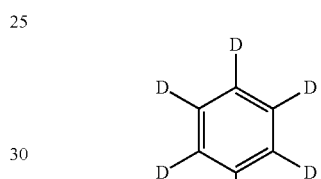
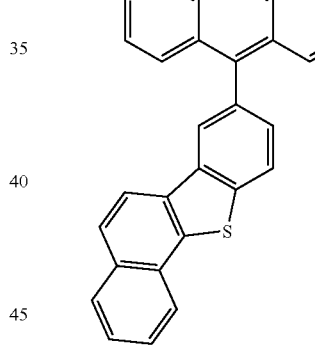
<Cpd. 255>
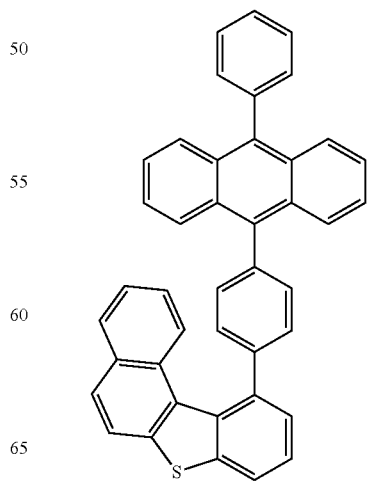

<Cpd. 256>
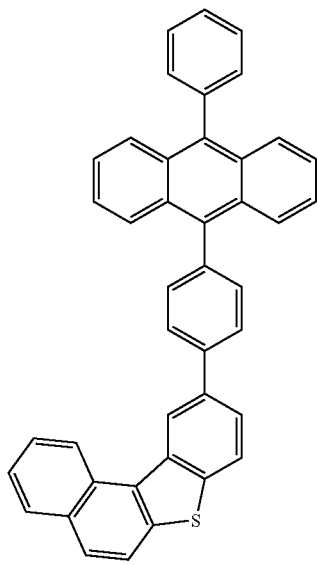
<Cpd. 258>
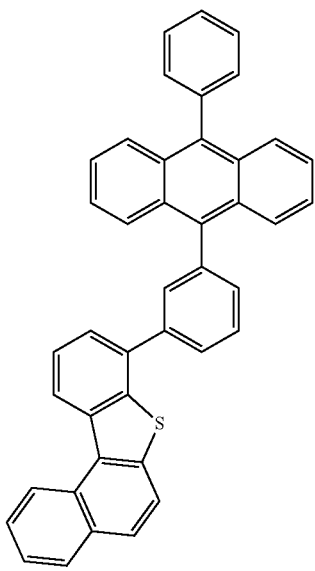
<Cpd. 257>
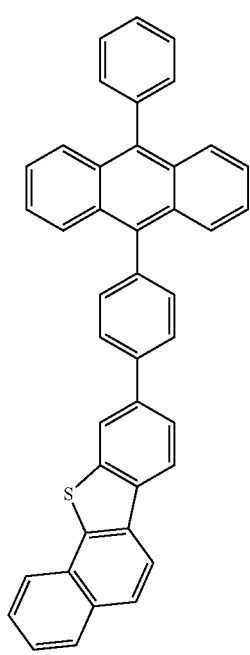
<Cpd. 259>
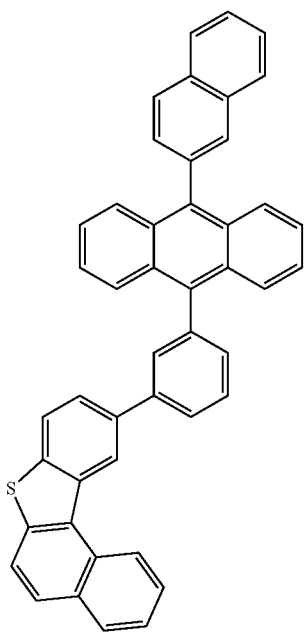

<Cpd. 260>
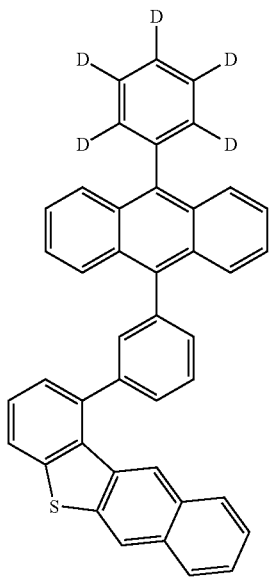
<Cpd. 263>
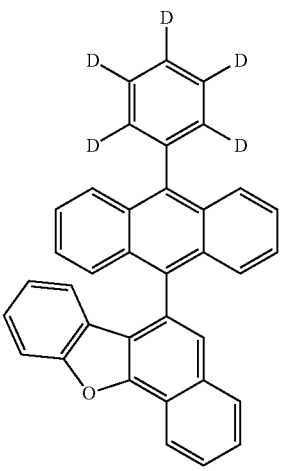
<Cpd. 261>
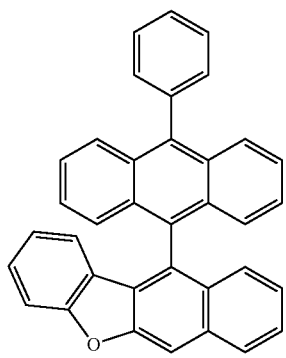
<Cpd. 264>
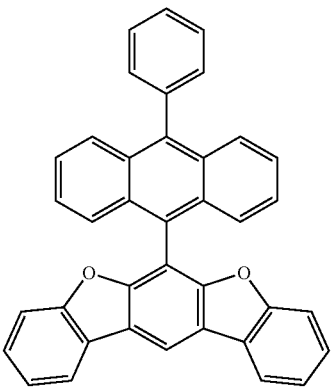
<Cpd. 262>
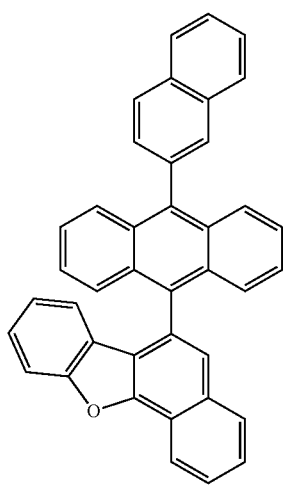
<Cpd. 265>
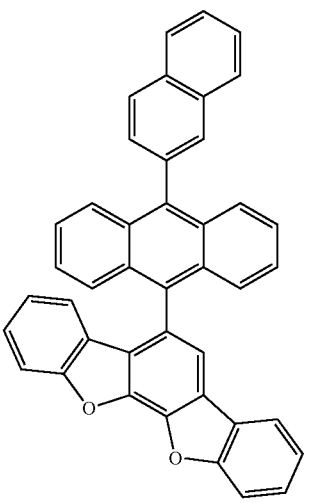

<Cpd. 266>
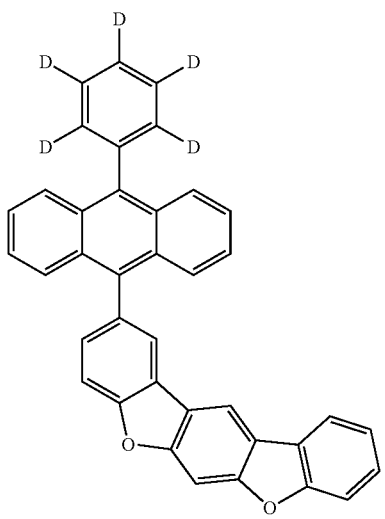
<Cpd. 267>
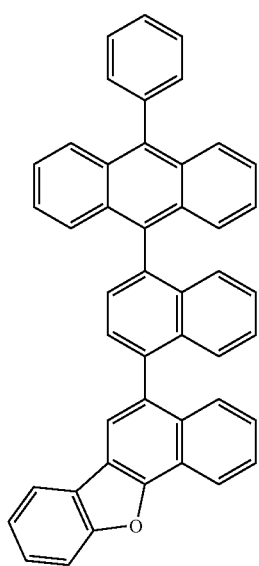
<Cpd. 268>
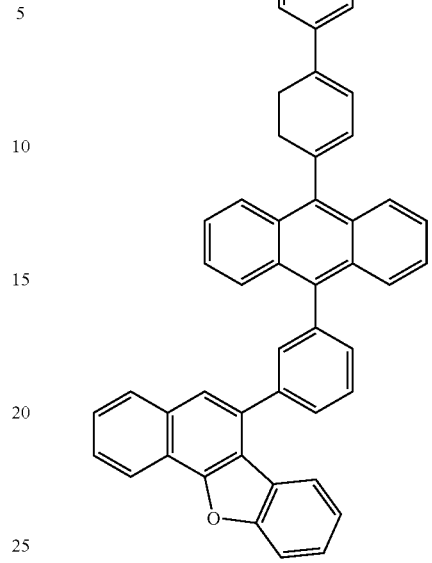
<Cpd. 269>
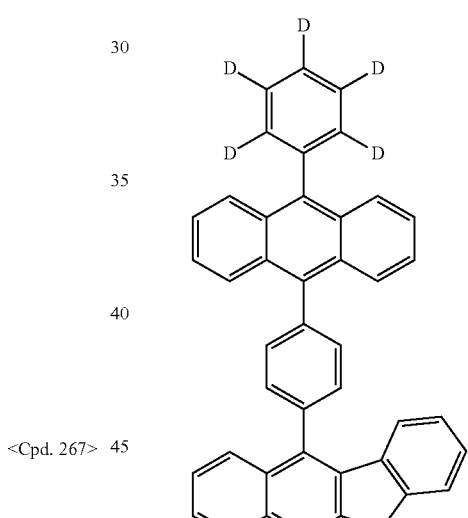
<Cpd. 270>
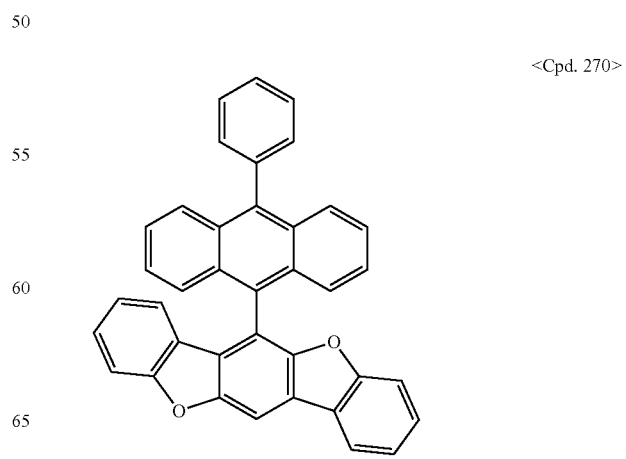

<Cpd. 271>

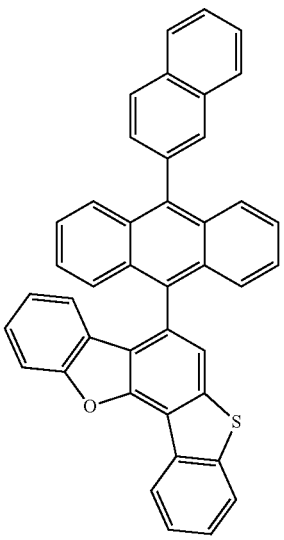

<Cpd. 272>

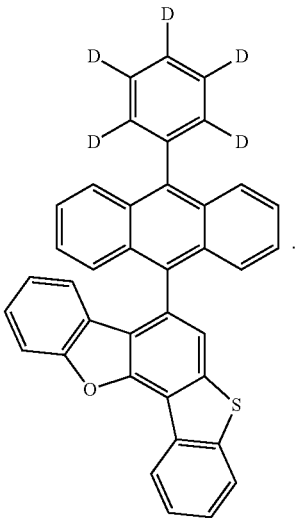

<Cpd. 274>

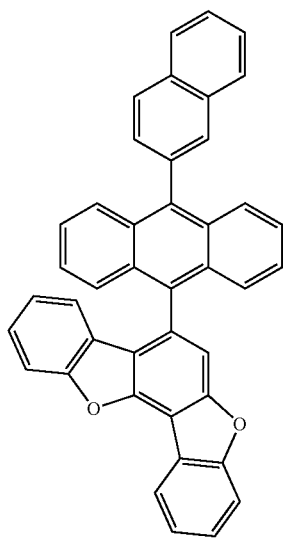

<Cpd. 275>

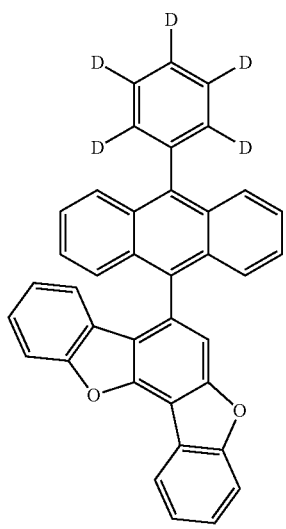

<Cpd. 273>

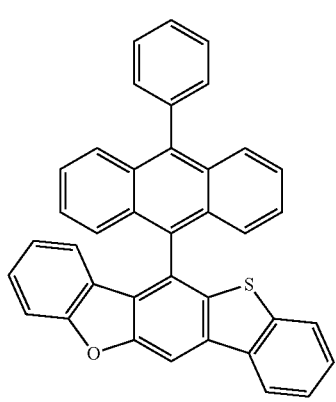

11. The organic light-emitting diode of claim 1, wherein the organic light-emitting diode comprises at least one of a hole injection layer, a hole transport layer, a functional layer capable of both hole injection and hole transport, an electron transport layer, and an electron injection layer, in addition to the light-emitting layer.

12. The organic light-emitting diode of claim 11, wherein at least one of the layers is formed using a deposition process or a solution process.

13. The organic light-emitting diode of claim 1, wherein organic light-emitting diode is used for a device selected from among a flat display device, a flexible display device, a monochrome or white flat illumination device, and a monochrome or white flexible illumination device.

* * * * *